(12) United States Patent
Nissan et al.

(10) Patent No.: US 11,197,907 B2
(45) Date of Patent: Dec. 14, 2021

(54) **ANTIMICROBIAL COMPOUNDS FROM THE GENUS *DELFTIA***

(71) Applicants: Ministry of Health, State of Israel, Jerusalem (IL); Sami Shamoon College of Engineering (R.A), Beer-Sheva (IL); Tel HaShomer Medical Research Infrastructure and Services Ltd., Ramat-Gan (IL)

(72) Inventors: Israel Nissan, Modiin (IL); Noa Lea Tejman-Yarden, Tel-Aviv (IL); Chaim Rubinovitz, Omer (IL); Yakov Davidov, Jerusalem (IL); Galia Rahav, Jerusalem (IL); Ari Robinson, Bnei-Atarot (IL); Yoram Shotland, LeHavim (IL)

(73) Assignees: Ministry of Health, State of Israel, Jerusalem (IL); Sami Shamoon College of Engineeing (R.A), Beer-Sheva (IL); Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 0 days.

(21) Appl. No.: 16/496,978

(22) PCT Filed: Mar. 28, 2018

(86) PCT No.: PCT/IL2018/050363
§ 371 (c)(1),
(2) Date: Sep. 24, 2019

(87) PCT Pub. No.: WO2018/178986
PCT Pub. Date: Oct. 4, 2018

(65) Prior Publication Data
US 2020/0268830 A1  Aug. 27, 2020

Related U.S. Application Data

(60) Provisional application No. 62/477,493, filed on Mar. 28, 2017.

(51) Int. Cl.
*A61K 38/08* (2019.01)
*A61P 31/04* (2006.01)
*A61K 33/242* (2019.01)
*C12N 1/20* (2006.01)
*C12P 21/02* (2006.01)
*A61K 45/06* (2006.01)

(52) U.S. Cl.
CPC ............ *A61K 38/08* (2013.01); *A61K 33/242* (2019.01); *A61P 31/04* (2018.01); *C12N 1/20* (2013.01); *C12P 21/02* (2013.01); *A61K 45/06* (2013.01)

(58) Field of Classification Search
CPC .... A61K 2300/00; A61K 38/08; A61K 31/35; A61K 33/242; A61K 45/06; A61P 31/04; C07K 14/195; C12N 1/20; C12P 21/02; Y02A 50/30; Y02A 50/473; Y02A 50/481
See application file for complete search history.

(56) References Cited

U.S. PATENT DOCUMENTS 10,174,401 B2 *  1/2019  Wyatt ..................... C07K 7/06

FOREIGN PATENT DOCUMENTS

| WO | WO 2014/107814 | 7/2014 |
|----|----------------|--------|
| WO | WO 2018/178986 | 10/2018 |

OTHER PUBLICATIONS

Wyatt et al. Gold biomineralization by a metallophore from a gold-associated microbe. Nature Chemical Biology • Feb. 2013 pp. 1-5. (Year: 2013).*
International Preliminary Report on Patentability dated Oct. 10, 2019 From the International Bureau of WIPO Re. Application No. PCT/IL2018/050363. (8 Pages).
International Search Report and the Written Opinion dated Jun. 21, 2018 From the International Searching Authority Re. Application No. PCT/IL2018/050363. (10 Pages).
Han et al. "Characterization of a Novel Plant Growth-Promoting Bacteria Strain Delftia Tsuruhatensis HR4 Both as a Diazotroph and a Potential Biocontrol Agent Against Various Plant Pathogens", Systemic and Applied Microbiology, 28(1): 66-76, Jan. 2005.
Jorgensen et al. "*Delftia lacustris* Sp. Nov., a Peptidoglycan-Degrading Bacterium From Fresh Water, and Emended Description of Delftia Tsuruhatensis as a Peptidoglycan-Degrading Bacterium", International Journal of Systemic and Evolutionary Microbiology, 59(Pt.9): 2195-2199, Published Online Jul. 15, 2009.
Prasannakumar et al. "Delftia Tsuruhatensis WGR-UOM-BT1, a Novel Rhizobacterium With PGPR Properties From *Rauwolfia serpentina* (L.) Benth. Ex Kurz Also Suppresses Fungal Phytopathogens by Producing a New Antibiotic—AMTM", Letters in Applied Microbiology, 61(5): 460-468, Published Online Sep. 29, 2015.
Ribbons et al. "Oxidative Metabolism of Phthalic Acid by soil Pseudomonads", Biochemical Journal, 76(2): 310-318, Aug. 1, 1960. Experimental Section.
Supplementary European Search Report and the European Search Opinion dated Dec. 14, 2020 From the European Patent Office Re. Application No. 18778159.6. (7 Pages).
Johnstone et al. "Beyond Iron: Non-Classical Biological Functions of Bacterial Siderophores", Dalton Transactions, XP055282123, 44(14): 6320-6339, Published Online Feb. 18, 2015.

* cited by examiner

*Primary Examiner* — Marcela M Cordero Garcia

(57) ABSTRACT

Cultures of Delftia bacteria are disclosed. Antimicrobial agents derived therefrom are also disclosed.

6 Claims, 59 Drawing Sheets
(56 of 59 Drawing Sheet(s) Filed in Color)

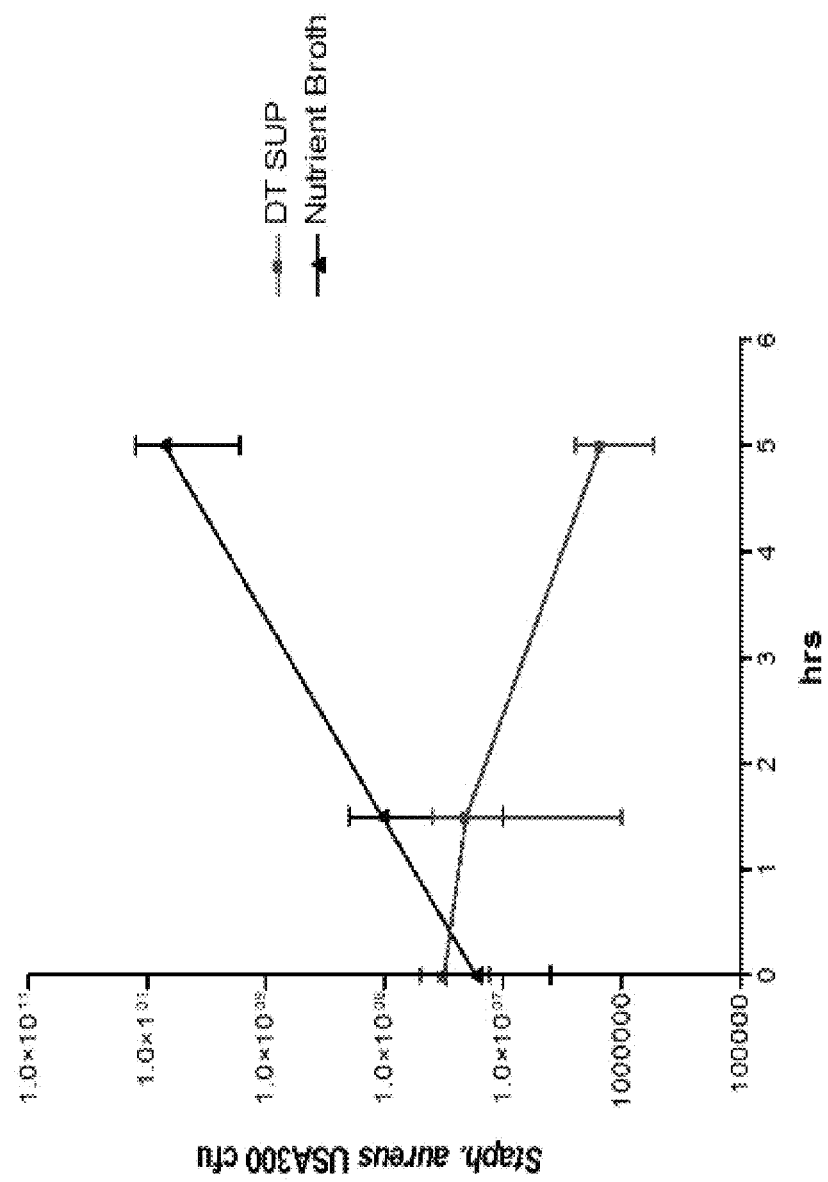

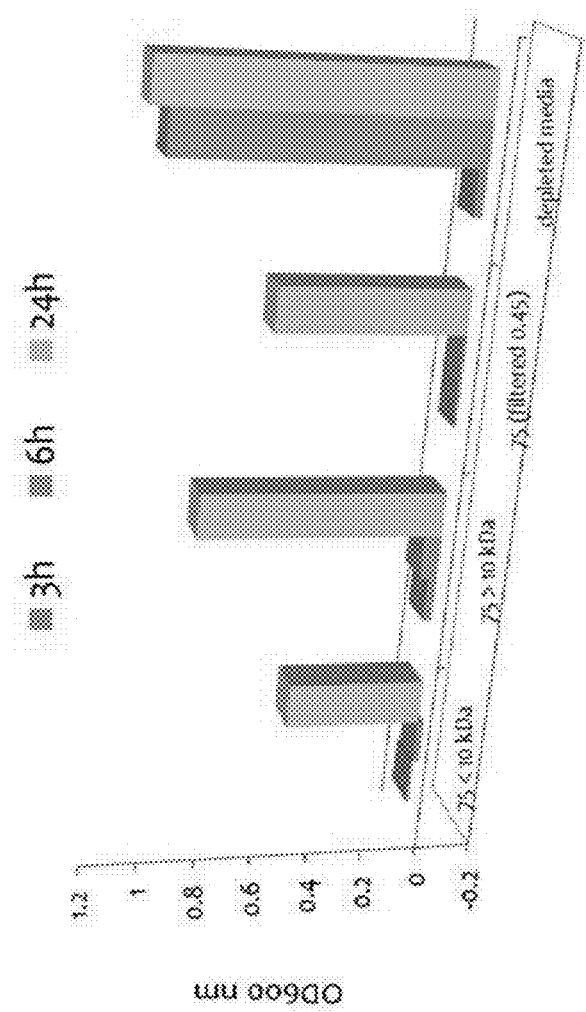

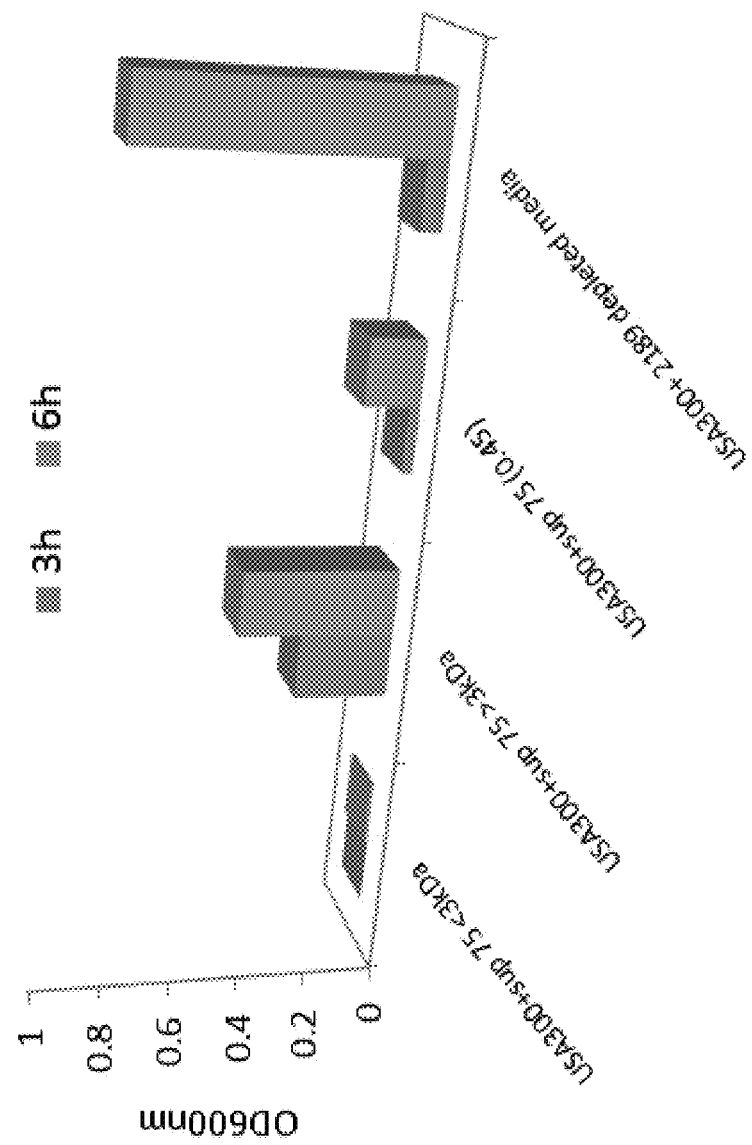

Effect of strains 75 and 2189 grown in defined minimal media against USA300

Effect of strains 75 and 2189 grown in defined minimal media against ACB

FIG. 13

| 2189 | | 75 | |
|---|---|---|---|
| RT (min) | peaks (nm) | RT (min) | peaks (nm) |
| - | - | 2.96 | 220,348 |
| - | - | 4.54 | 242,284 |
| 3.21 | 274 | 3.32 | 309 |
| 9.04 | 271,290,340 | 9.02 | 272,300,350 |
| - | - | 9.79 | 260 |
| 10.04 | 258,340 | 10.03 | 254,280 |
| 10.55 | 273 | 10.48 | 273 |
| 10.57 | 273 | - | - |
| 10.73 | 220,269 | 10.64 | 220,269 |
| 11.18 | 220 | - | - |
| - | - | 11.74 | 220,275 |
| 12.23 | 220 | - | - |
| - | - | 13.26 | 220,277 |
| 13.79 | 220,271,339 | - | - |

Shared peaks / 75 specific / 2189 specific

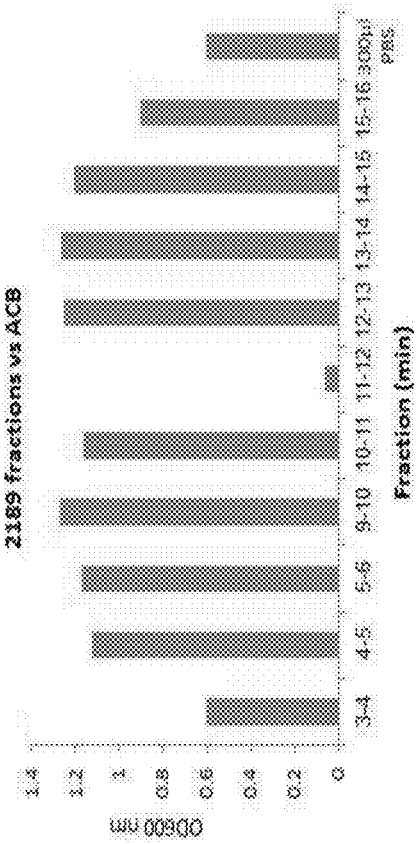
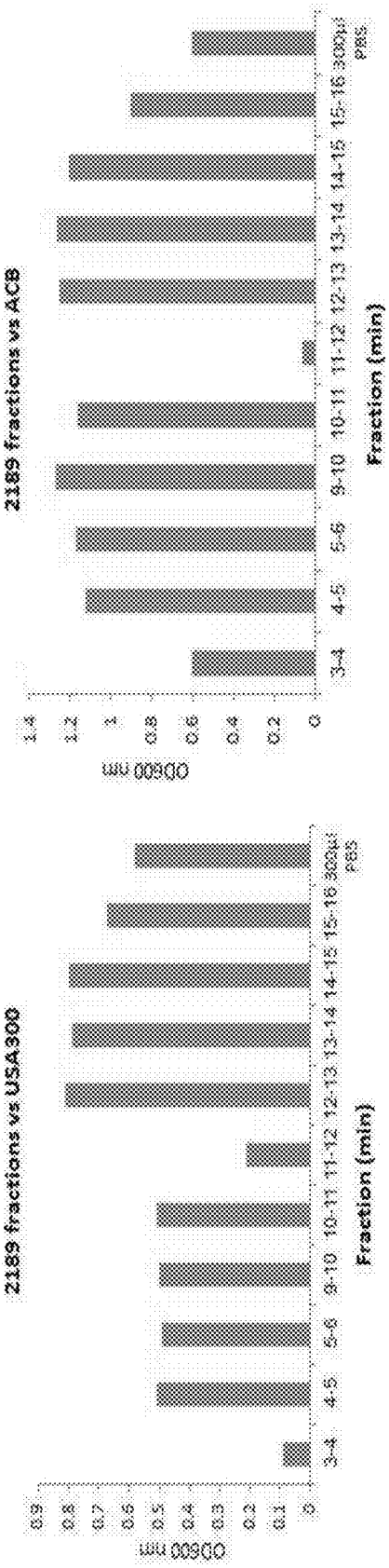
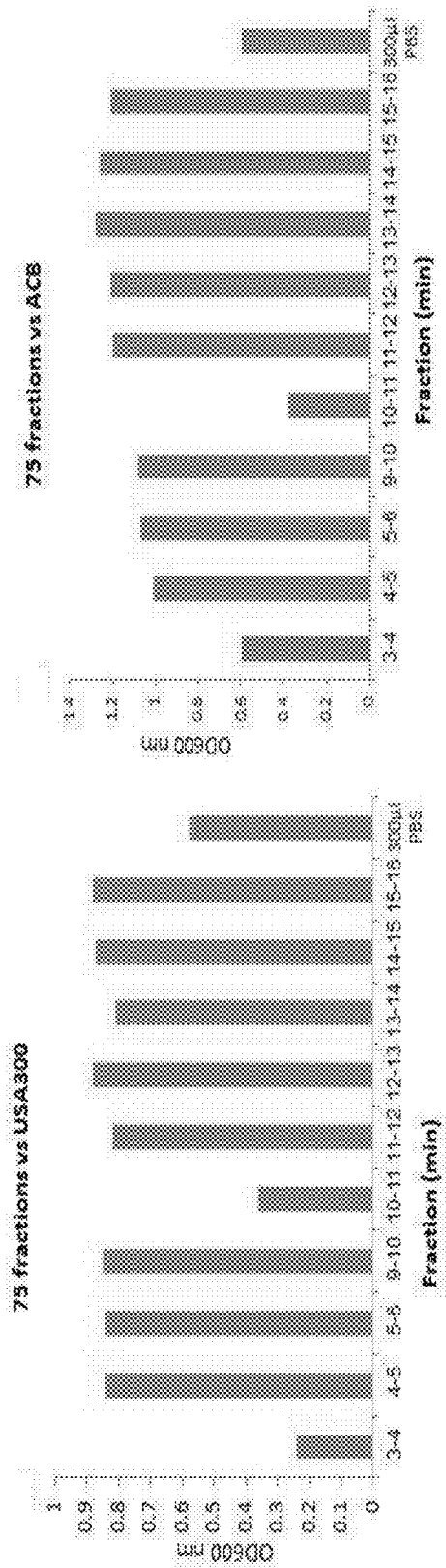
FIG. 14A  FIG. 14B  FIG. 14C  FIG. 14D

Strain 2189 spectra analysis of probable active peaks

FIG. 16
Strain 75 spectra analysis of probable active peaks
Fraction 3-4 min
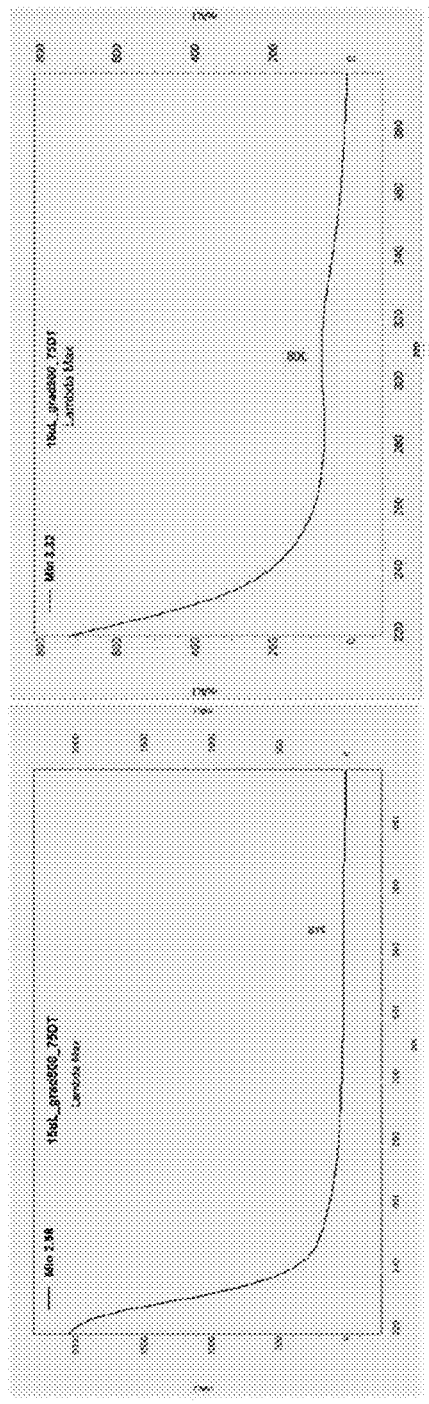
Fraction 10-11 min
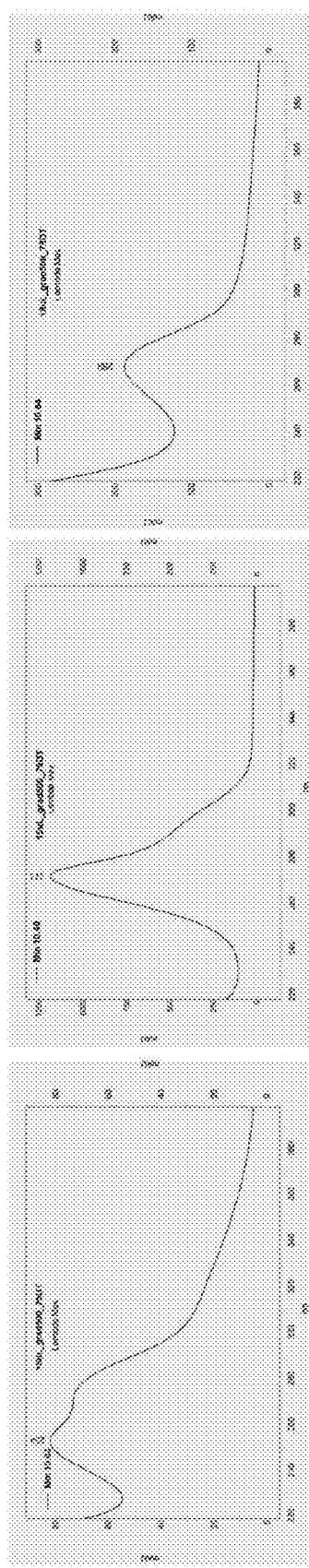

FIG. 21

| Target Tested 007 clone | % Inhibition |||||||| 
|---|---|---|---|---|---|---|---|---|
| | AP ||  E.Coli || Staph aureus || Enterococcus ||
| | 37°C | 30°C | 37°C | 30°C | 37°C | 30°C | 37°C | 30°C |
| 119 | 47.60% | 53.60% | 44.00% | 86.10% | 43.10% | 75.00% | 35.70% | 45.60% |
| 120 | 43.70% | 63.10% | 32.50% | 63.80% | 19.40% | 78.00% | 39.10% | 51.90% |
| 122 | 40.00% | 75.30% | 33.10% | 75.50% | 4.00% | 71.90% | 34.20% | 52.50% |
| 123 | 34.90% | 60.10% | 30.70% | 60.80% | 16.40% | 51.30% | 16.00% | 41.80% |
| 159 | 38.60% | 18.70% | 30.70% | 29.50% | 9.50% | 8.50% | 29.00% | 32.30% |
| 160 | 36.60% | 24.40% | 26.50% | 34.90% | 29.90% | 21.40% | 34.80% | 43.10% |
| 2248 | 15.10% | 61.50% | 18.80% | 40.30% | 15.00% | 29.00% | 27.80% | 43.20% |
| 2260 | 0.90% | 31.50% | 22.10% | 41.60% | 3.90% | 9.50% | 15.70% | 45.50% |
| 2350 | 21.00% | 33.60% | 18.90% | 10.20% | 0.60% | 15.00% | 29.40% | 34.50% |
| 2361 | 35.80% | 66.00% | 34.20% | 60.00% | 39.30% | 72.20% | 27.80% | 45.80% |
| T7 | 43.00% | 49.00% | 39.60% | 53.70% | 11.00% | 47.60% | 22.30% | 35.60% |

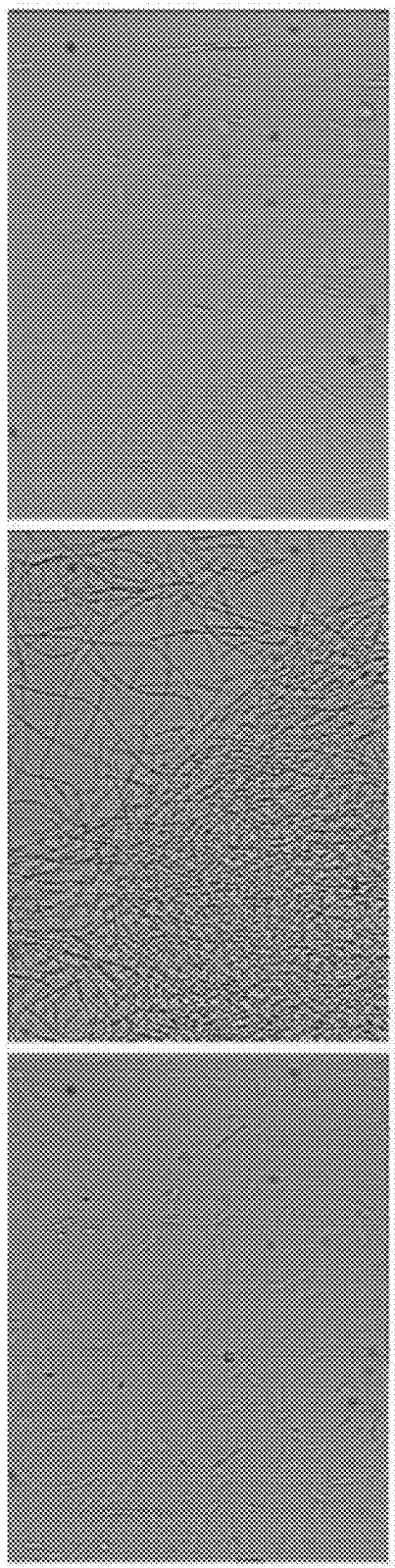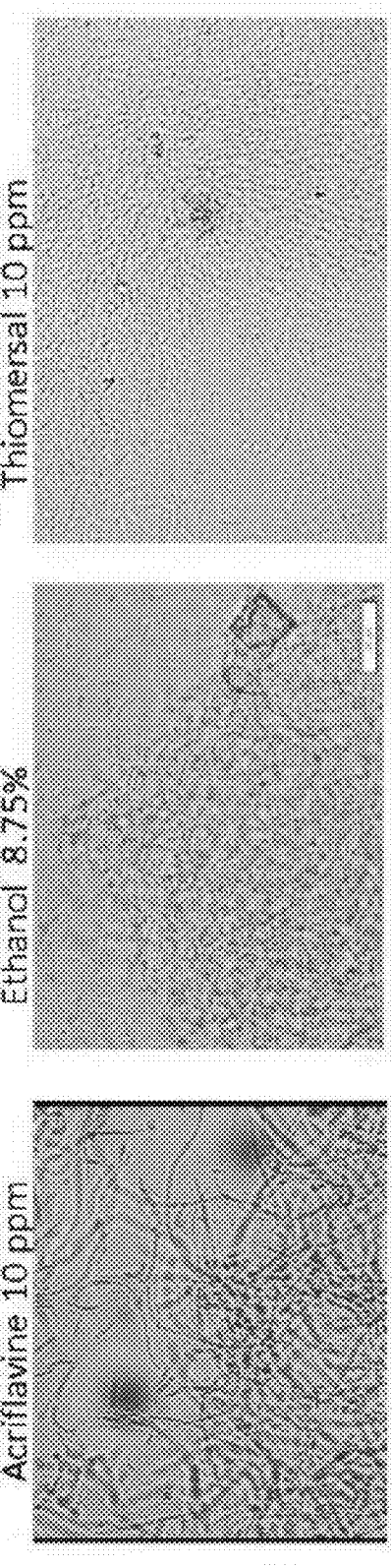
FIG. 23A ampicillin
FIG. 23B Acriflavine 10 ppm
FIG. 23C Ethanol 8.75%
FIG. 23D Thiomersal 10 ppm
1) control
2) 4000 mcg/ml ampicillin
3) Reversion into regular morphology

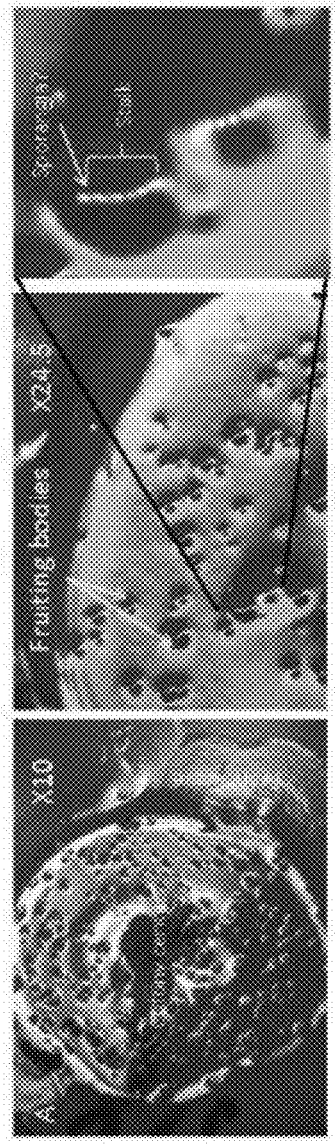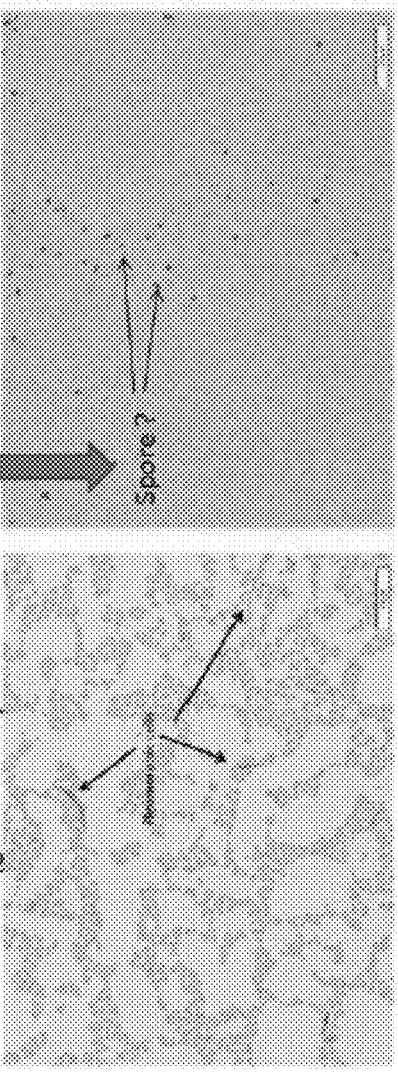
FIG. 24A  The central colony with fruiting bodies, after 6 days at 30°C
FIG. 24B  DT clone 2189 fresh culture (gram stain)
FIG. 24C  DT clone 2189 –FB (gram stain, after 6 days)

ANTIMICROBIAL COMPOUNDS FROM THE GENUS *DELFTIA*

RELATED APPLICATIONS

This application is a National Phase of PCT Patent Application No. PCT/IL2018/050363 having International filing date of Mar. 28, 2018, which claims the benefit of priority under 35 USC § 119(e) of U.S. Provisional Patent Application No. 62/477,493 filed on Mar. 28, 2017. The contents of the above applications are all incorporated by reference as if fully set forth herein in their entirety.

FIELD AND BACKGROUND OF THE INVENTION

The present invention, in some embodiments thereof, relates to antimicrobial agents derived from *Delftia* bacteria.

The excessive global use of antimicrobial drugs in humans as well as agriculture and veterinary medicine has led to the emergence of new multidrug resistant pathogens. Many of these pathogens are globally spread and treatment options for clinicians are becoming limited.

Among the Gram positive "spectrum", bacteria posing threats of resistance are the methicillin resistant *Staphylococcus aureus* (MRSAs). The MRSAs are traditionally divided into community acquired MRSA (CA-MRSA) and hospital acquired MRSA (HA-MRSA). The HA-MRSA are in general more resistant than CA-MRSA due to a larger "Staphylococcal Chromosomal Cassette" region (SCCmec). The CA-MRSA clone USA300 evolved in the USA in year 2000. Within a few years it has spread extensively across the USA, effectively marginalizing other *S. aureus* strains, MRSA as well as MSSA. This successful and virulent clone has gained a worldwide distribution. It is mainly community-associated, but hospital-associated cases also occur. Another example is the vancomycin-resistant enterococci which are prevalent across the globe. Due to the increase in factors predisposing the risk of infection and carriage of resistance to today's' arsenal of antibiotics, there is an increasing demand for new compounds with antibacterial activity which bypass/overcome resistance.

*Delftia* sp. are motile, Gram negative rods, which belong to the Betaproteobacteria lineage. Several *Delftia* species are known for their biodegradation abilities of various toxic carbon compounds including phenols and aniline. The genus *Delftia* contains several species, including *D. acidovorans, D. lacustris, D. litopenaei* and *D. tsuruhatensis*. Bacteria belonging to this genus are rarely involved in human infection, mainly as opportunistic pathogens.

Background art includes Hou Q et al., Genome Announc. 2015 July-August; 3(4): e00822-15 and Prasannakumar, S. P et al., Letters in Applied Microbiology, 2015, 61: 460-468. doi: 10.1111/1am.12479.

US Patent Application No. 20150354024 teaches isolation of gold using metabolites of Delftia.

U.S. Pat. No. 9,842,198 teaches screening methods for identifying Delftibactin-like molecules.

SUMMARY OF THE INVENTION

According to an aspect of the present invention there is provided a method of treating an infection in a subject in need thereof, the method comprising administering to the subject a therapeutically effective amount of a Delftibactin, thereby treating the infection.

According to an aspect of the present invention there is provided a method of killing a microbe, the method comprising contacting the microbe with Delftibactin, thereby killing the microbe.

According to an aspect of the present invention there is provided a composition comprising a Delftibactin and an antibiotic.

According to an aspect of the present invention there is provided an article of manufacture comprising a Delftibactin and an antibiotic.

According to an aspect of the present invention there is provided a method of generating an antimicrobial agent comprising:

(a) culturing a *Delftia* bacteria in a medium under conditions effective to allow secretion of at least one antimicrobial agent into the medium; and (b) purifying the at least one antimicrobial agent from the medium to generate a purified preparation comprising the at least one antimicrobial agent, wherein the antimicrobial agent is not $C_{17}H_{19}NO_3S$ or a Delftibactin, thereby generating the antimicrobial agent.

According to an aspect of the present invention there is provided a cell culture comprising a culture medium and a *Delftia* bacteria which comprises a genome having a polynucleotide sequence at least 90% homologous to the polynucleotide sequence filed under the Accession no. ERS1087230, SAMEA3900096-DT123; ERS1087231, SAMEA3900097-DT2361; ERS1087229, SAMEA3900095-DT122; ERS1087228, SAMEA3900094-DT120; ERS1087227, SAMEA3900093-DT119; ERS1087226 SAMEA3900092-DT75; or ERS1090440, SAMEA3903306-Delftia strain 2189.

According to an aspect of the present invention there is provided a composition of matter comprising at least one antimicrobial agent generated according to the method described herein.

According to an aspect of the present invention there is provided a composition of matter comprising at least one antimicrobial agent secreted from a *Delftia* bacteria, wherein the at least one antimicrobial agent is more than 1% of the *Delftia* components in the composition of matter, wherein the at least one antimicrobial agent is not $C_{17}H_{19}NO_3S$ or a Delftibactin.

According to an aspect of the present invention there is provided a pharmaceutical composition comprising at least one antimicrobial agent generated according to the method described herein, as the active agent and a pharmaceutically acceptable carrier.

According to an aspect of the present invention there is provided a method of treating an infection in a subject in need thereof, the method comprising administering to the subject a therapeutically effective amount of the composition described herein, thereby treating the infection.

According to an aspect of the present invention there is provided a solid support coated with at least one antimicrobial agent generated according to the method described herein or the composition described herein.

According to an aspect of the present invention there is provided a method of killing a microbe, the method comprising contacting the microbe at least one antimicrobial agent generated according to the method described herein or the composition described herein, thereby killing the microbe.

According to an aspect of the present invention there is provided a culture medium comprising:

(i) $KH_2PO_4$;
(ii) $(NH_4)_2SO_4$;

(iii) MgSO$_4$; and
(iv) Phthalic acid.

According to an aspect of the present invention there is provided a method of propagating *Delftia* bacteria comprising culturing the bacteria in the medium described herein, thereby propagating the *Delftia* bacteria.

According to some embodiments of the invention, the method further comprises administering to the subject an antibiotic.

According to some embodiments of the invention, the Delftibactin is attached to an antimicrobial agent.

According to some embodiments of the invention, the antimicrobial agent comprises gold or gallium.

According to some embodiments of the invention, the method comprises contacting the microbe with an antibiotic.

According to some embodiments of the invention, the Delftibactin is attached to an antimicrobial agent.

According to some embodiments of the invention, the antimicrobial agent comprises gold or gallium.

According to some embodiments of the invention, the Delfibactin has the structure as shown in FIG. 41A or 41B.

According to some embodiments of the invention, the Delftibactin has the chemical formula $C_{39}H_{68}N_{14}O_{17}$.

According to some embodiments of the invention, the Delfibactin is derived from a Delftia bacteria being of the strain *D. acidovorans* DSM-39 or SPH-1.

According to some embodiments of the invention, the antimicrobial agent is not an antifungal agent.

According to some embodiments of the invention, the antimicrobial agent is greater than 1 kDa.

According to some embodiments of the invention, the at least one antimicrobial agent comprises more than 20% of the total *Delftia* components in the preparation.

According to some embodiments of the invention, the method comprises testing the activity of the antimicrobial agent.

According to some embodiments of the invention, the conditions comprise culturing at about 30° C. or less.

According to some embodiments of the invention, the medium comprises phthalic acid.

According to some embodiments of the invention, the purifying is effected by size exclusion.

According to some embodiments of the invention, the purifying is effected using reverse phase column chromatography.

According to some embodiments of the invention, the purifying comprises eluting the microbial agent with 0-80% or 10-90% acetonitrile gradient from a C18 column.

According to some embodiments of the invention, the eluting is effected in the presence of ammonium formate and TFA.

According to some embodiments of the invention, the antimicrobial agent is an antibacterial agent.

According to some embodiments of the invention, the antibacterial agent is bactericidal towards at least one of the bacteria selected from the group consisting of *E. coli, Pseudomonas aeruginosa, Klebsiella pneumonia, Acinetobacter baumannii, Enterococcus faecalis*, methicillin resistant *Staphylococcus aureus, Salmonella enteritidis* and *Serratia marcescens*.

According to some embodiments of the invention, the strain of the *Delftia* bacteria is T-7.

According to some embodiments of the invention, the strain of the *Delftia* bacteria comprises a genome having a polynucleotide sequence at least 90% homologous to the polynucleotide sequence filed under the Accession no. ERS1087230, SAMEA3900096-DT123; ERS1087231, SAMEA3900097-DT2361; ERS1087229, SAMEA3900095-DT122; ERS1087228, SAMEA3900094-DT120; ERS1087227, SAMEA3900093-DT119; ERS1087226 SAMEA3900092-DT75; or ERS1090440, SAMEA3903306-Delftia strain 2189.

According to some embodiments of the invention, the *Delftia* bacteria comprises a genome having a polynucleotide sequence at least 90% homologous to the polynucleotide sequence filed under the Accession no. ERS1087230, SAMEA3900096-DT123; ERS1087231, SAMEA3900097-DT2361; ERS1087229, SAMEA3900095-DT122; ERS1087228, SAMEA3900094-DT120; ERS1087227, SAMEA3900093-DT119; ERS1087226 SAMEA3900092-DT75; or ERS1090440, SAMEA3903306-Delftia strain 2189.

According to some embodiments of the invention, the antimicrobial agent is between 1000-3000 Daltons.

According to some embodiments of the invention, the antimicrobial agent is less than 1000 Daltons.

According to some embodiments of the invention, the composition of matter further comprises a pharmaceutically acceptable carrier.

According to some embodiments of the invention, the infection is a bacterial infection.

According to some embodiments of the invention, the bacterial infection is selected from the group consisting of a *Pseudomonas* infection, a *Klebsiella* infection, an *E. coli* infection, *Acinetobacter baumannii*, a *staphylococcus* infection and an *Enterococcus* infection.

According to some embodiments of the invention, the contacting is effected in vivo.

According to some embodiments of the invention, the contacting is effected ex vivo.

According to some embodiments of the invention, the microbe comprises a bacteria.

According to some embodiments of the invention, the culture medium further comprises agar.

According to some embodiments of the invention, the culture medium further comprises antibiotics.

According to some embodiments of the invention, the culture medium is sterile.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

The patent or application file contains at least one drawing executed in color. Copies of this patent or patent application publication with color drawing(s) will be provided by the Office upon request and payment of the necessary fee.

In the drawings:

Figure 1C:
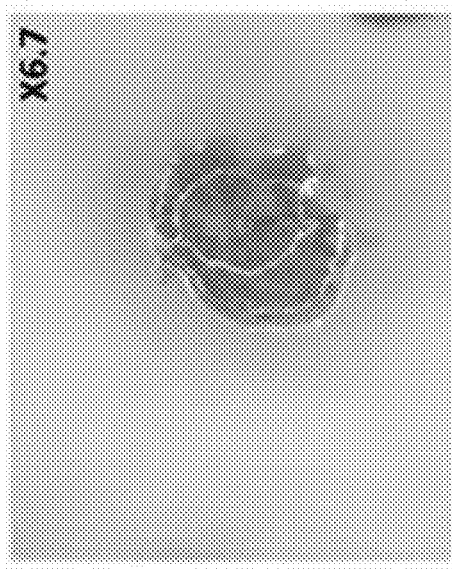
Figure 1B:
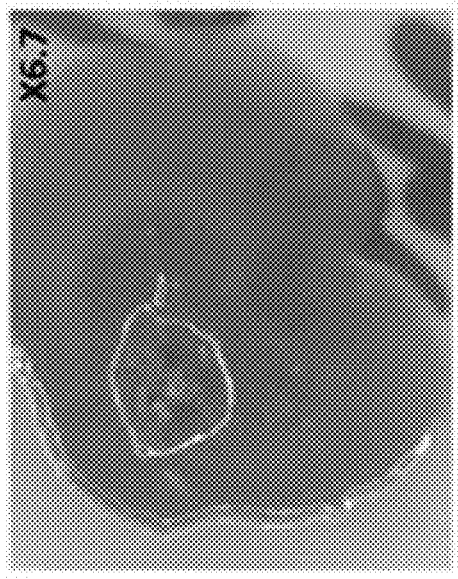
Figure 1A:
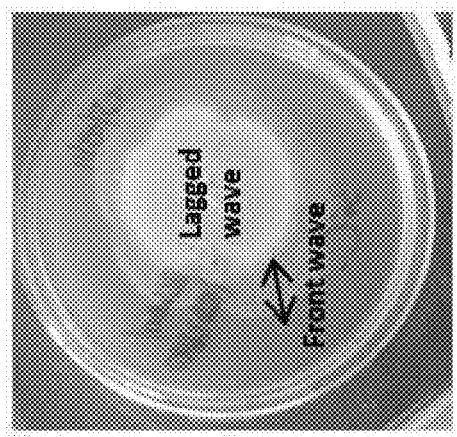

FIGS. 1A-C are photographs illustrating penetration of *Delftia* strain 75 into a colony of *E. coli* expressing mcherry. FIG. 1A illustrates typical swarming behavior of *Delftia* on swarm agar. FIG. 1B illustrates a swarm agar comprising *E. coli* which was inoculated 2 cm apart from *Delftia* strain 75. FIG. 1C illustrates a swarm agar comprising *E. coli* which was inoculated 1 cm apart from *Delftia* strain 75.

Figure 2A:
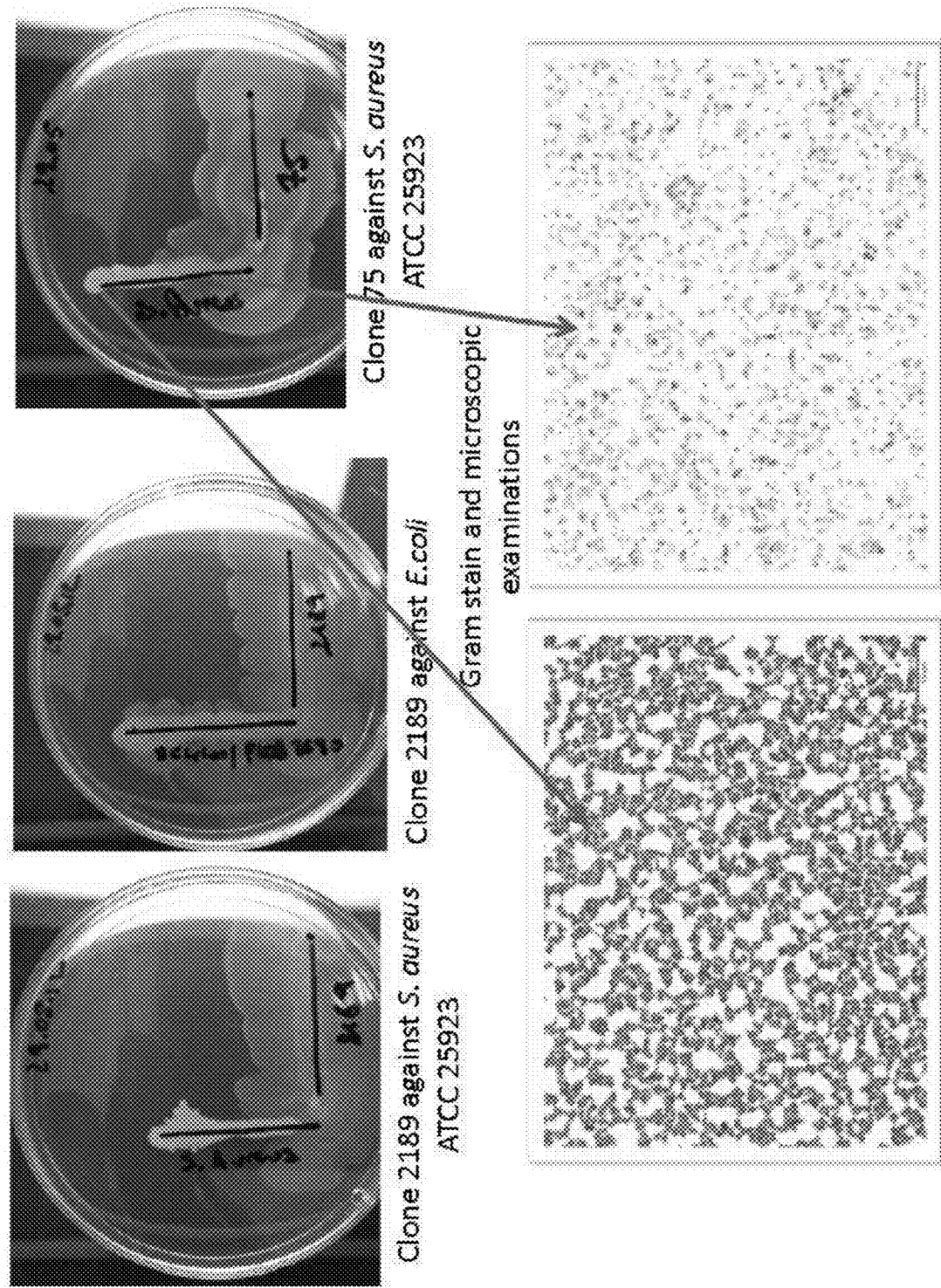
Figure 2B:
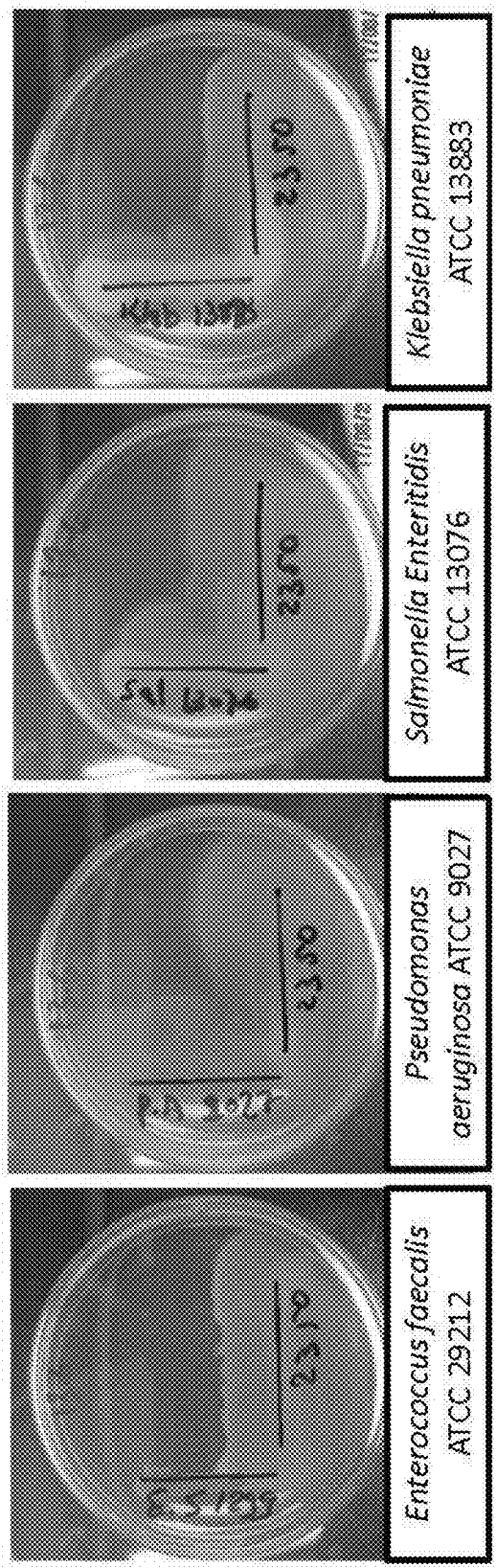

FIGS. 2A-B are photographs illustrating predataxis of *D. tsuruhatensis* against *S. Aureus* and *E. coli* (FIG. 2A); and *Enterococcus faecalis, Pseudomonas aeruginosa, Salmonella Enteritidis*, and *Klebsiella pneumonia* (FIG. 2B).

Figure 3B:
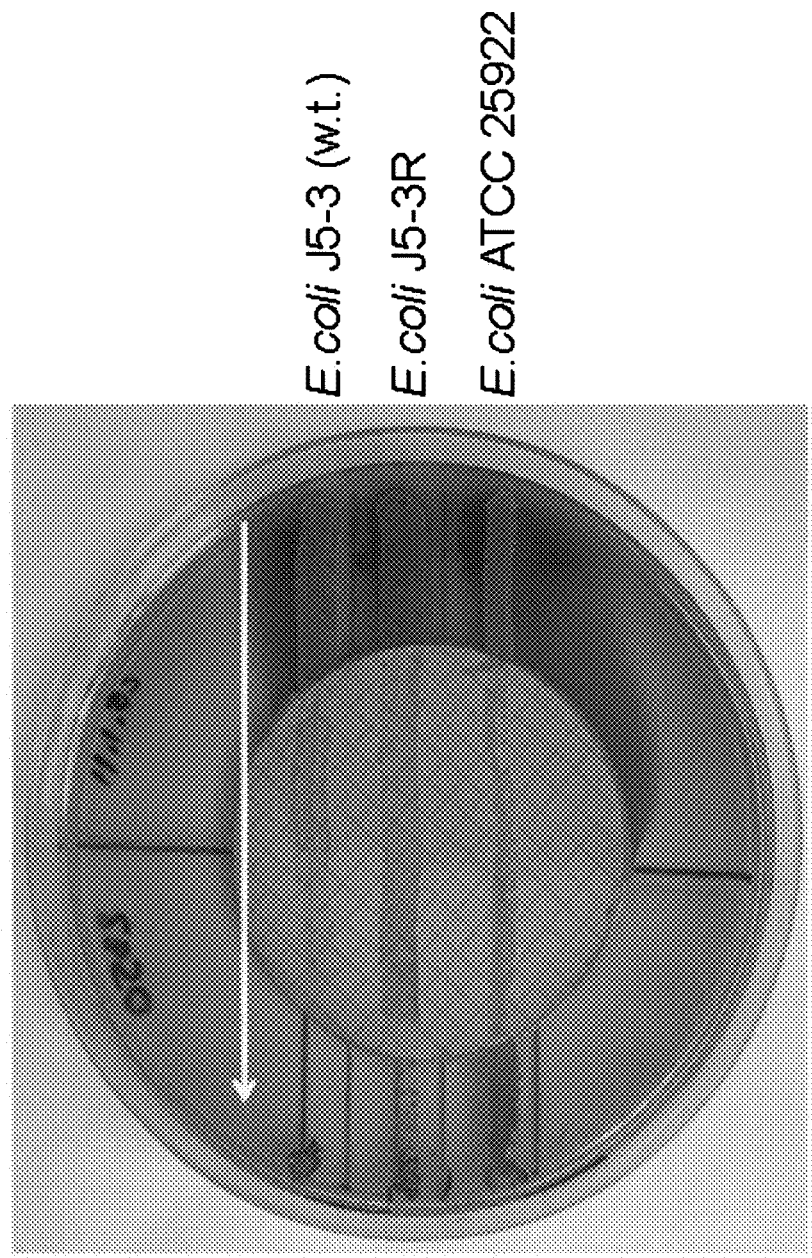

FIGS. 3A-B illustrate that the inhibitory effect of *Delftia* sp. against target cells is mediated by secretion of toxic compounds as well as by contact dependent inhibition. FIG. 3A is a graph illustrating that supernatant from strain 2189 reduces the amount of *S. aureus* MRSA whereas nutrient broth (NB) does not. FIG. 3B is a photograph of a culture dish on which one half of the plate was inoculated with *Delftia* sp. Strain 2189. A 0.45 μm filtration membrane placed over the plate and various *E. coli* strains were spread using a cotton swab in the direction of the white arrow. Partial inhibition was observed over the membrane that covers strain 2350. Complete inhibition was observed by direct contact of sensitive *E. coli* J5-3 with strain 2350. *E. coli* strain J5-3R that is partial resistant to strain 2350 was selected by repeated exposure to strain 2350 and recovery of survivors' colony.

Figure 4A:
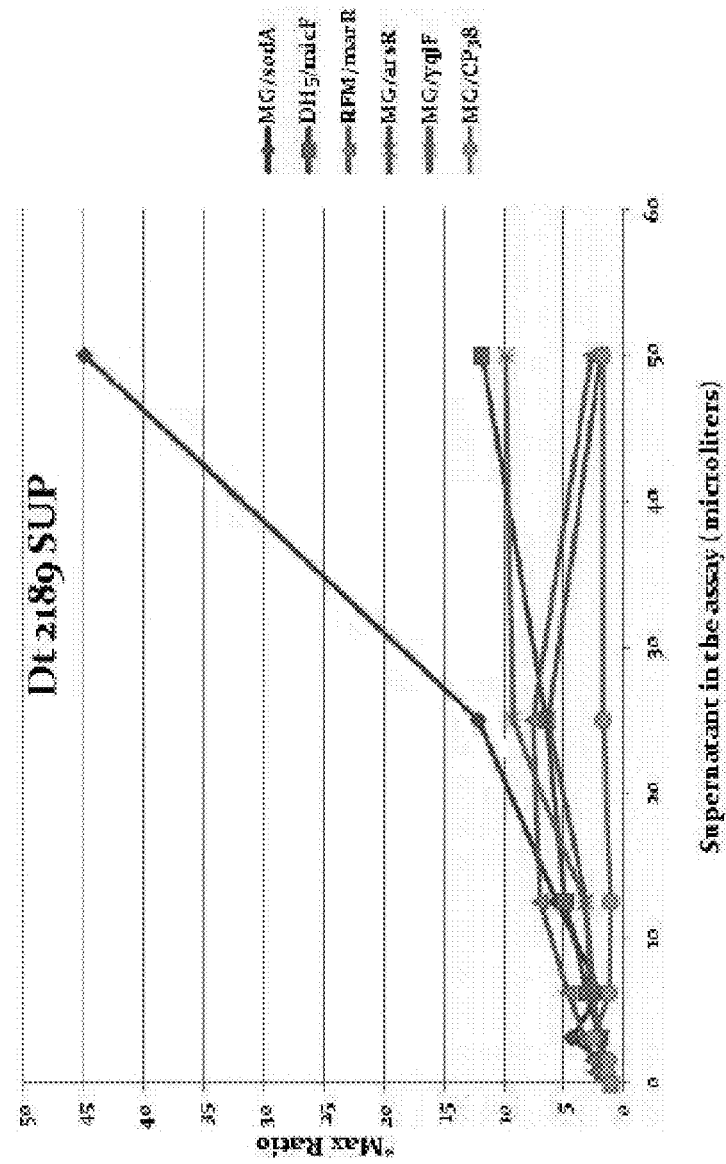
Figure 4B:
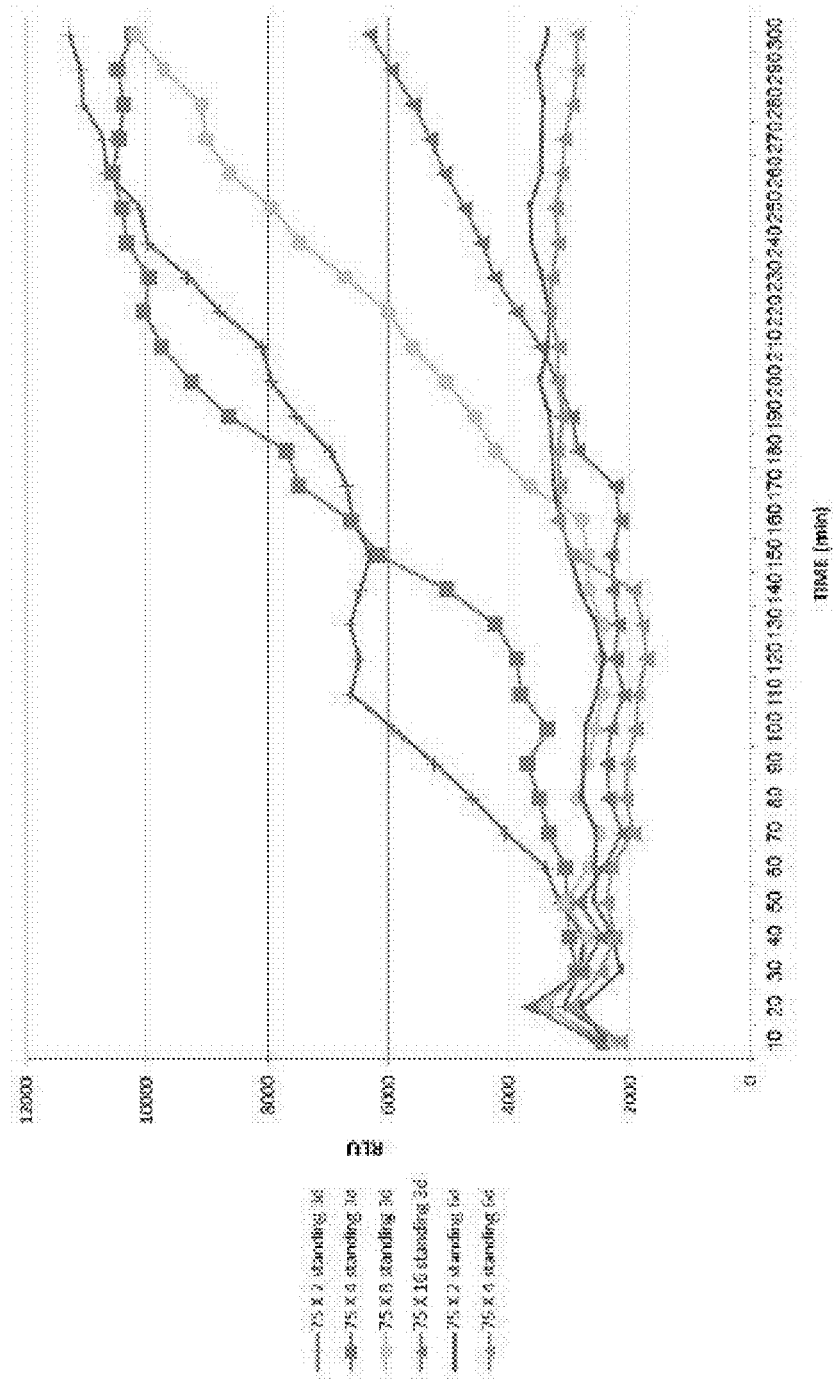

FIGS. 4A-B illustrate the utilization of the *E. coli* biosensor array for measuring toxic activity in *Delftia* supernatant. FIG. 4A is a graph displaying the maximal ratio of promoter activation for each volume of supernatant from *Delftia* sp. Strain 2189 (relative to the constitutive strain *E. coli* MG/CP38). FIG. 4B is a graph displaying sodA promoter activity in *E. coli* MG following addition of a clear supernatant from *Delftia* strain 75.

Figure 4D:
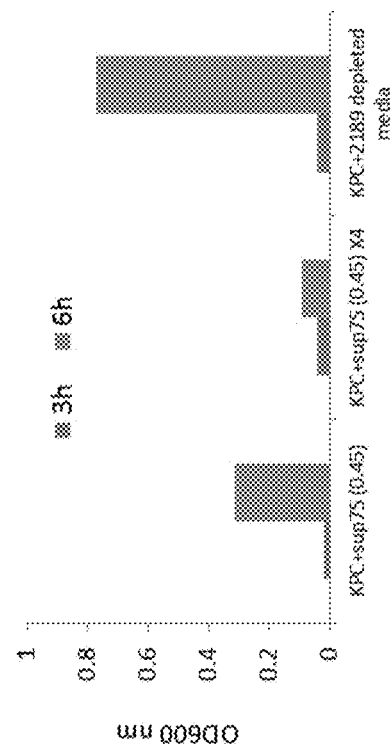
Figure 4C:
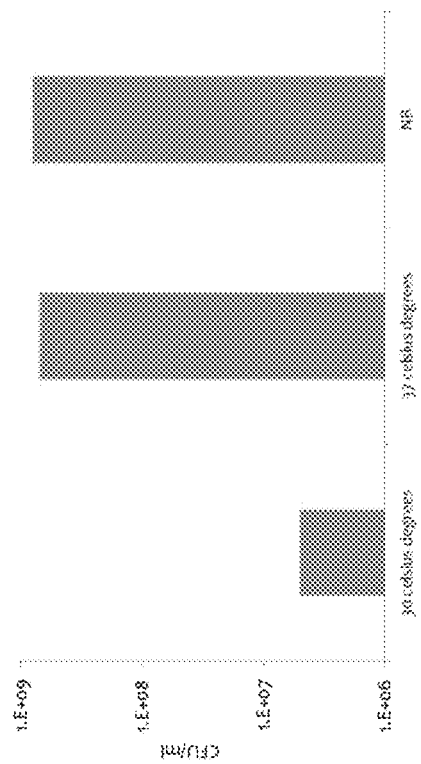

FIGS. 4C-D are graphs illustrating the temperature regulation for the production of antimicrobial compounds against different challenging clinical isolates. 4C. The target bacteria is *Acinetobacter baumanii*. Viable counts of *Acinetobacter baumanii* were measured after 6 hours of incubation with supernatants from *Delftia* strain 2189. 4D The target bacteria KPC is inhibited by supernatant from strain 75. KPC proliferation is measured in OD600 nm. The inhibitory effect is increased after 4 fold concentration of the supernatant. *Delftia* grown in 37° C.-depleted media has no inhibitory effect.

Figure 5A:
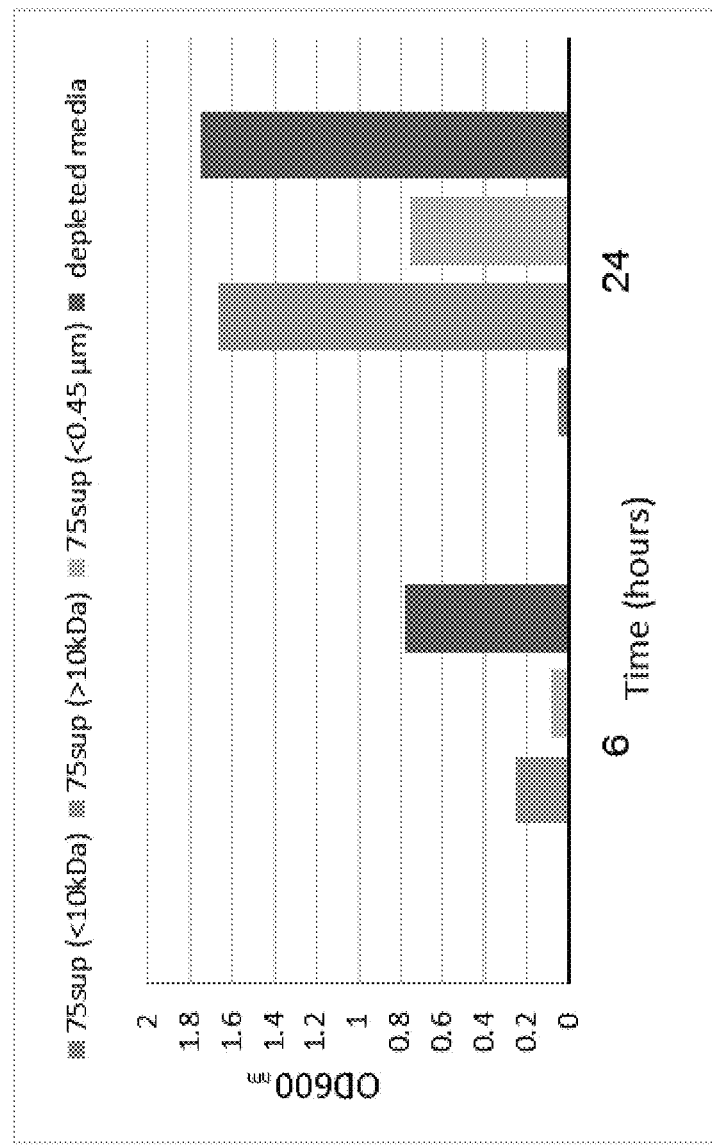
Figure 5D:
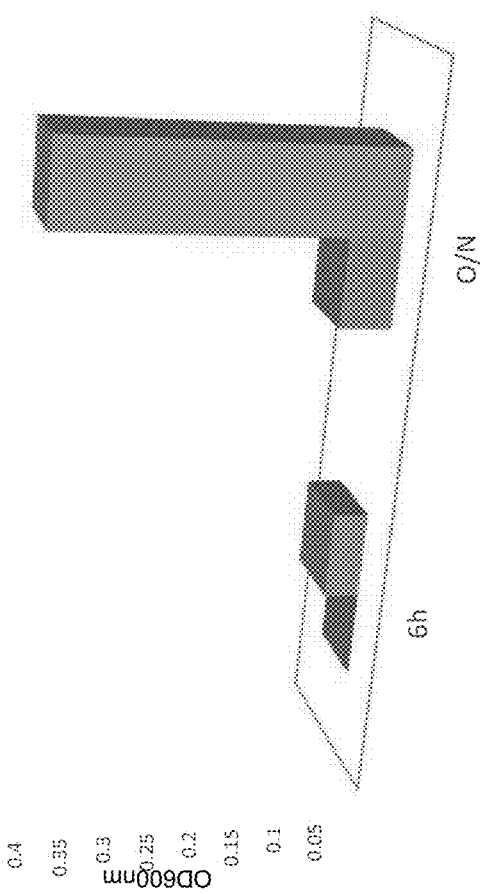
Figure 5E:
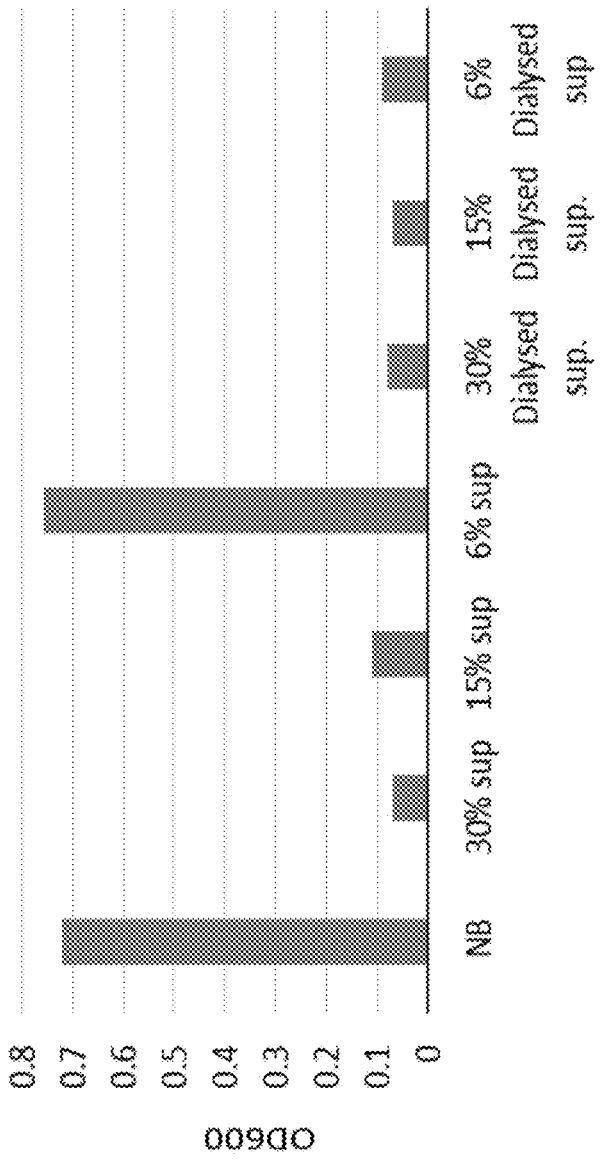

FIGS. 5A-E are graphs illustrating the size of the active compounds. FIGS. 5A-B illustrate the activity of Delftia fractions following uploading on to a 10-kDa Amicon filter. FIGS. 5C-D illustrate the activity of Delftia fractions following uploading on to a 3-kDa Amicon filter. FIG. 5E illustrates the activity of Delftia fractions following uploading on to a 1-kDa Amicon filter. Target MRSA USA300 (FIGS. 5A, 5C, 5E), *Acinetobacter baumanii* (FIG. 5B) or Vancomycin resistant *Enterococcus* (VRE; FIG. 5D) was diluted to 0.1 $OD_{600}$ nm and further diluted in NB 1:100. 330 μl of various size fractions of strain 75 was added to 660 μl of diluted bacteria in 50 ml test tube. The cultures were incubated whilst shaking at 37° C. At the indicated time points, the $OD_{600}$ of the culture was measured. Depleted media refers to a negative control which is devoid of *Delftia* bacteria.

Figure 6:
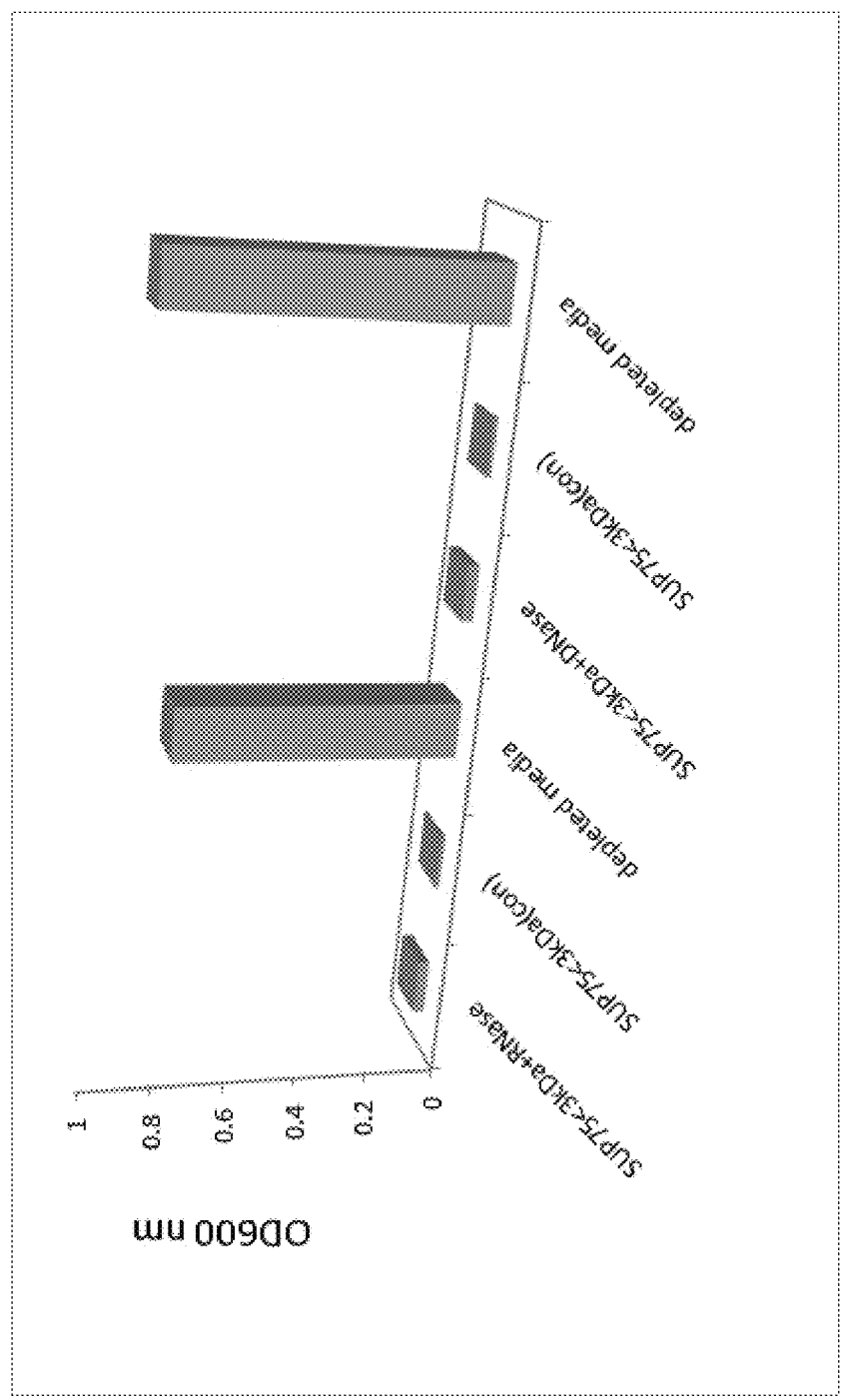

FIG. 6 is a bar graph illustrating the active agent in the supernatant of *Delftia* bacteria is not sensitive to DNAse I or RNAse A.

Figure 7:
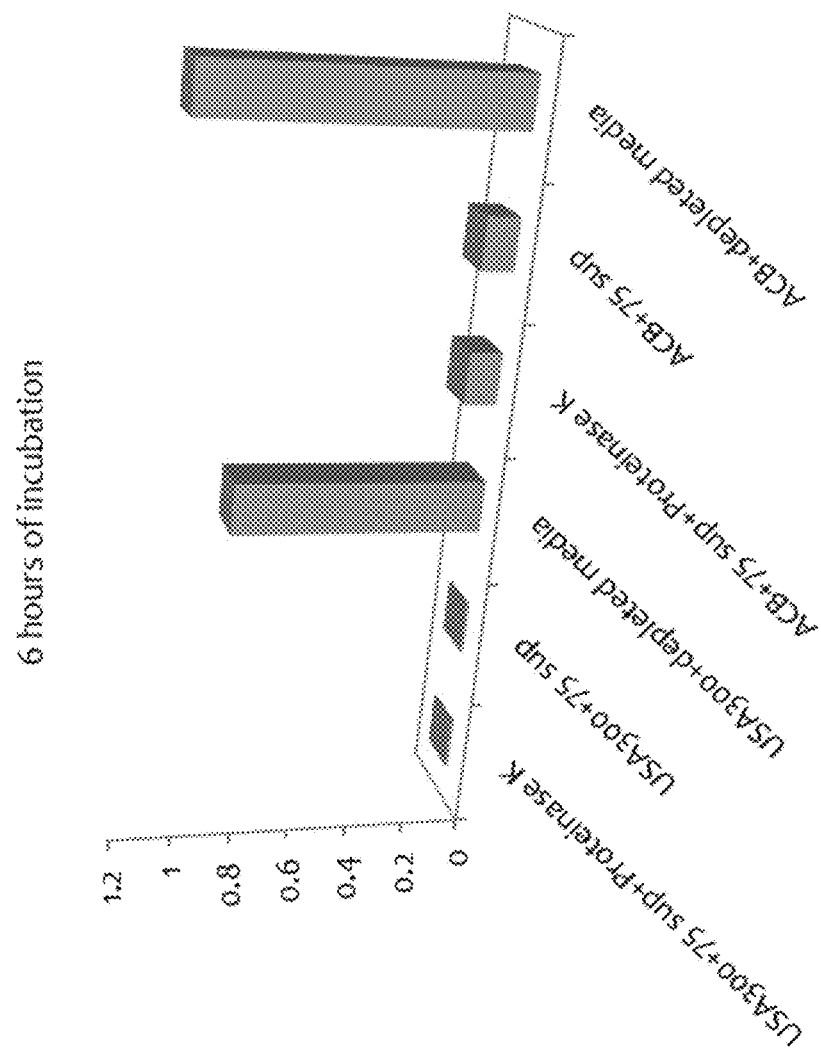

FIG. 7 is a bar graph illustrating the active agent in the supernatant of *Delftia* bacteria is not sensitive to proteinase K.

Figure 8:
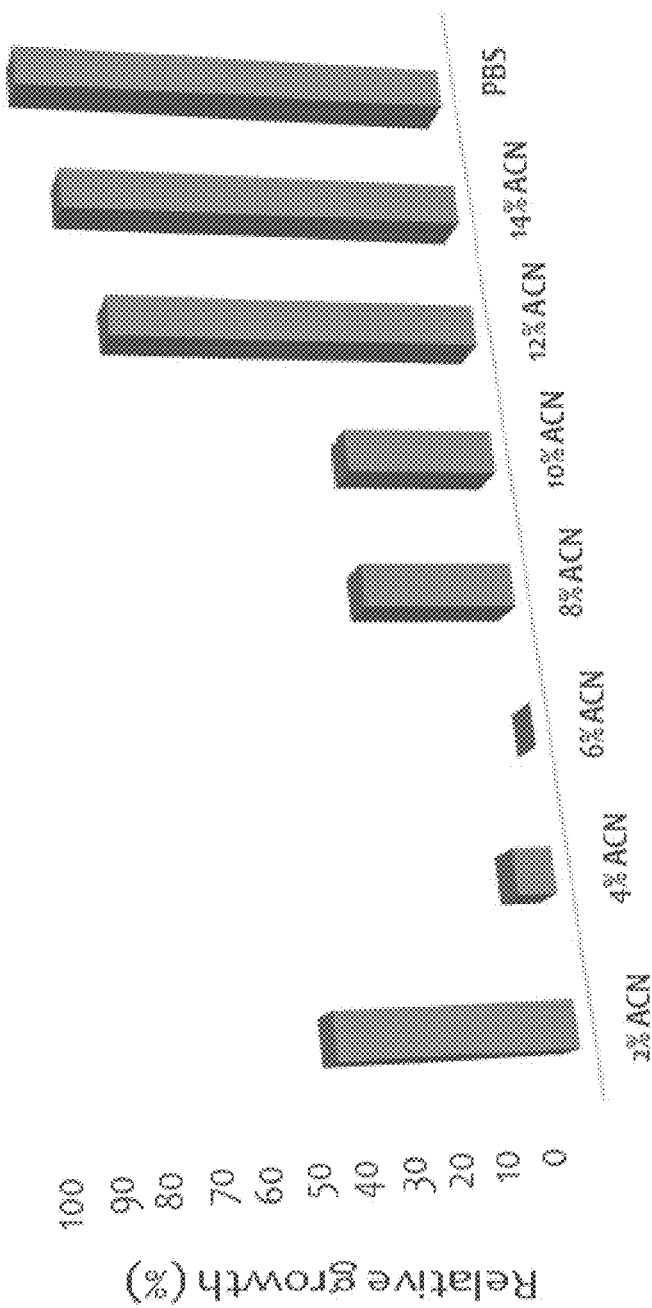

FIG. 8 is a graph illustrating that most of the activity of the *Delftia* bacteria supernatant elutes off a Sep-Pak tC18 column at 6% acenitrile.

Figure 9B:
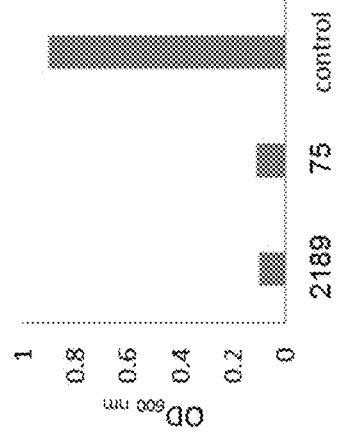
Figure 9C:
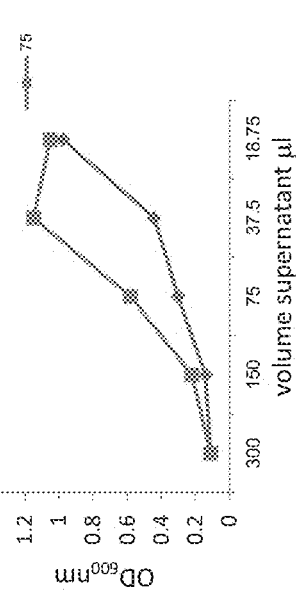
Figure 9A:

FIGS. 9A-C are graphs illustrating the antimicrobial potency of supernatants from *Delftia* strains grown in minimal defined media. A) Growth inhibition of MRSA USA300 by supernatants of clones 75 and 2189. B) Growth inhibition of *Acinertobacter baumannii* (ACB) by the same supernatants as in A. C) Dose response of antimicrobial effects of supernatants from clones 75 and 2189 against the target bacteria USA300.

Figure 10:
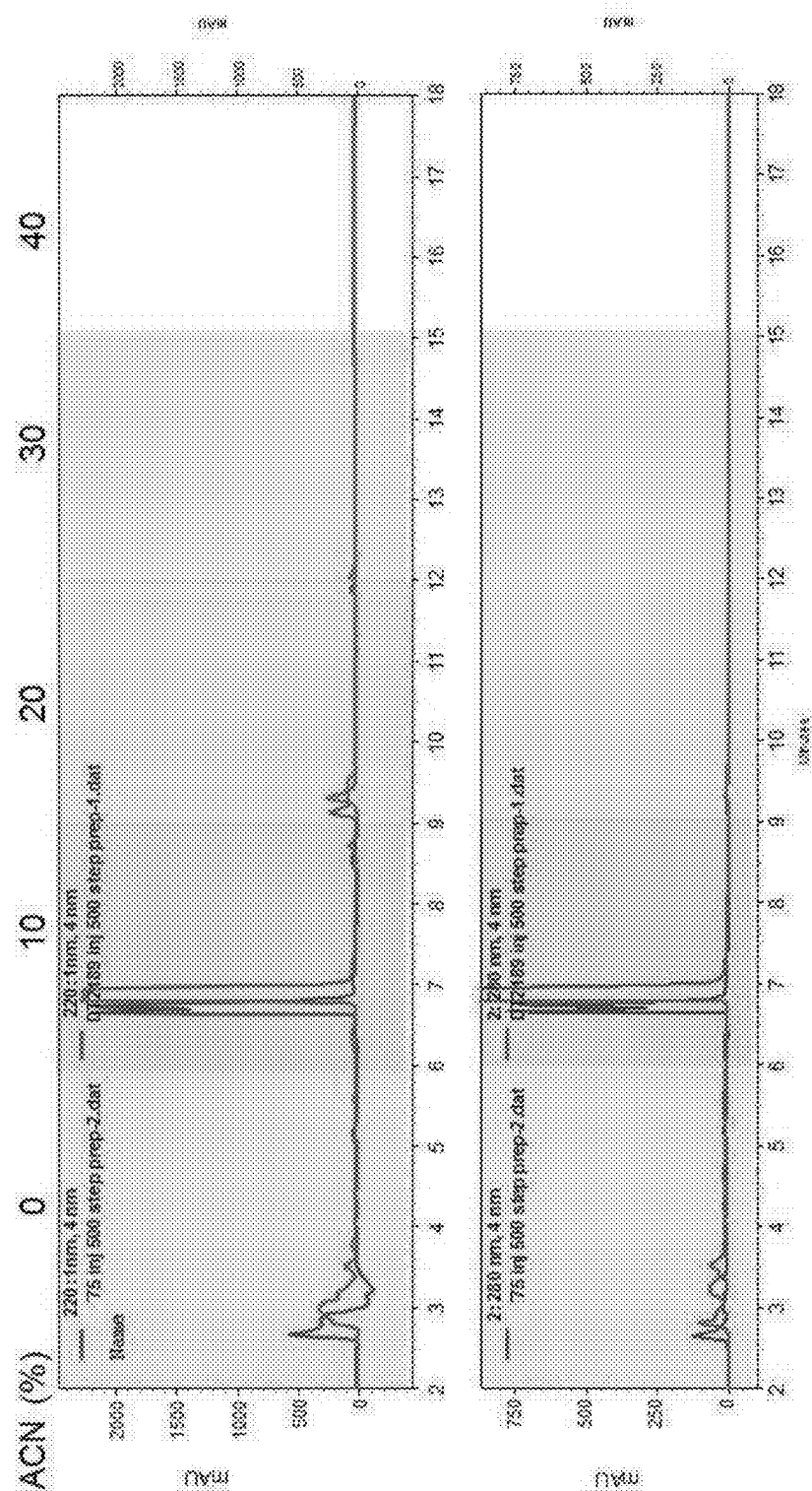

FIG. 10 illustrates the results of a chromatographic analysis of supernatant from strain 2189 and 75 incubated for 8 days in defined minimal media with 0.5% glycerol. The upper panel shows signal detection at 220 nm and the lower panel at 280 nm. The green line indicates strain 75 and the pink 2189.

Figure 11B:
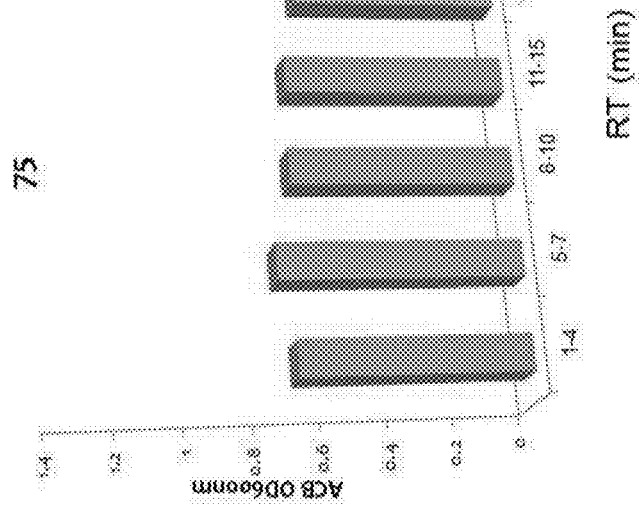
Figure 11A:
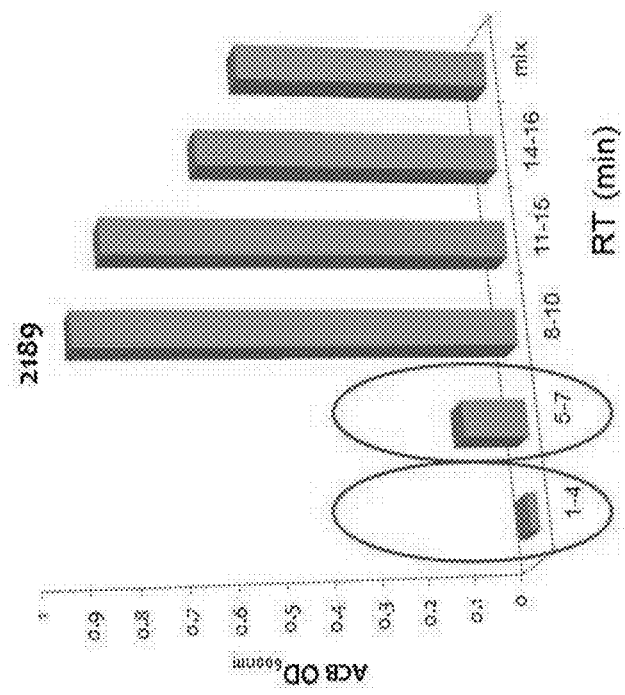
Figure 11D:
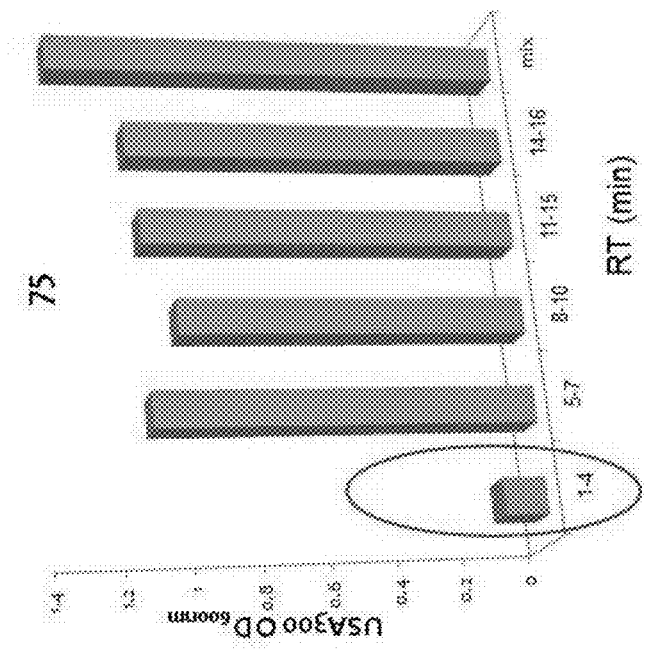
Figure 11C:
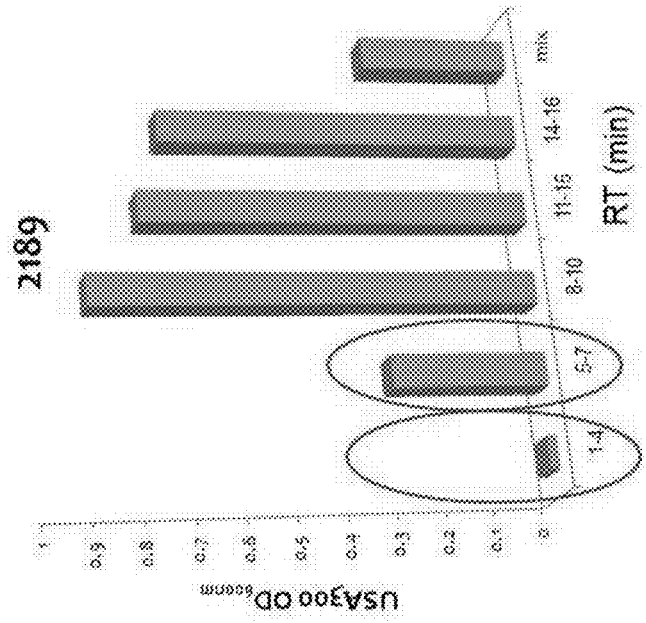

FIGS. 11A-D are graphs illustrating the antimicrobial activity in different HPLC fractions. FIGS. 11A-B display the activity of the indicated fractions against MRSA USA 300, and FIGS. 11C-D display the activity of the indicated fractions against *A. baumannii*. Mix indicates mixture of all the fractions. The ellipses mark the active fractions.

Figure 12:
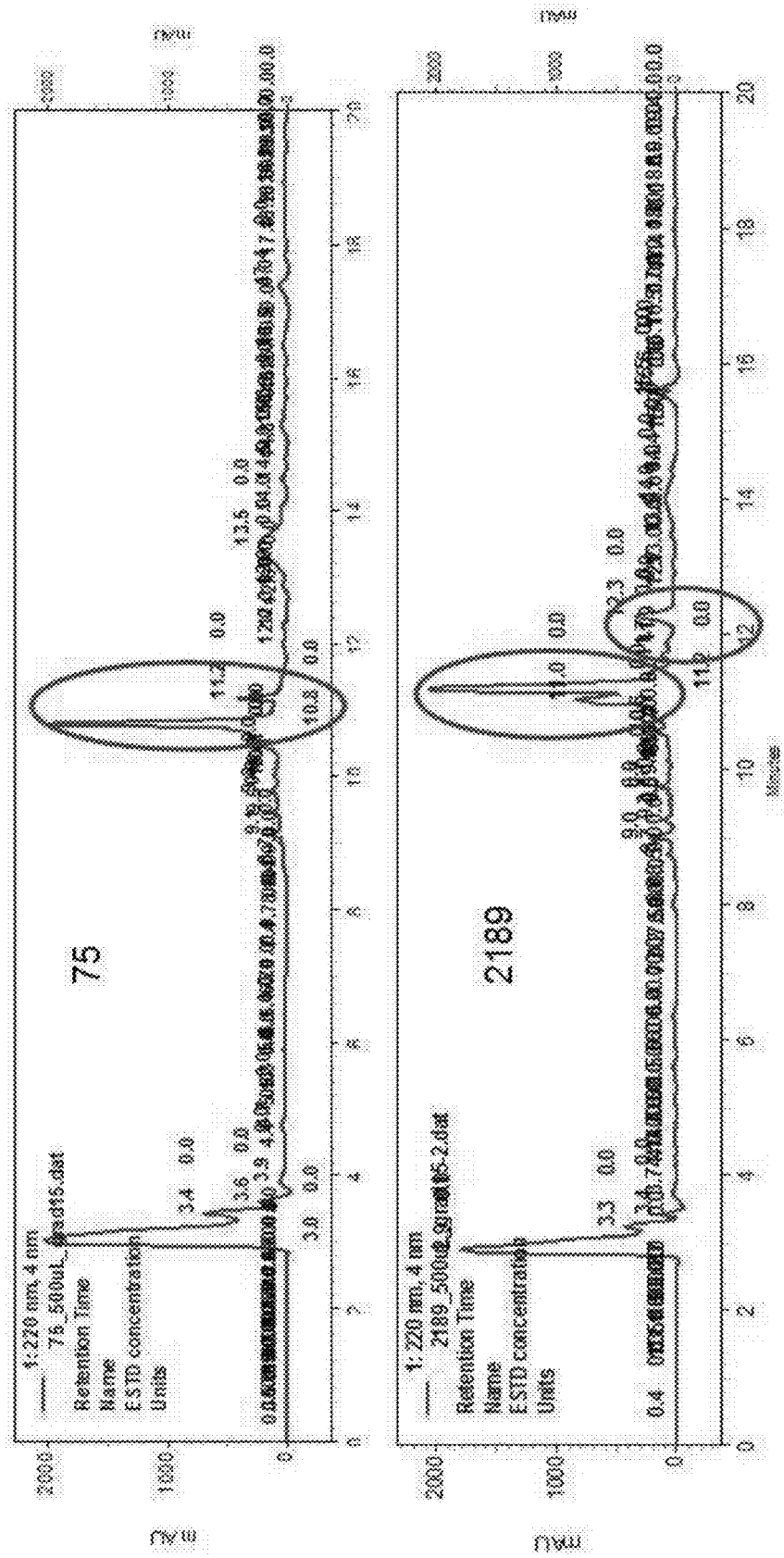
Figure 12:
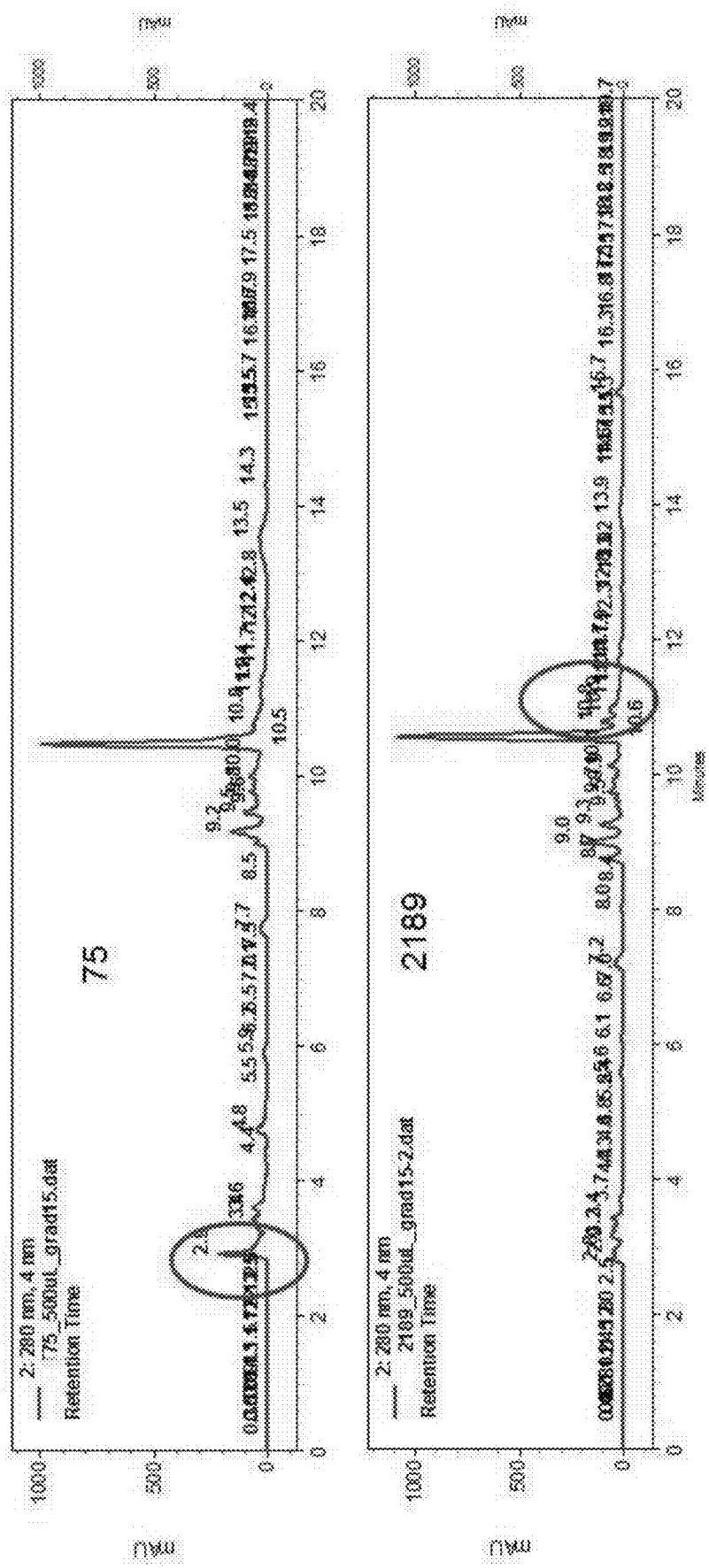

FIG. 12 illustrates the results of a chromatographic analysis of supernatant produced from *Delftia* grown for 8 days in defined minimal media. Active supernatants from *Delftia* strains 75 and 2189 which were grown on minimal defined media, were run using acetonitrile gradient (0-15%) on a preparative C18 HPLC column. Two upper panels—excitation at 220 nm and two lower panels—excitation at 280 nm. Unique peaks for each strain are marked by ellipses.

FIG. 13 is a table summarizing the peaks detected by HPLC analysis of the supernatants of strain 75 and 2189 at wave lengths 220 and 280 nm.

FIGS. 14A-D are graphs illustrating antimicrobial activity in different HPLC fractions of strain 2189 and 75. The different fractions eluted from the preparative HPLC column were tested for antimicrobial activity against USA300 and *Acinetobacter baumannii* (ACB). FIGS. 14A-B illustrate the activity of different HPLC fraction of compounds produced by strain 2189. FIGS. 14C-D illustrate the activity of HPLC fraction of strain 75. Fractions of minutes 3-4 and 11-12 from 2189 supernatant showed the highest antimicrobial activity against USA300, whereas fraction 11-12 min is the most potent fraction in 2189 supernatant against ACB, showing significant inhibition. Fraction 3-4 minute displays moderate inhibition of ACB. *Delftia* strain 75 fractions 3-4 min and 10-11 min. exhibited antimicrobial activity against USA300 and ACB. Fraction 10-11 min. exhibited higher potency against ACB than fraction 3-4.

Figure 15:
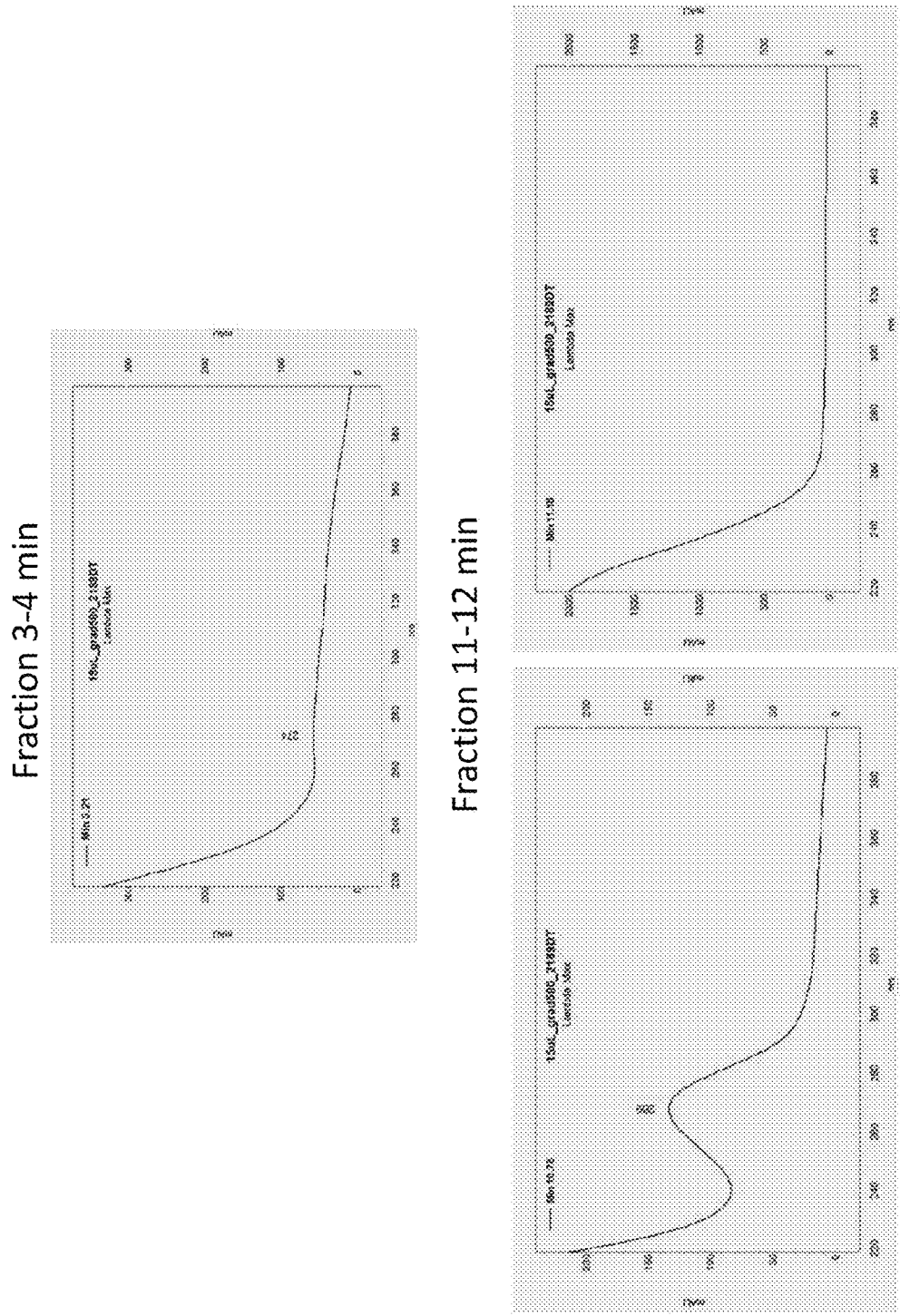

FIG. 15 provides a spectral analysis of differential active HPLC fractions from strain 2189.

FIG. 16 provides a spectral analysis of differential active HPLC fractions from strain 75.

Figure 17A:
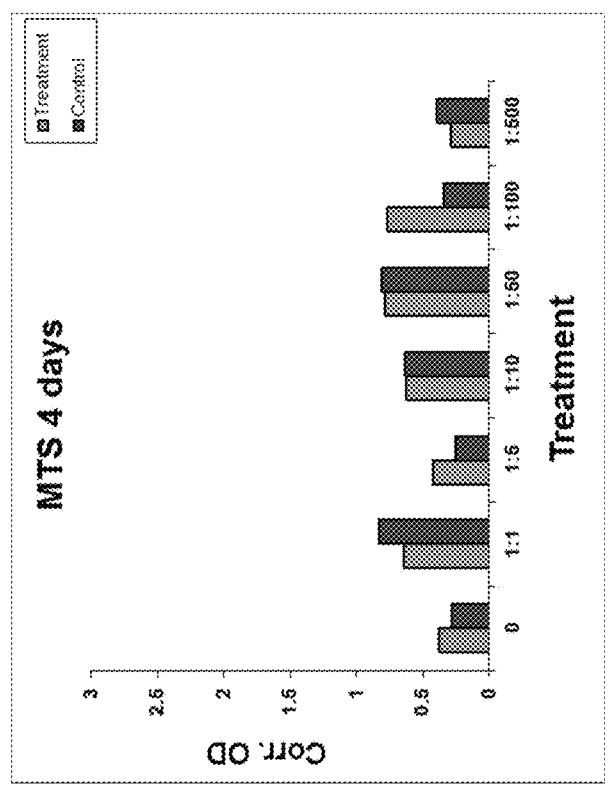
Figure 17B:
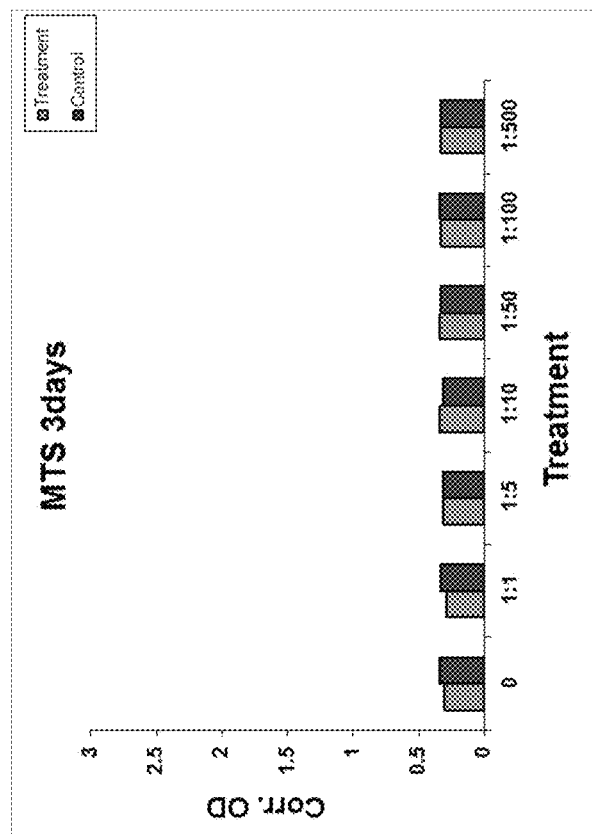

FIGS. 17A-B are graphs illustrating the results of viability assays on primary human kidney cells. Graphs summarize the experiments after exposure of the cells for 3 days (FIG. 17A), and 4 days (FIG. 17B).

Figure 18:
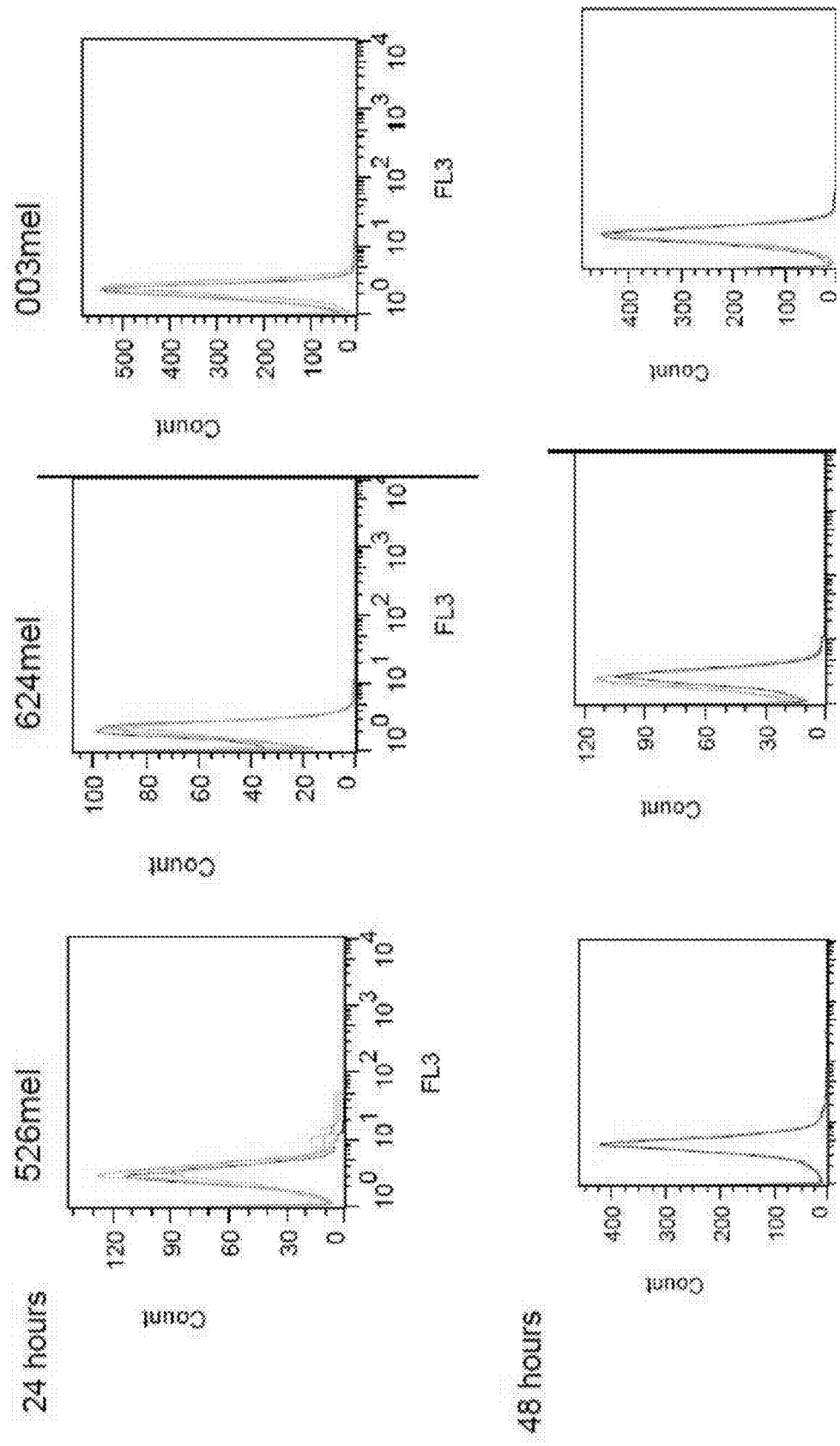

FIG. 18 is graphs illustrating that the *Delftia* supernatant has no inhibitory effect against human melanoma cells, as measured by FACS. Negative control (black)—5 µl of the Blank solution. Positive control—UV treatment.

Figure 19B:
Figure 19A:
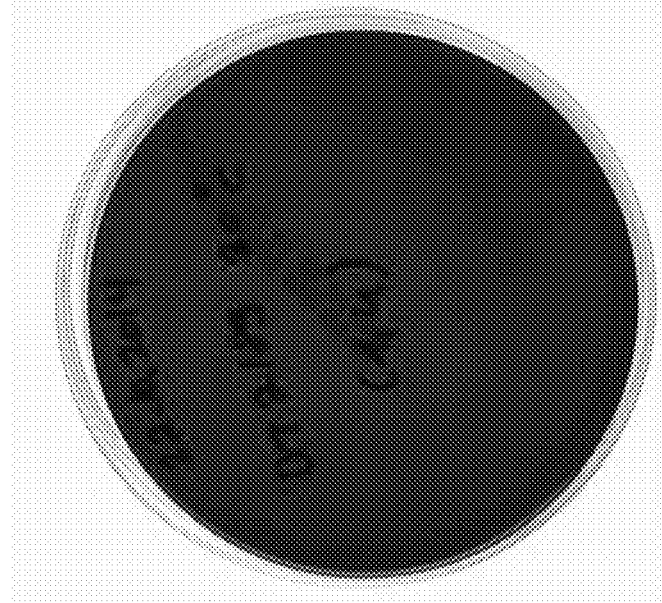

FIGS. 19A-B are photographs illustrating the results of the analysis of hemolysis effect of *Delftia* clone 2189 on sheep red blood cells: Direct plating of *Delftia* clone 2189 on sheep blood agar showed no hemolytic effect (FIG. 19A). As a positive control for hemolysis, Staph. *aureus* strain USA 300 was also plated on sheep blood agar (FIG. 19B).

Figure 20:
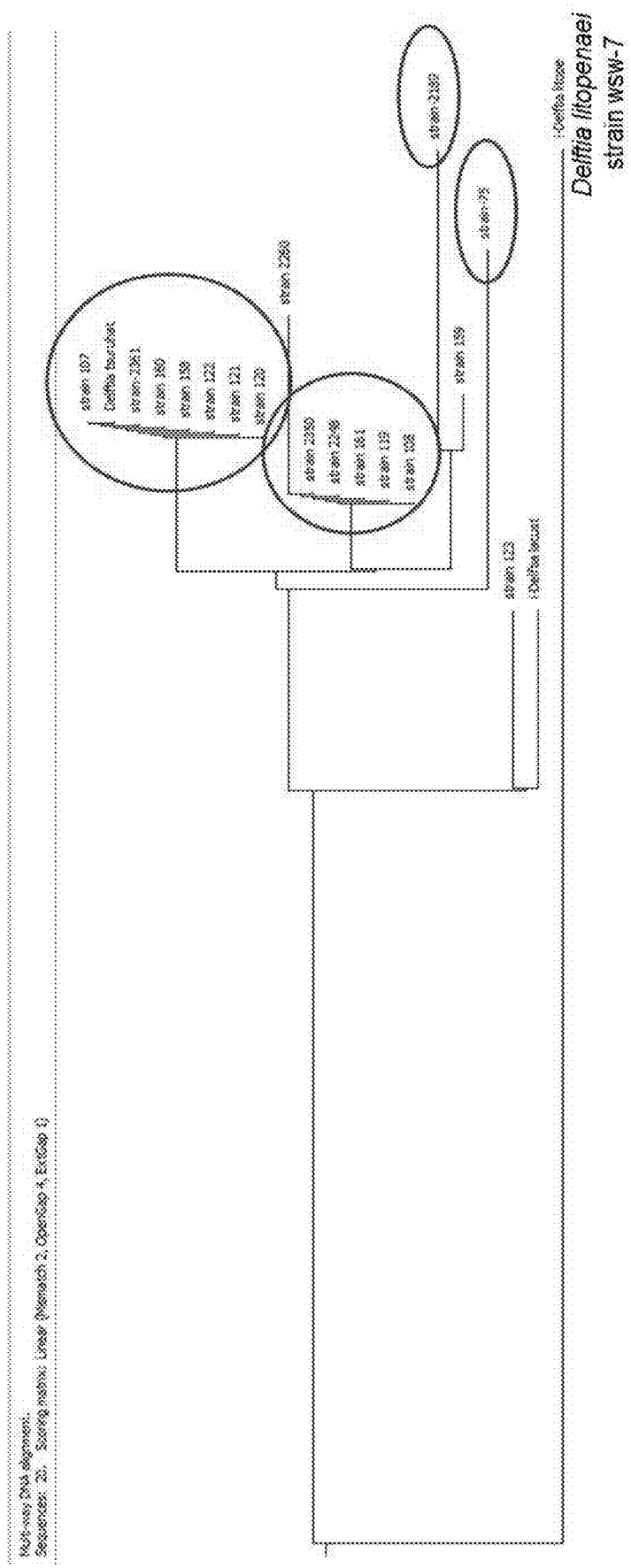
Figure 22A:
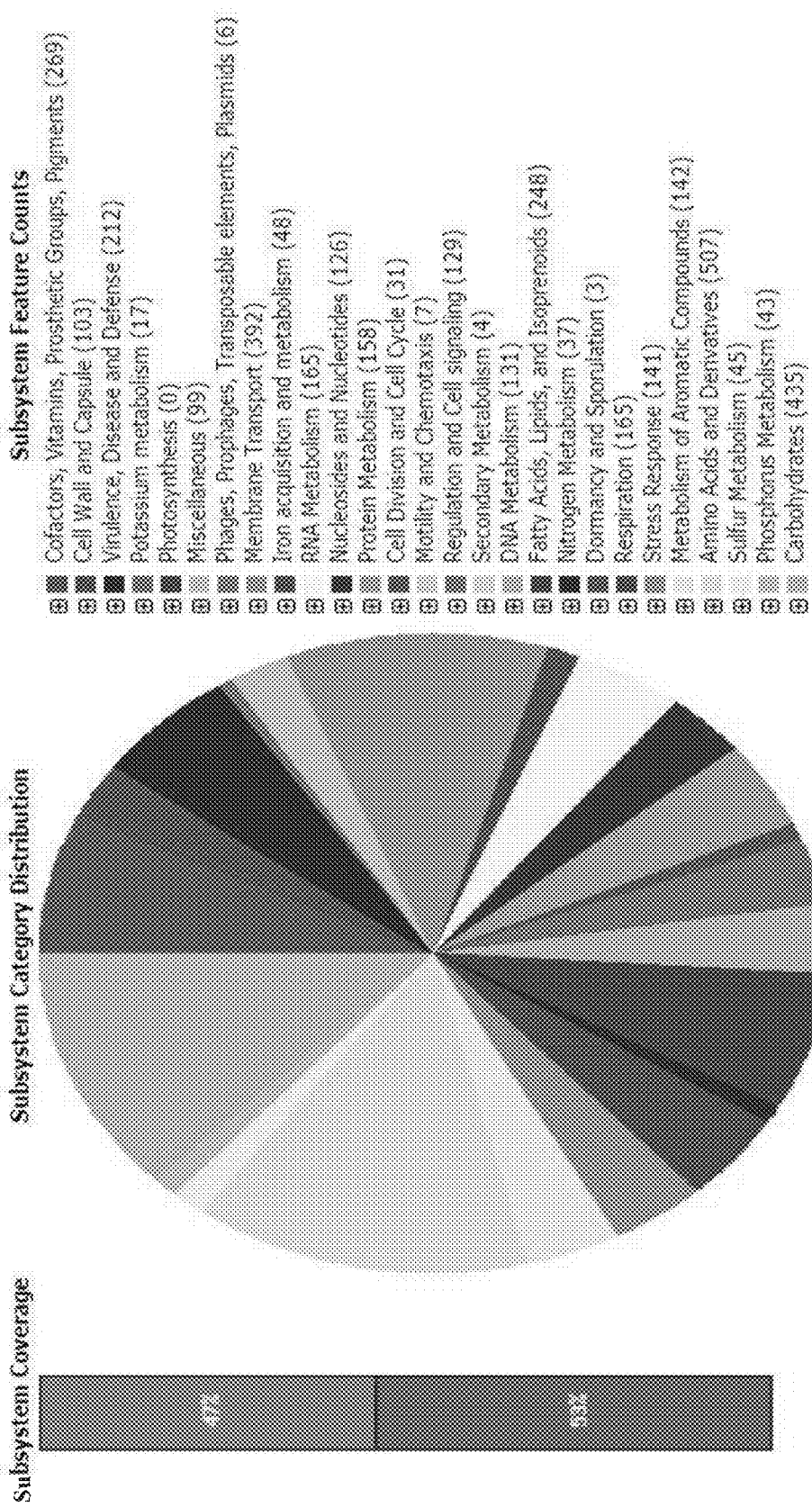
Figure 22B:
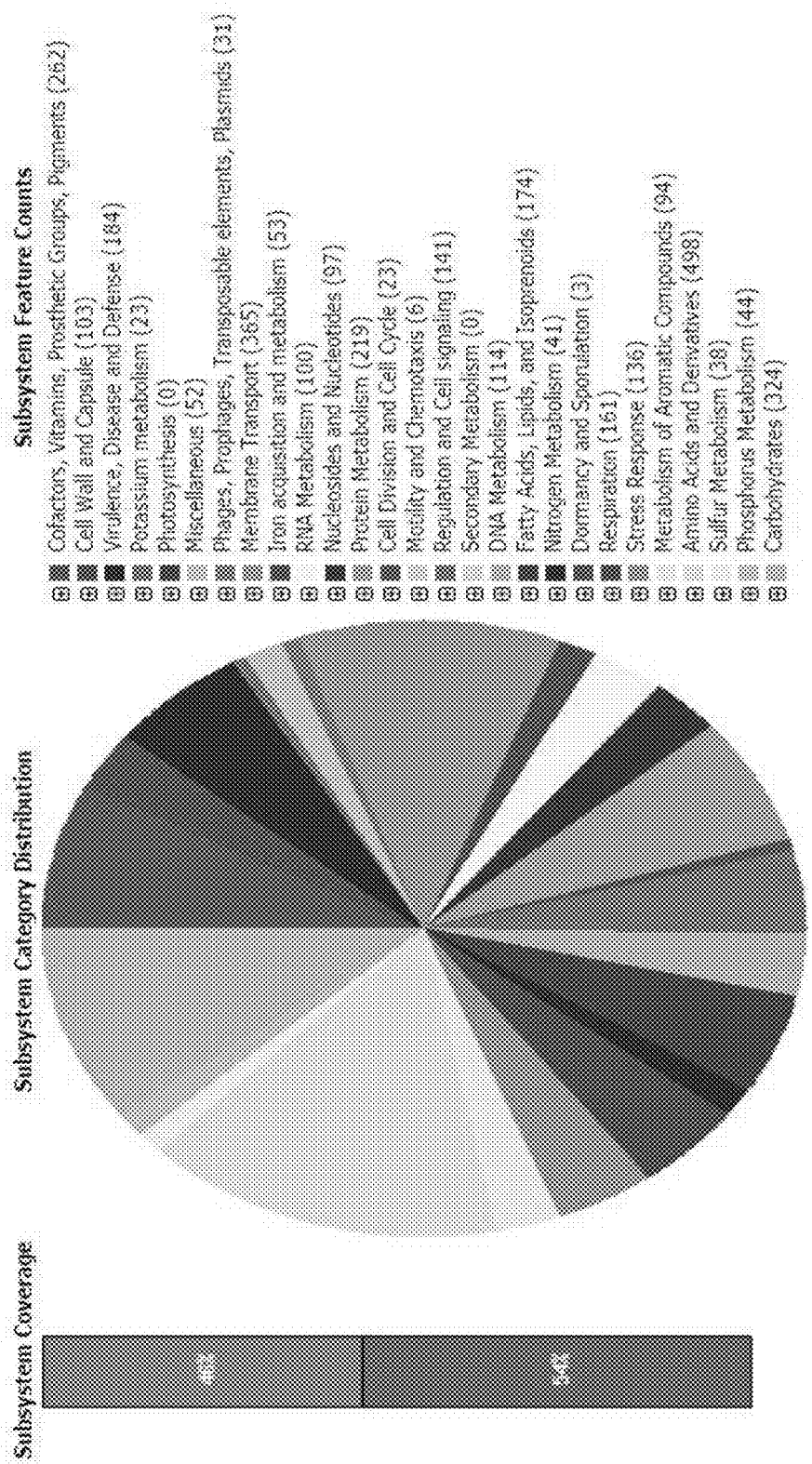
Figure 22C:
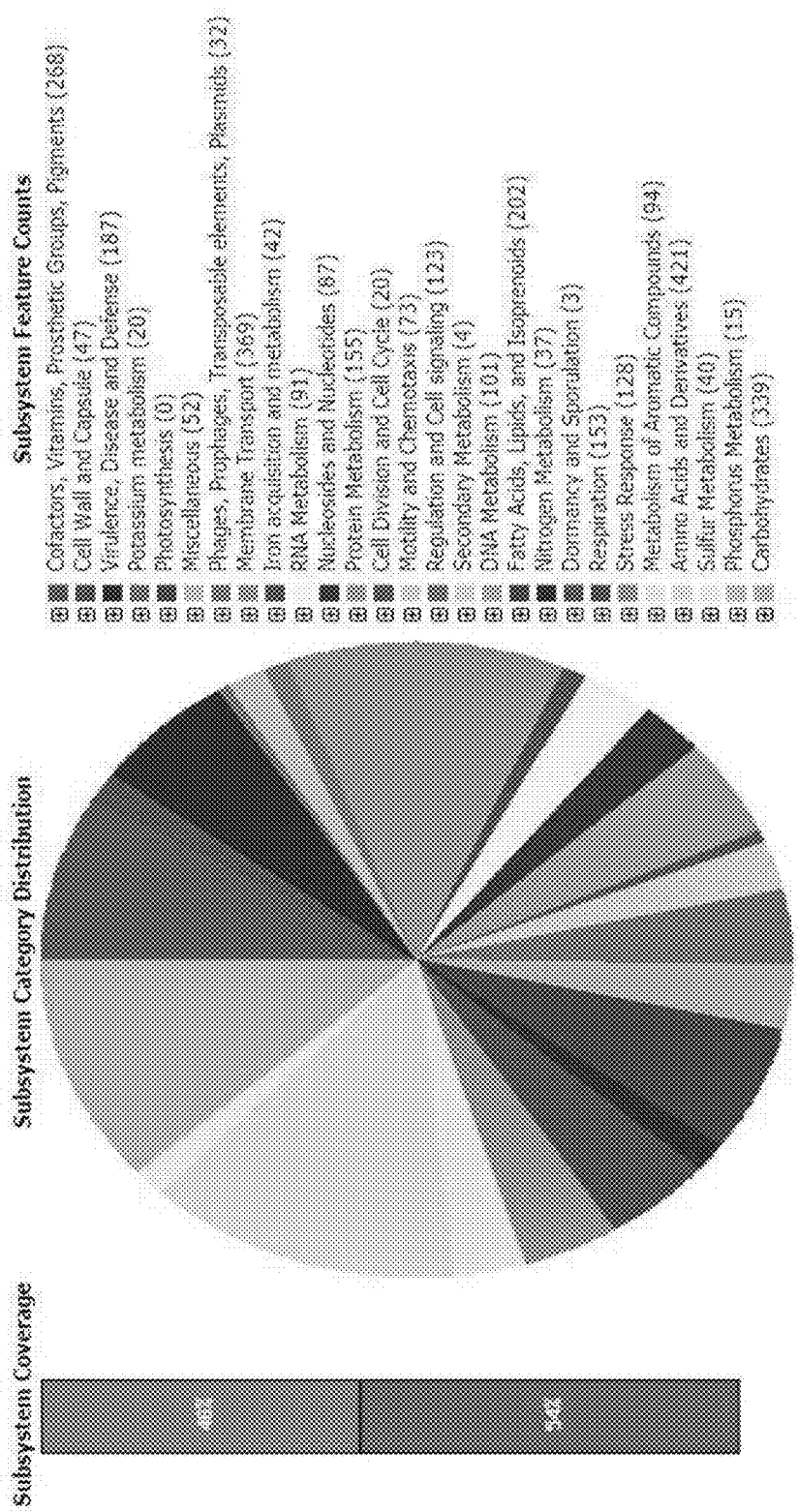
Figure 22D:
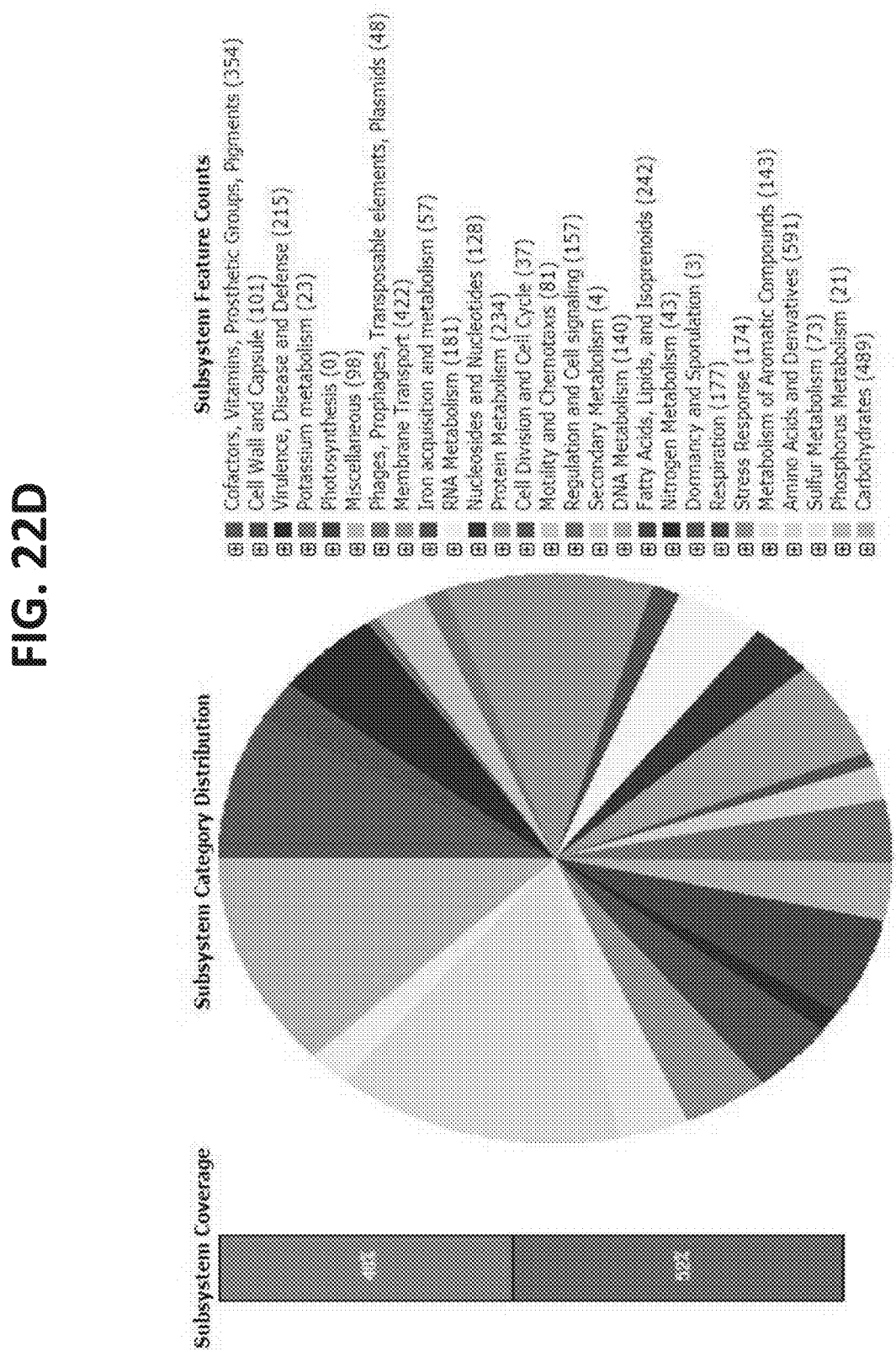
Figure 22E:
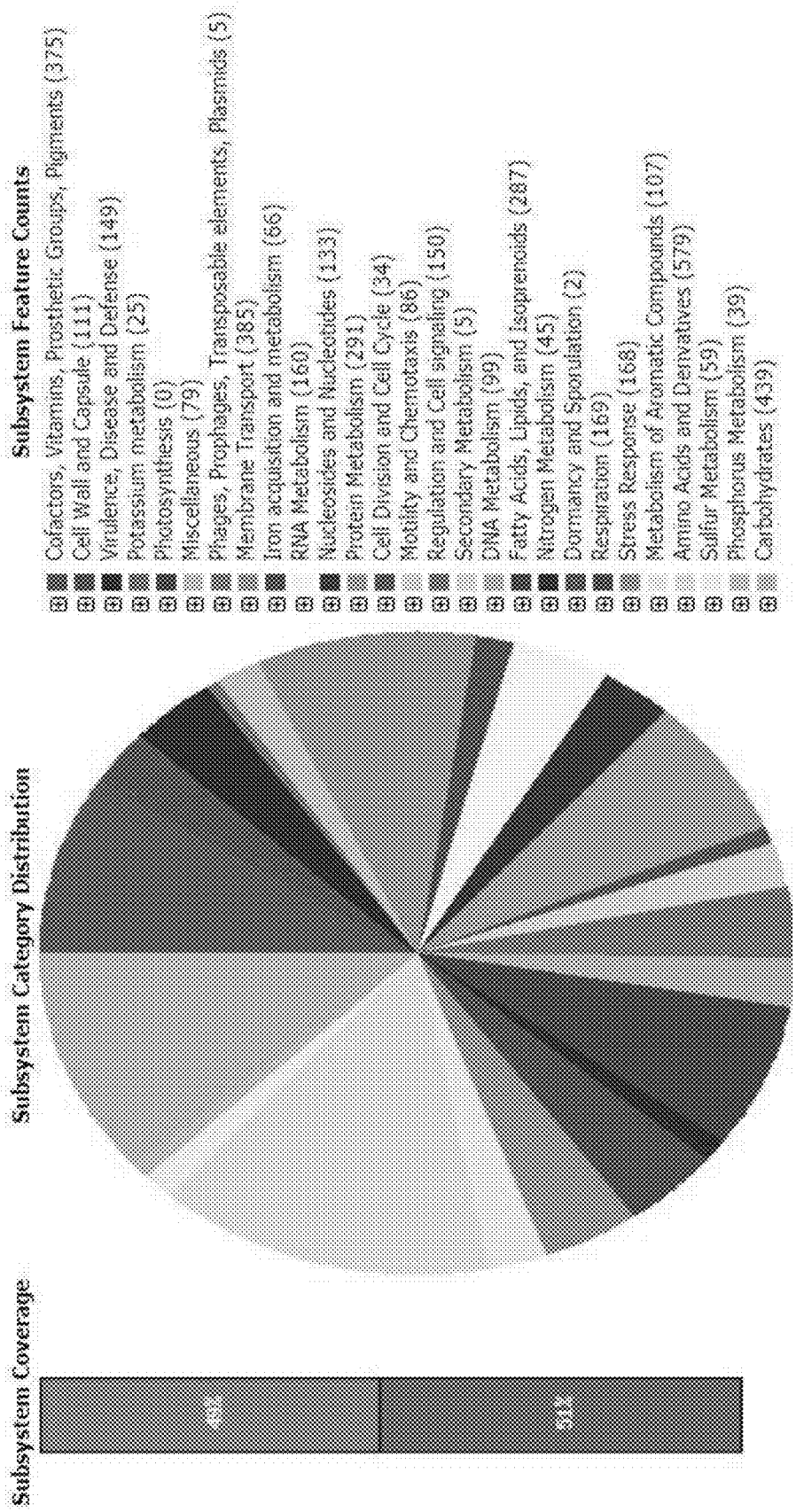
Figure 22F:
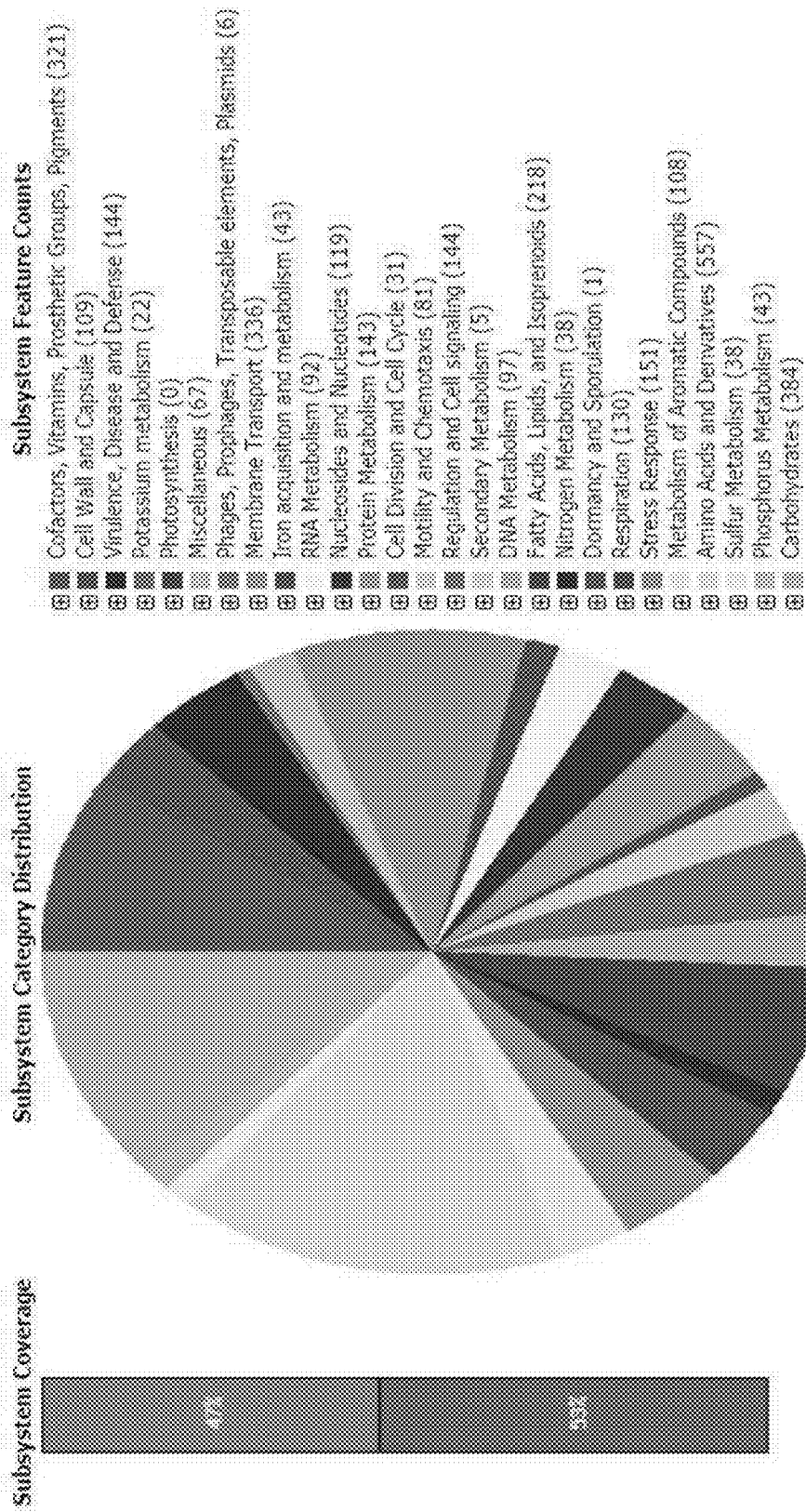
Figure 22G:
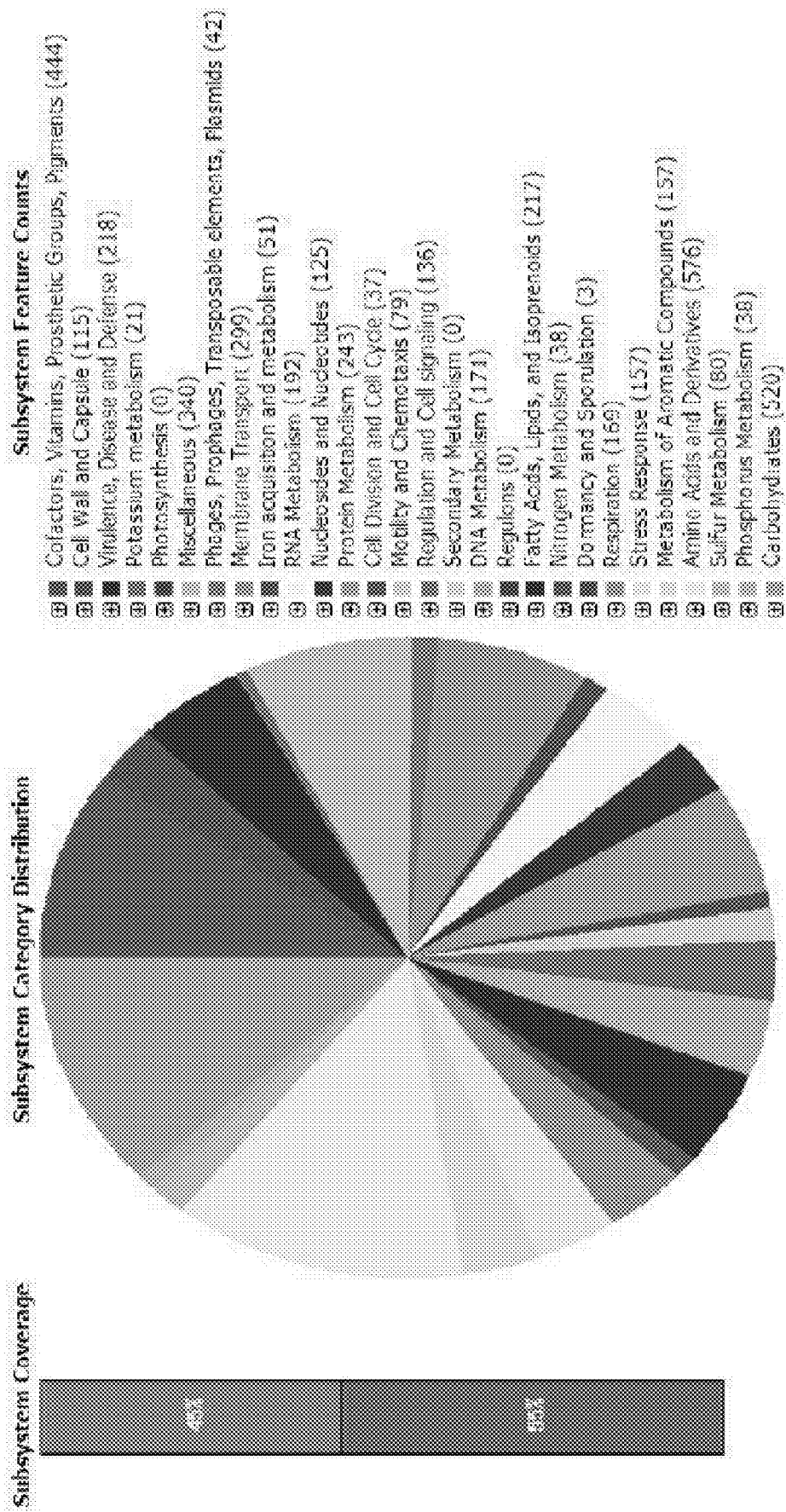

FIG. 20 illustrates a 16s rRNA phylogenic tree of our novel *Delftia* isolates. The Neighbor-joining phylogeny analysis indicates that the *Delftia* that were isolated from various natural resources by DSA, clustered into several distinct branches.

FIG. 21 is a table summarizing the percent growth inhibition of other independent clones for antimicrobial potency. Percent growth inhibition (of target bacteria not exposed to *Delftia* supernatant), is presented—yellow-high inhibition, gray-intermediate inhibition and white-weak inhibition. The data represented is the average of 2 independent experiments proceeded in triplicates.

FIGS. 22A-G illustrate the overall gene composition of strains 75-A, 119-B, 120-C, 261-D, 122-E and 123-F and 2189-G: The sequences of the strains were uploaded to the RAST (Rapid Annotation using Subsystem Technology) server for fully-automated genome annotating. The diagram was created by The SEED Viewer server.

FIGS. 23A-D illustrate production of biofilm by *Delftia* strain 2189 in response to various toxic compounds.

FIGS. 24A-C are photographs illustrating swarming, production of fruiting bodies and spores by *Delftia* strain 2189: A. *Delftia* strain 2189 was inoculated at the center of swarm agar and incubated at 30° C. for 6 days. The colonies were examined using Leica motorized binocular. The magnification factor is indicated. B and C. Samples from fresh cultures as well as fruiting bodies producing colonies were withdrawn for gram staining and microscopic examination (FB-fruiting bodies).

Figures 25A, 25B:
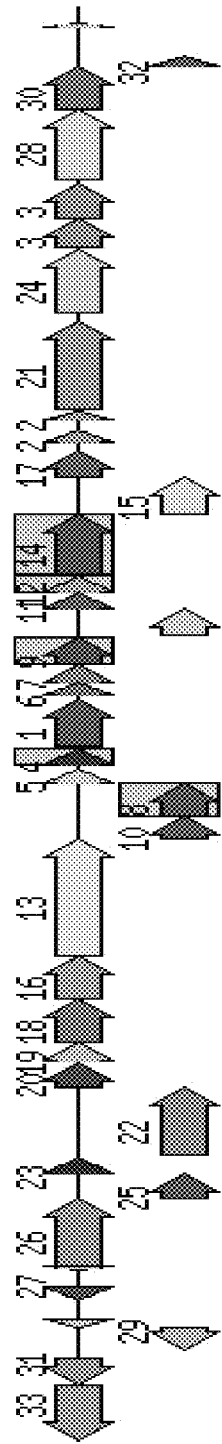

FIGS. 25A-B illustrate the Genome Locus containing the type VI secretion system of *Delftia* strain 2189. The sequence of strain 2189 was uploaded to the RAST (Rapid Annotation using Subsystem Technology) server for fully-automated genome annotating. The diagram was created by The SEED Viewer server.

Figure 26A:
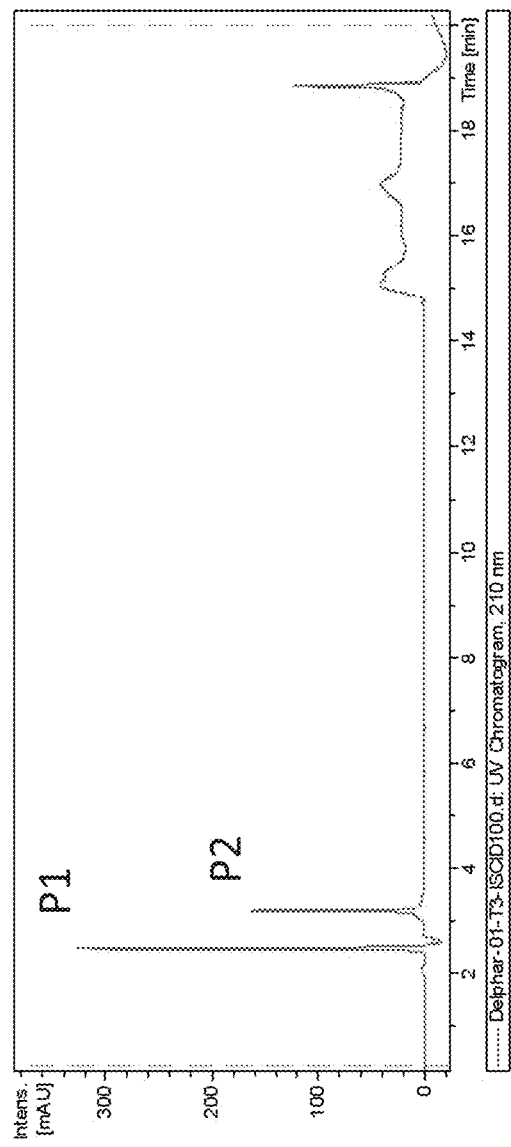

FIG. 26A is a chromatogram showing the trace of UV absorbance at 210 nm for Delftibactin A purified to 93.8%. Both peaks, P1 and P2, contained the same component of mass 1032.4829.

Figure 26B:
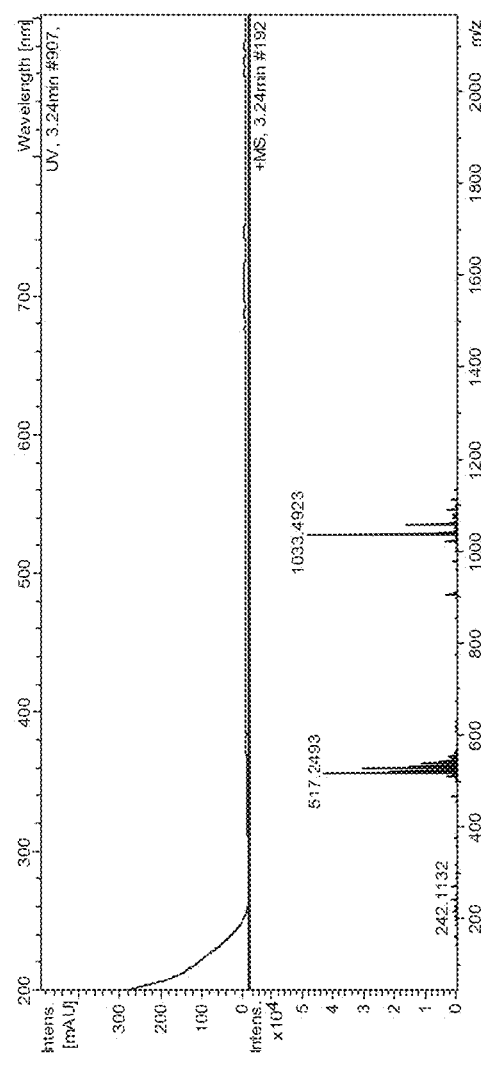

FIG. 26B is readout of mass spectra analysis showing the presence of amino acids in the structure.

Figures 27A, 27B:
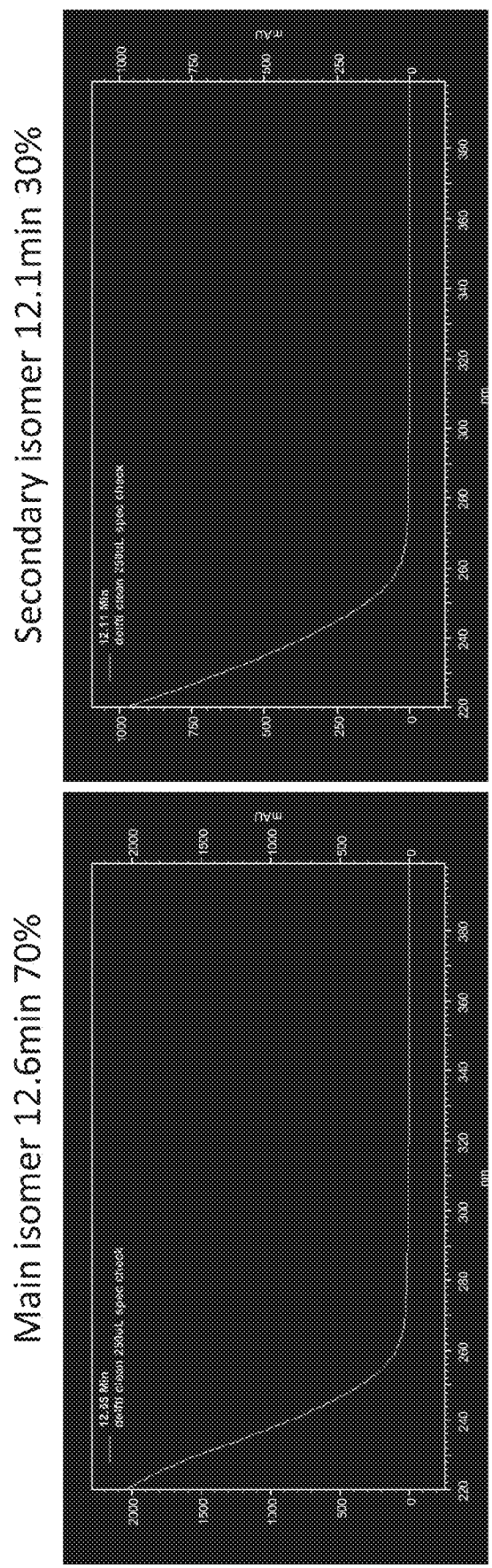
Figure 28A:
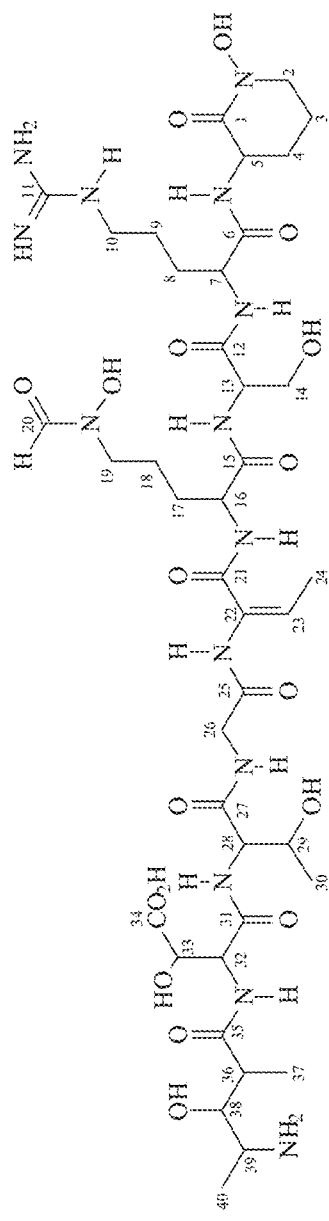
Figure 28B:
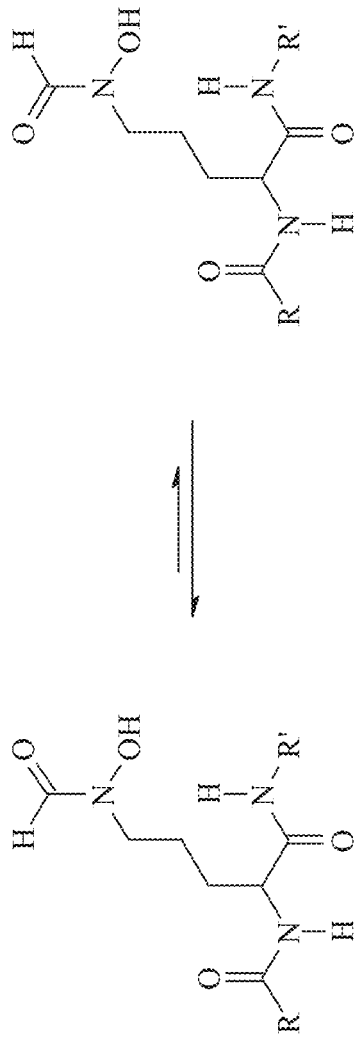

FIGS. 27A-B are readouts of absorbance spectrum of purified Delftibactin A, The two isomers are illustrated in FIG. 28B.

FIG. 28A provides the structure of DeftibactinA, numbered as per the paper of C. W. Johnston, M. A. Wyatt, X. Li, A. Ibrahim, J. G. Southam and N. A. Magarvey, *Nature Chem. Biol.* 9, 241 (2013).

FIG. 28B provides the structures of formamide rotamers.

Figure 29A:
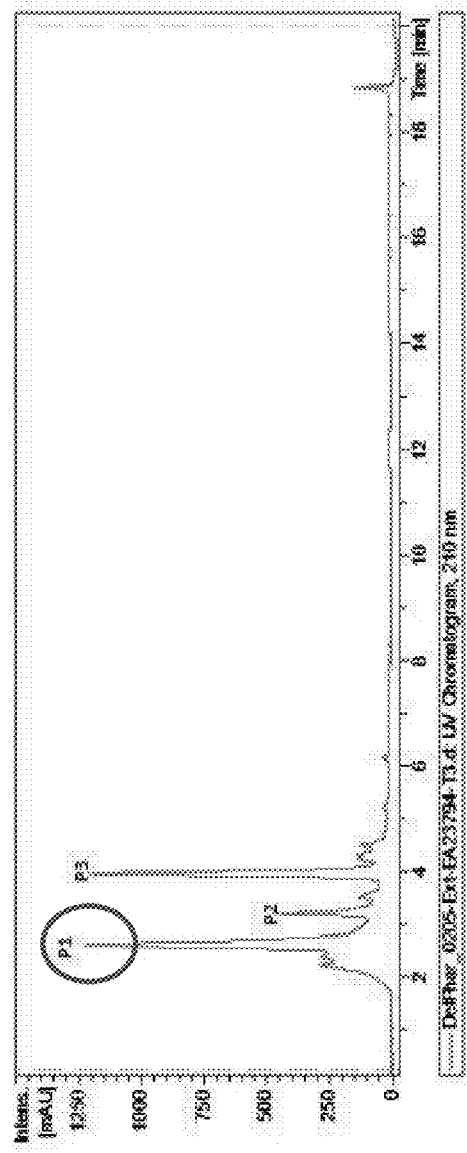

FIG. 29A are readouts of spectral analysis following HPLC separation at 210 nm.

Figure 29B:
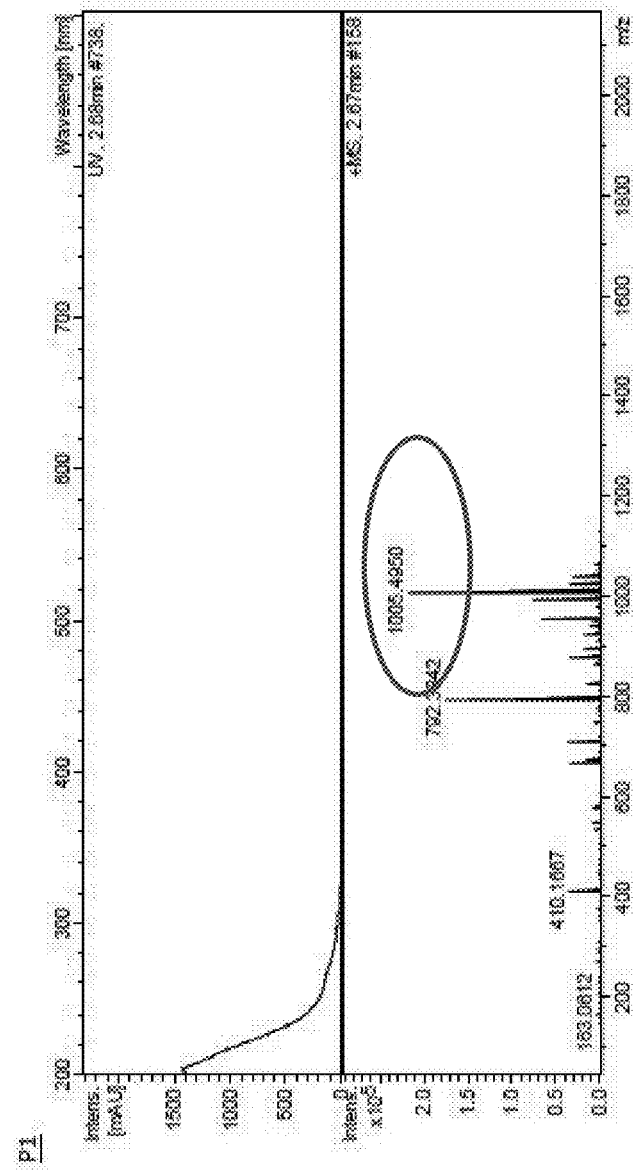

FIG. 29B is a mass spec analysis of the major component from peak 1.

Figure 30:
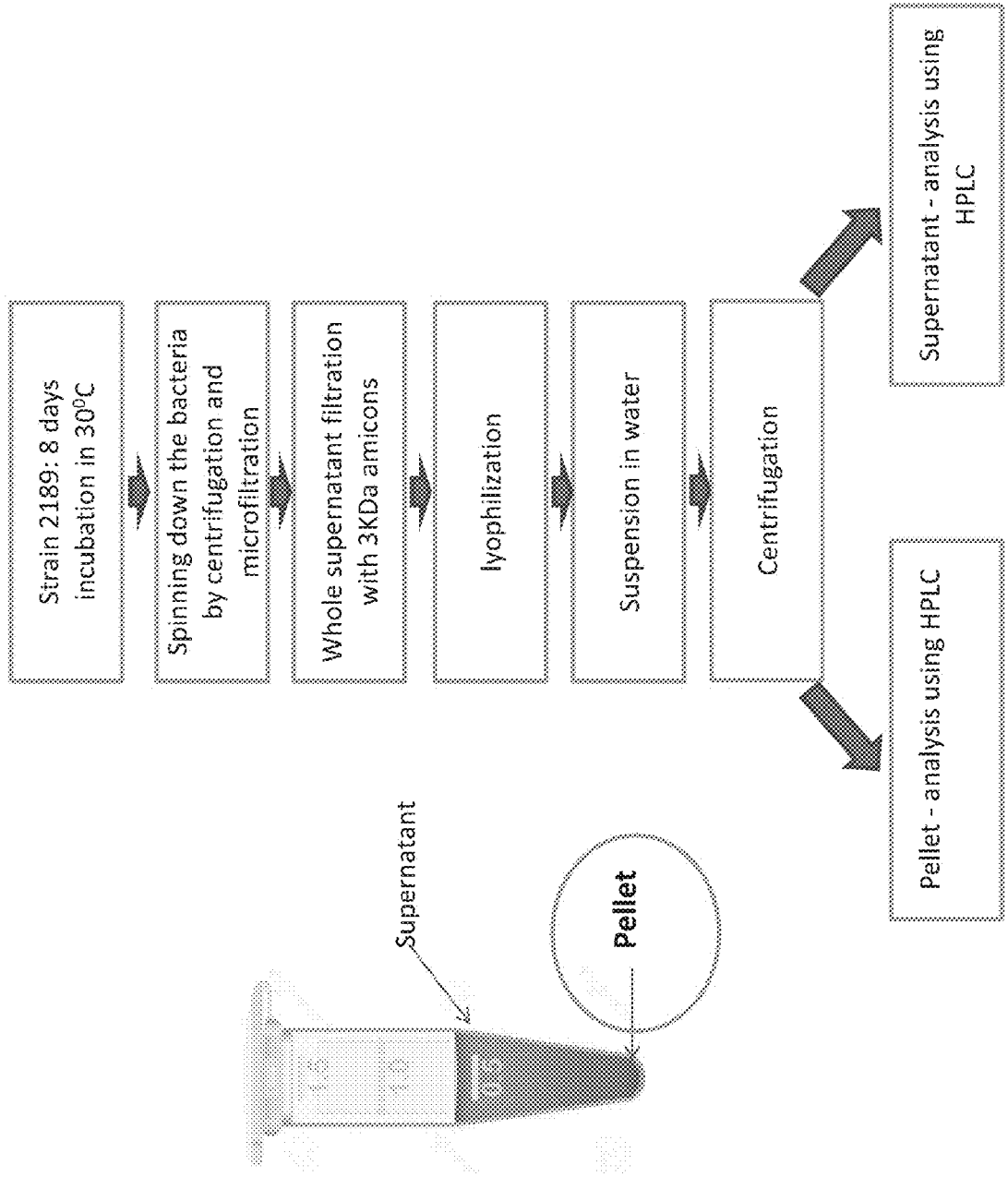

FIG. 30 is a flow diagram of the preparation for HPLC analysis and fractionation.

Figure 31:
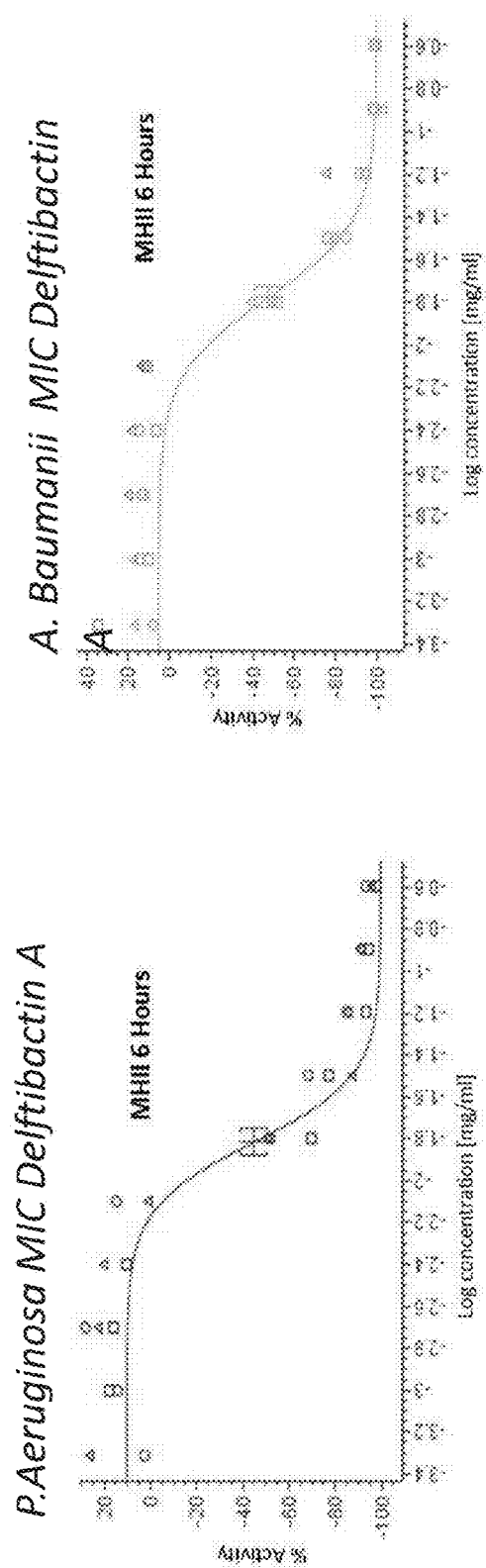

FIG. 31 are tables and graphs illustrating the MIC for delftibactin A towards *K. pneumoniae, A. baumanii* and *P. Aeruginosa* as measured at 6 hours or 19 hours.

Figure 32:
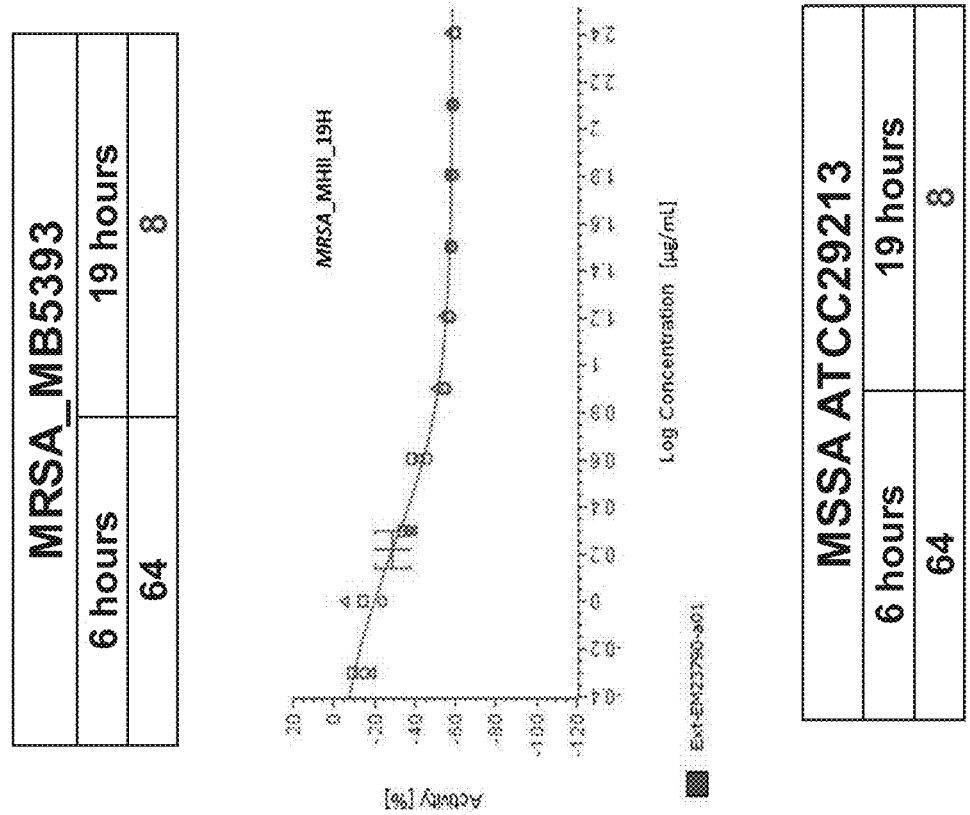

FIG. 32 are tables and graphs illustrating the MIC for delftibactin A towards MRSA_MB5393, MRSA_MHII_19H and MSSA as measured at 6 hours or 19 hours.

Figure 33:
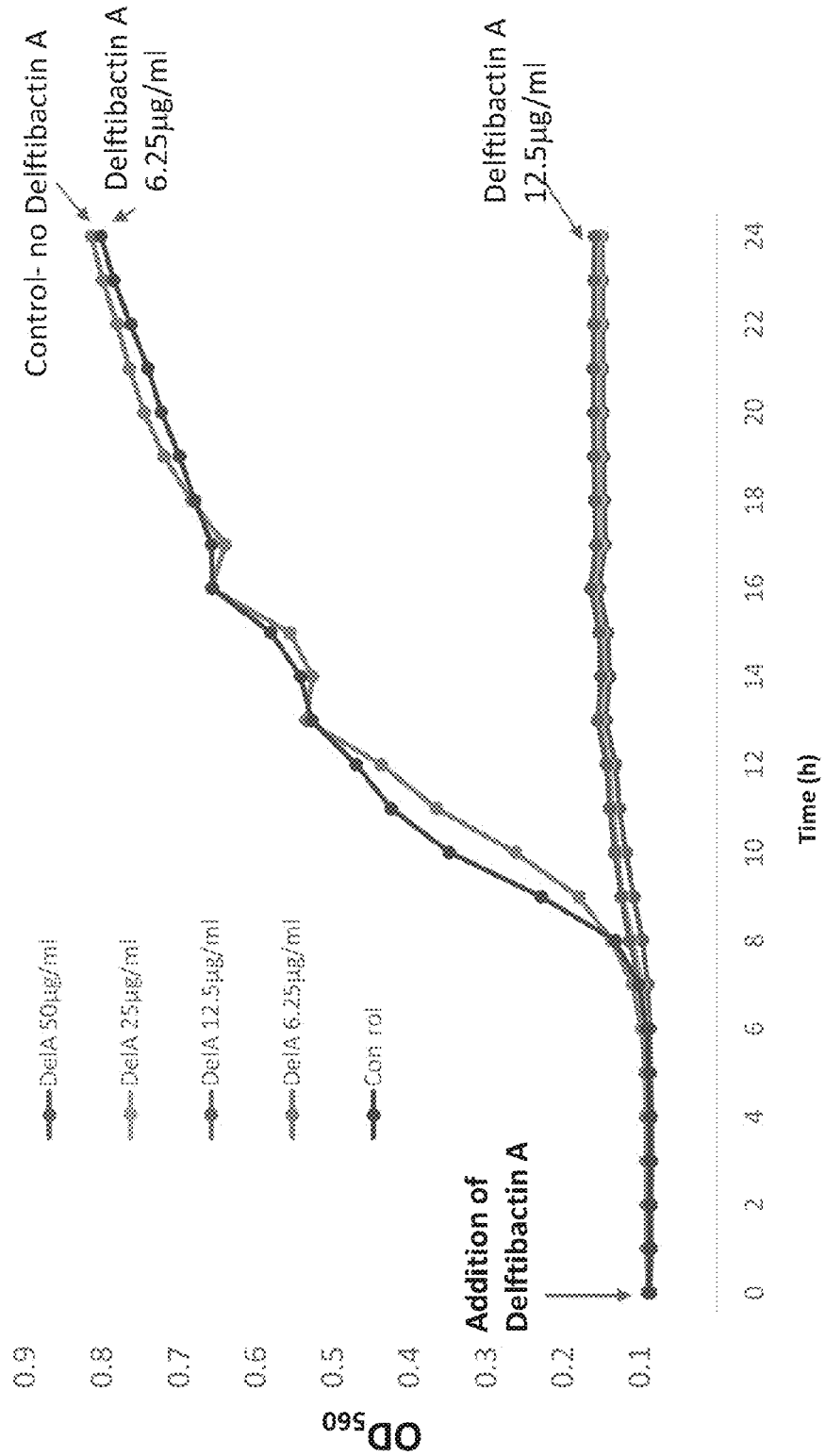

FIG. 33 is a graph illustrating that Delftibactin A inhibits Vancomycin Resistant Enterococci (VRE).

Figure 34:
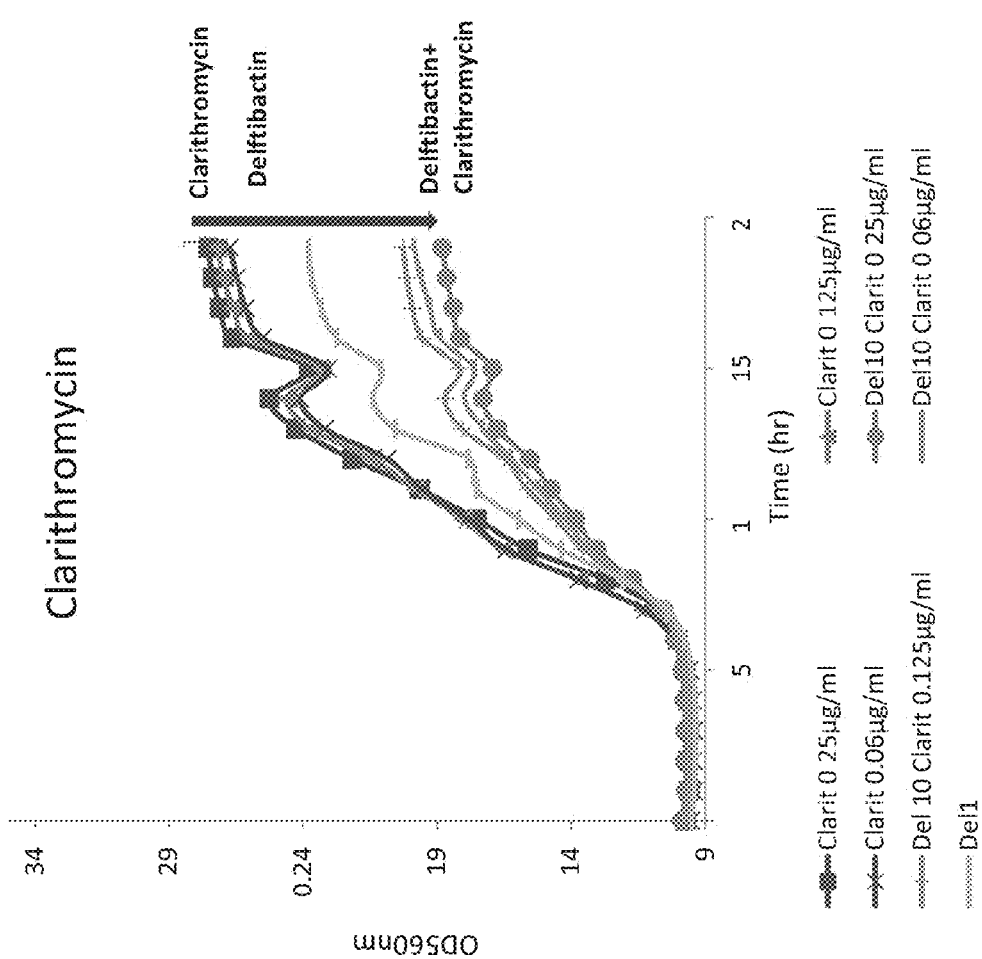

FIG. 34 is a graph illustrating that Delftibactin A (10 µM) has additive combined antimicrobial effect with clarithromycin on VRE.

Figure 35:
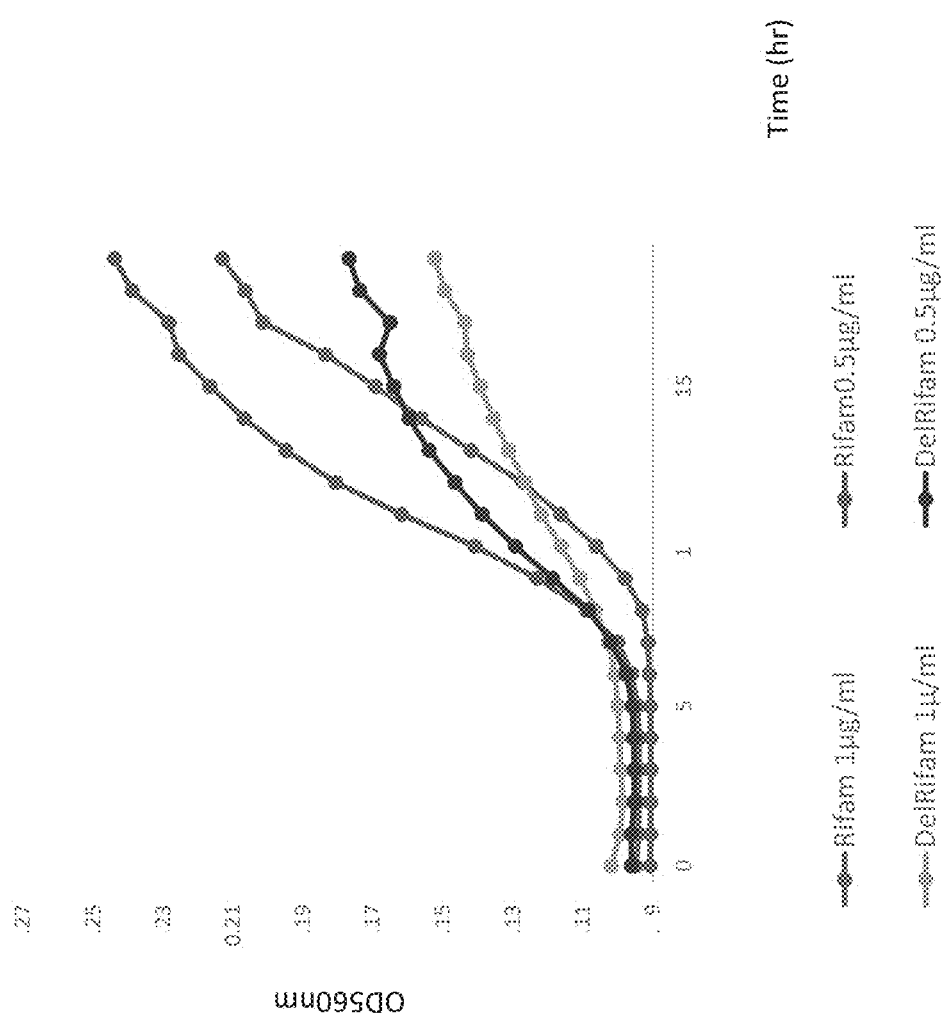

FIG. 35 is a graph illustrating that Delftibactin A (10 µM) has additive combined antimicrobial effect with rifampicin on VRE.

Figure 36:
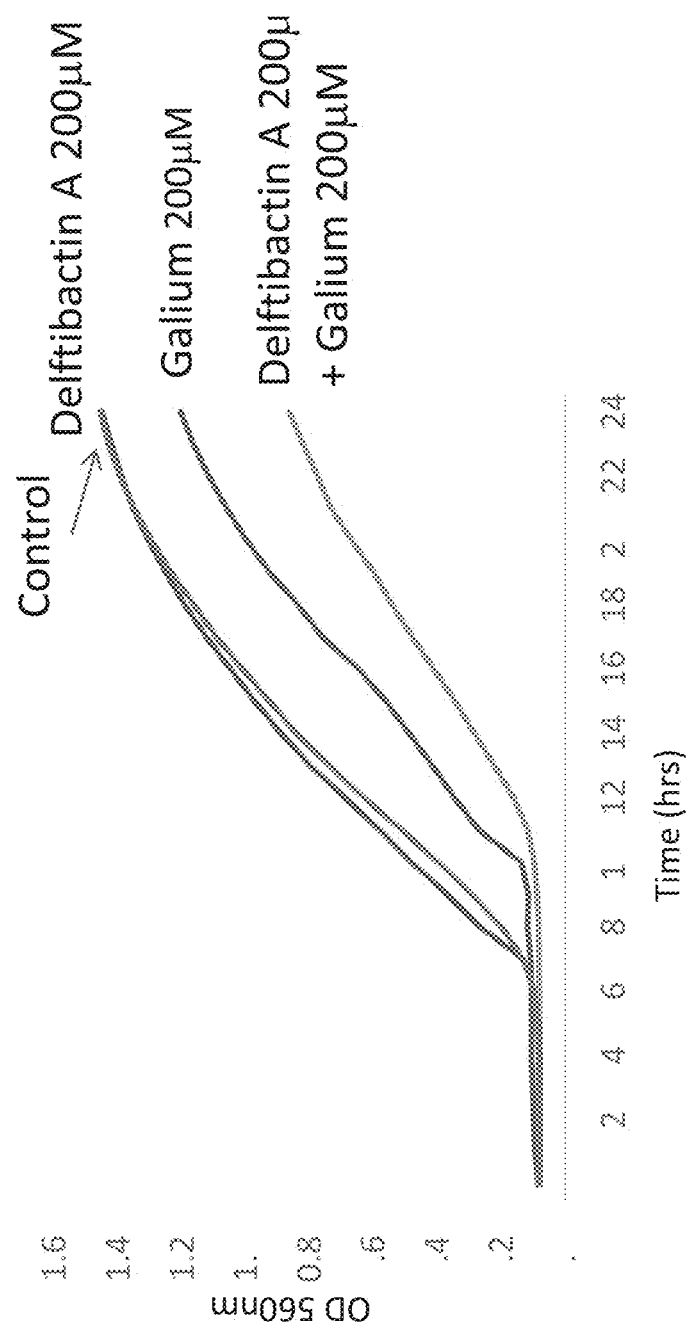

FIG. 36 is a graph illustrating that Delftibactin A can be used as a carrier of inhibitory antimicrobial agents such as gallium to inhibit harmful bacterial strains such as Deftia strain 2189.

Figure 37:
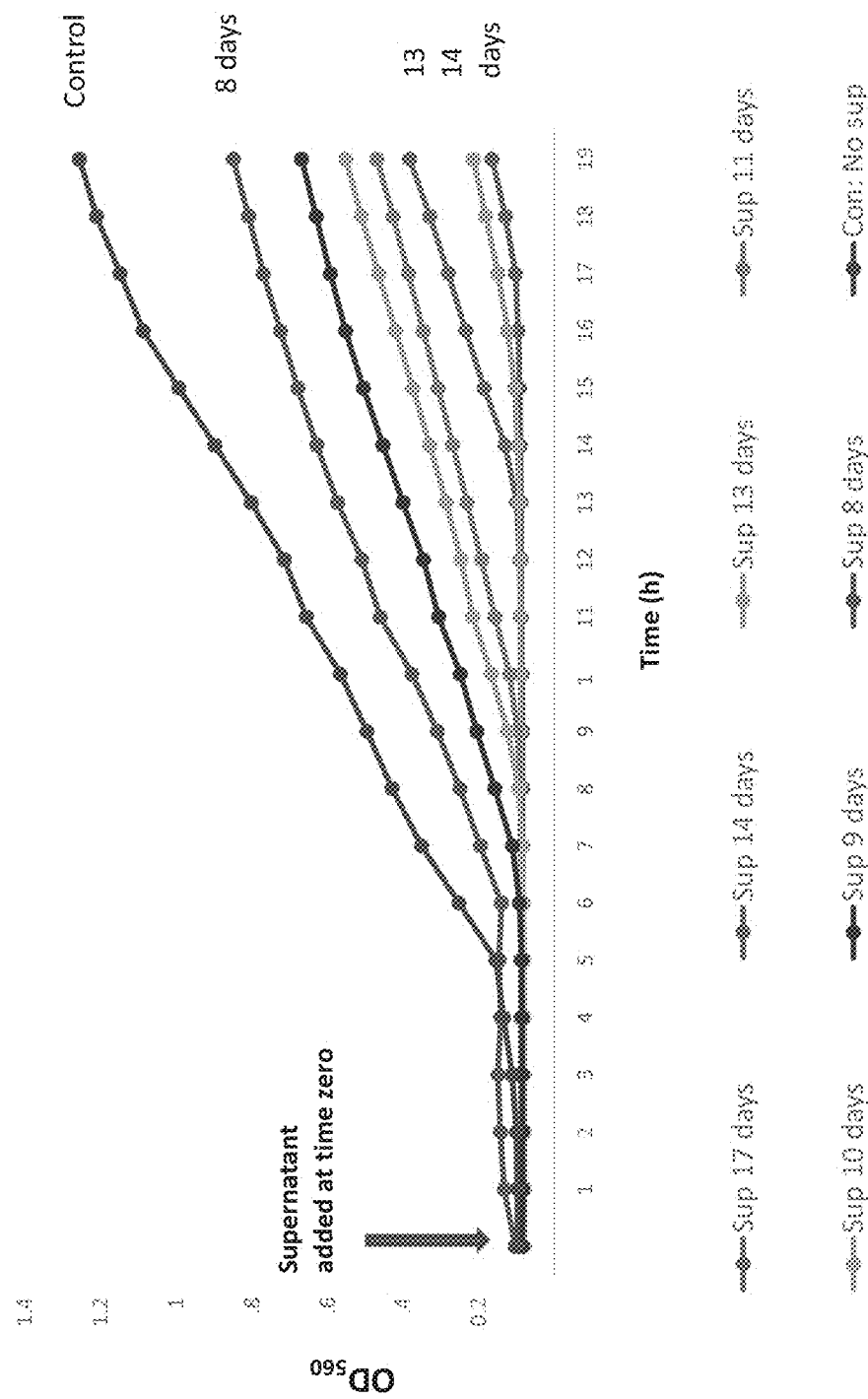

FIG. 37 is a graph illustrating that supernatants harvested at different time points (8-17 days) from strain 2189 can be used to inhibit growth of *Acinetobacter baumannii* 179.

Figure 38:
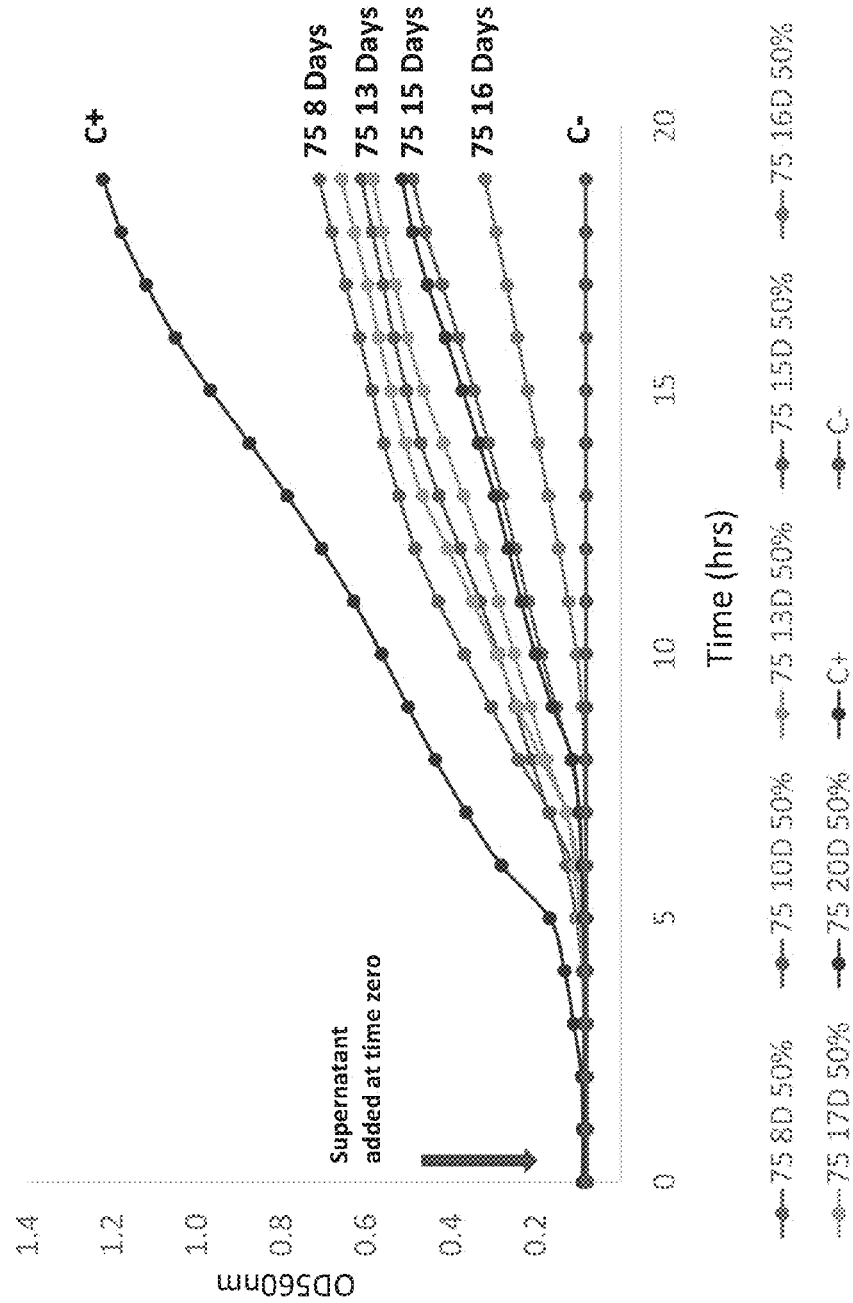

FIG. 38 is a graph illustrating that supernatants harvested at different time points (8-17 days) from strain 75 can be used to inhibit growth of *Acinetobacter baumannii* 179.

Figure 39:
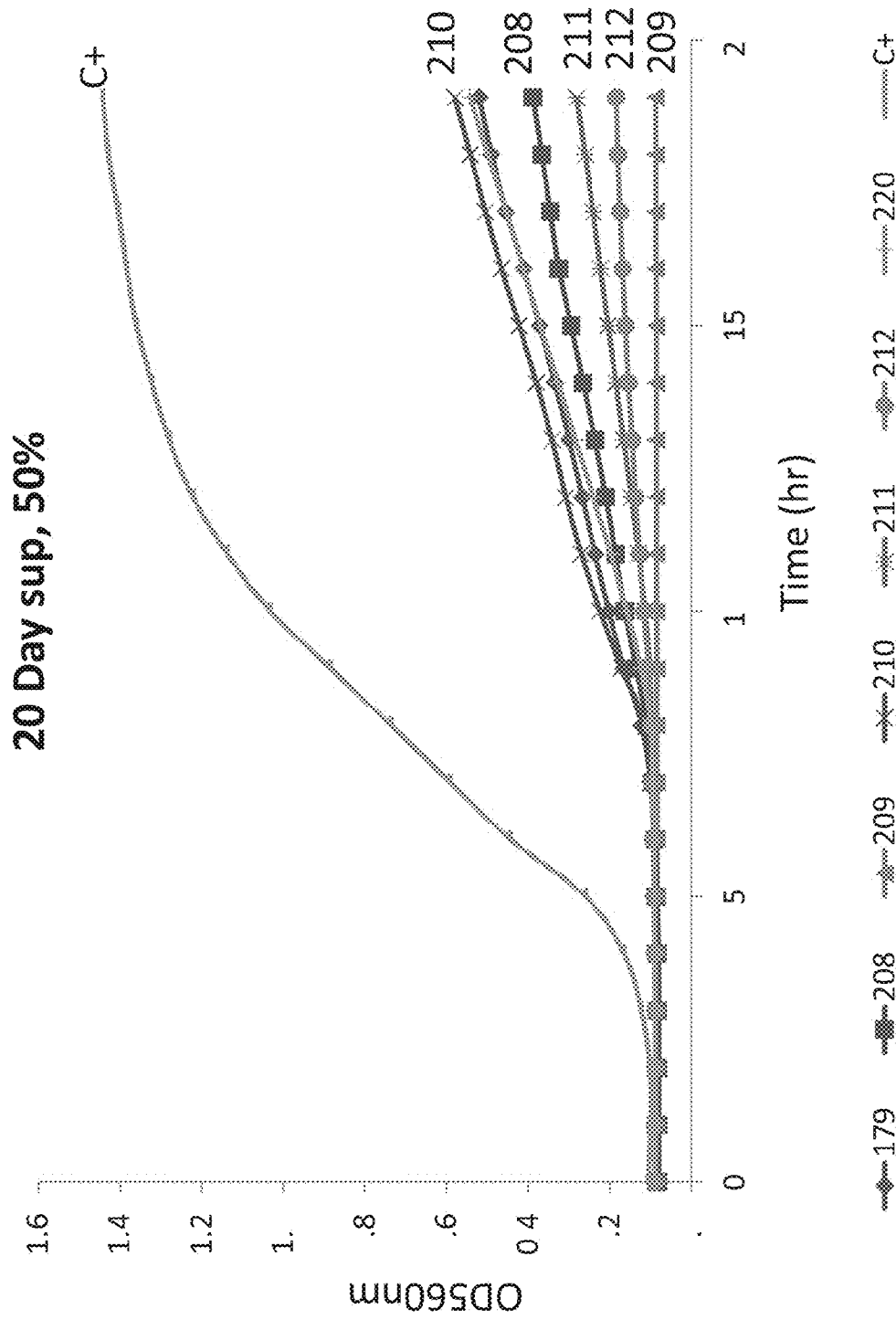

FIG. 39 is a graph illustrating that 2189 supernatant inhibits growth of all tested MDR/XDR ACB strains.

Figure 40:
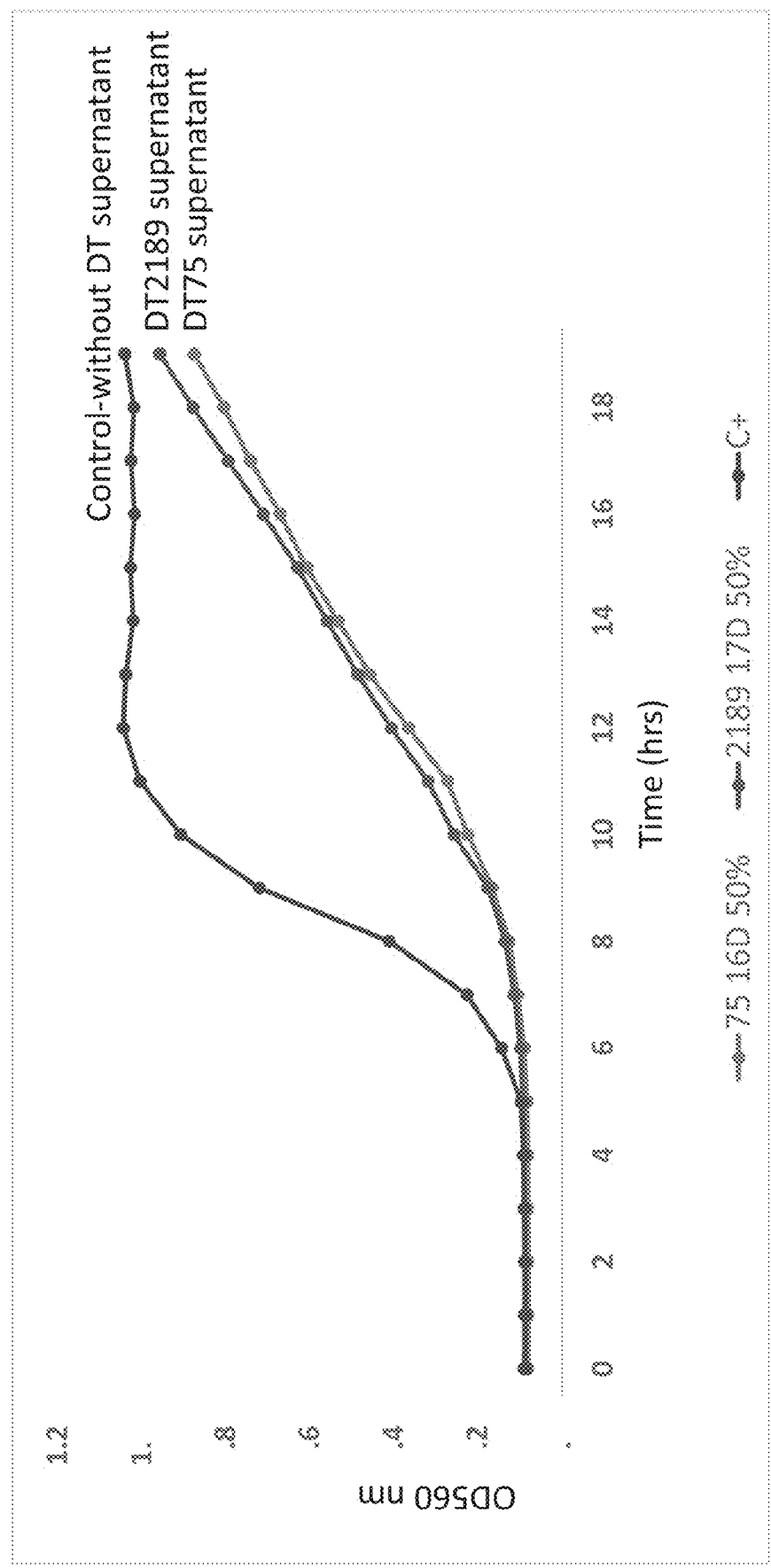

FIG. 40 is a graph illustrating that *Delftia* supernatants cause elongation of generation time in *Pseudomonas aeruginosa*.

Figure 41A:
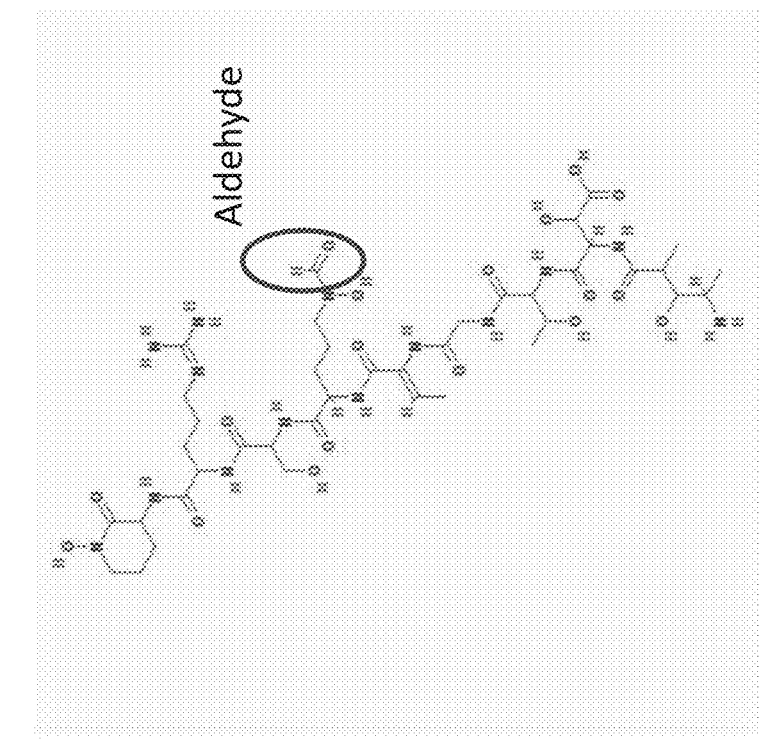
Figure 41B:
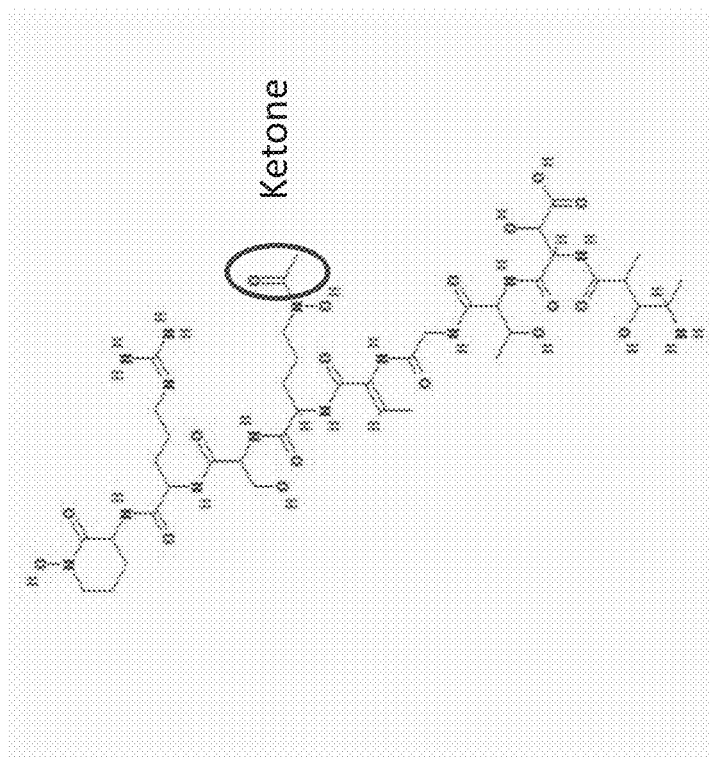

FIGS. 41A-B provide the chemical structures of delftibactin A and delftibactin B.

Figure 42:
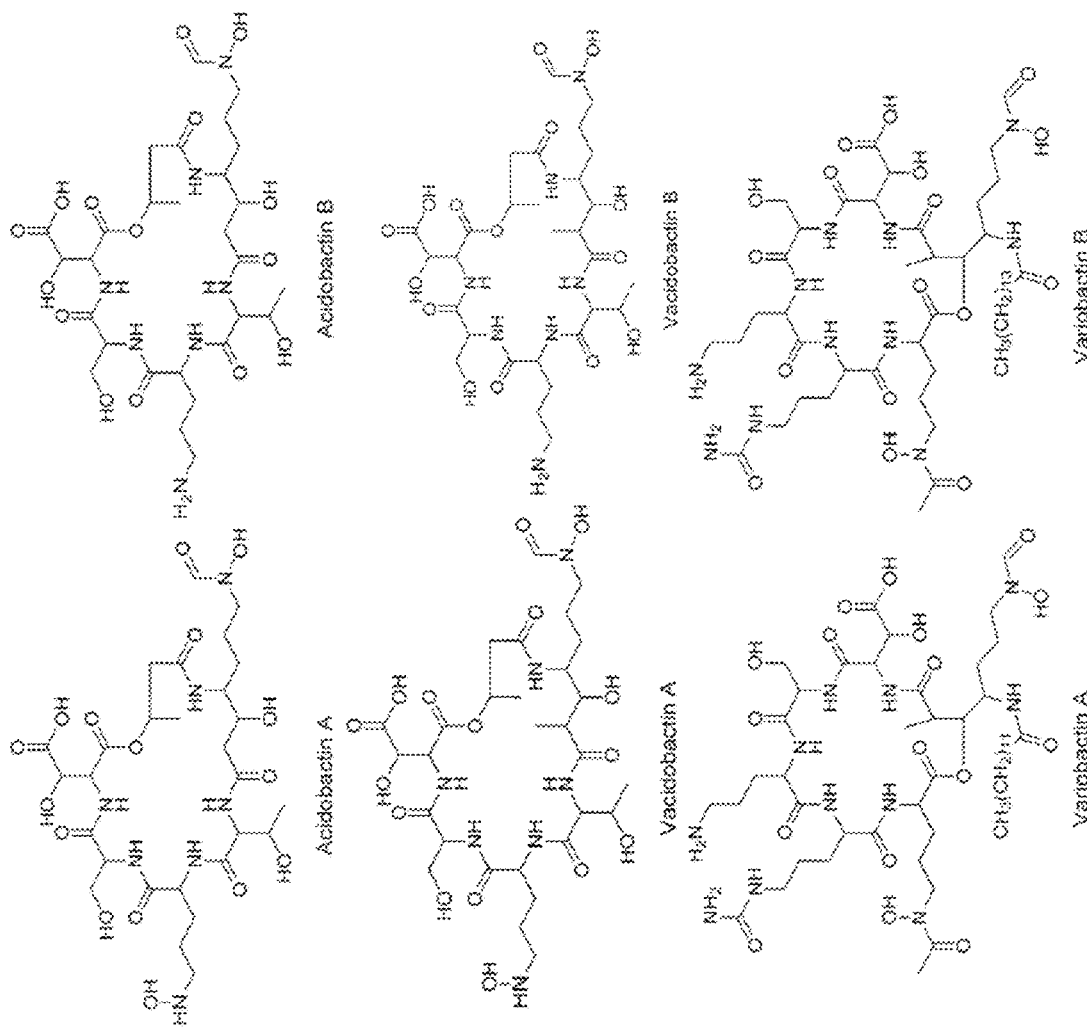
Figure 42:
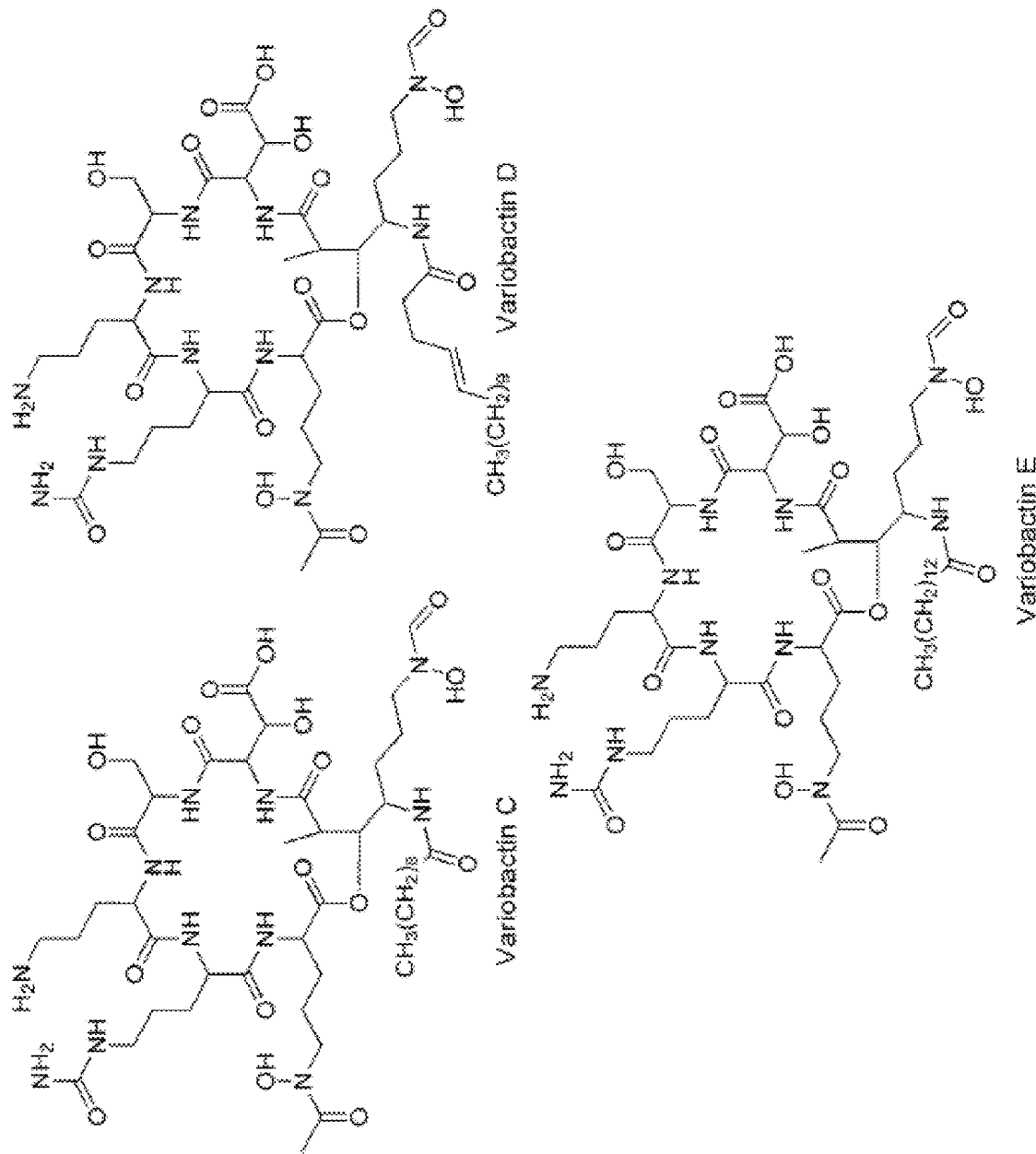

FIG. 42 shows chemical structures of metabolites related to delftibactin as follows: Acidobactin A; Acidobactin B; Vacidobactin A; Vacidobactin B; Variobactin A; Variobactin B; Variobactin C; Variobactin D; and Variobactin E, as further exemplary embodiments of the present application.

DESCRIPTION OF SPECIFIC EMBODIMENTS OF THE INVENTION

The present invention, in some embodiments thereof, relates to antimicrobial agents derived from the *Delftia* bacteria.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Whilst studying various strains of *Delftia* bacteria, the present inventors noticed that when particular *Delftia* bacteria are seeded a few centimeters apart from another strain (e.g. *E. coli*) on the same swarm agar plate, the *Delftia* cells swarm towards the target colony. After reaching the target colony, the *Delftia* enclose the colony and lyse the cells. In particular, the present inventors found that *Delftia* bacteria strains produce active antimicrobial compounds against multiple drug resistant (MDR) clinical isolates including *Staphylococcus aureus* (MRSA), *Klebsiella pneumonia* (KPC), *Acinetobacter baumannii* and Vancomycin resistant *Enterococcus* (VRE) (FIGS. 2A-B and Table 1).

The present inventors confirmed that the antibacterial activity of *Delftia* sp. is a combination of at least two different mechanisms that act together: secretion of antimicrobial compounds and contact dependent inhibition.

Size fractionation of *Delftia* supernatant, illustrated that most of the active compounds produced in complex media are between 1-3 kDa (FIGS. 5A-E), whereas most of the active compounds produced in minimal media are below 1 kDa. Characterization of size-fractionated active fractions of these isolates showed that the compounds are DNase, RNase, Proteinase K and heat resistant (FIGS. 6 and 7).

Using reverse phase chromatography, the present inventors isolated active compounds by eluting from eluting with 6% acetonitrile from a Sep-Pak tC18 column (FIG. 8).

Whilst further reducing the present invention to practice, the present inventors developed and optimized growth conditions for the production of the anti-microbial compounds from the *Delftia* isolates in minimal defined media, so as to enable identification of the active compounds by High performance liquid chromatography (HPLC) fractionation.

HPLC analysis indicated differential peaks between active and non-active fractions. In particular, the present inventors showed that strains 75 and 2189 produced a library of antimicrobial compounds, as seen by the different active fractions and the different absorbance spectra of the compounds in the active fractions (FIGS. 11A-16).

Liquid chromatography-mass spectrometry (LCMS) analysis of the active fractions also confirmed production of a library of compounds (Tables 2-5).

The present inventors propose that the novel antimicrobial agents derived from the *Delftia* isolates may be used to kill microbes in general and bacteria in particular.

Thus, according to another aspect of the present invention there is provided a method of generating an antimicrobial agent comprising:

(a) culturing a *Delftia* bacteria in a medium under conditions effective to allow secretion of at least one antimicrobial agent into the medium; and (b) isolating the at least one antimicrobial agent from the medium to generate a purified preparation comprising the at least one antimicrobial agent, wherein the antimicrobial agent is not $C_{17}H_{19}NO_3S$ or a delftibactin, thereby generating the antimicrobial agent.

As used herein, the term "antimicrobial agent" refers to an agent having antimicrobial activity—i.e. the ability to suppress, control, inhibit or kill microorganisms, such as bacteria, fungi, viruses, protists and archae.

According to a particular embodiment, the antimicrobial agent is not an antifungal agent.

According to a specific embodiment, the antimicrobial agent is an antibacterial agent.

The antibacterial agent of this aspect of the present invention may comprise bactericidal and/or bacteriostatic towards at least one gram positive bacteria and/or one gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abcessus*, *Mycobacterium avium* complex, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terrae*, *Mycobacterium tuberculosis*, *Mycobacterium ulcerans*, *Nocardia* spp., *Peptococcus niger*, *Peptostreptococcus* spp., *Proprionibacterium* spp., *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, *Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus*, *Actinobacillus actinomycetemcomitans*, *Aeromonas hydrophila*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chalmydia pneumoniae*, *Chlamydia psittaci*, *Chlamydia trachomatis*, *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella* spp., *Legionella* spp., *Leptospira* spp., *Moraxella catarrhalis*, *Morganella morganii*, *Mycoplasma pneumoniae*, *Neisseria gonorrhoeae*, *Neisseria meningitidis*, *Pasteurella multocida*, *Plesiomonas shigelloides*, *Prevotella* spp., *Proteus* spp., *Providencia rettgeri*, *Pseudomonas aeruginosa*, *Pseudomonas* spp., *Rickettsia prowazekii*, *Rickettsia rickettsii*, *Rochalimaea* spp., *Salmonella* spp., *Salmonella typhi*, *Serratia marcescens*, *Shigella* spp., *Treponema carateum*, *Treponema pallidum*, *Treponema pallidum endemicum*, *Treponema pertenue*, *Veillonella* spp., *Vibrio cholerae*, *Vibrio vulnificus*, *Yersinia enterocolitica*, *Yersinia pestis*.

According to particular embodiments, the agent of this aspect of the present invention comprises antibacterial activity against *Pseudomonas aeruginosa* and *Klebsiella pneumonia*, *E. coli* (e.g. J5-3, MC4100), *S. aureus* strains (MSSA, MRSA, including the pandemic strain USA300) and *Enterococcus faecalis*. The antibacterial activity of the *Delftia* (contact dependent and secretion of antimicrobial compounds) against *E. coli*, *S. aureus* is preferably bactericidal (FIGS. 1A-C, 2A). Further details about the antibacterial activity of the *Delftia* bacterial strains are provided in Table 1 of the Examples section herein below, FIG. 21 and FIGS. 31-33.

In one embodiment, the agent of this aspect of the present invention has at least 5 times and more preferably 10 times greater antibacterial activity towards *E. coli* strains J5-3 and MC4100 than towards *E. coli* strain ATCC 25922 when measured in an identical assay under the same conditions.

The term "*Delftia* bacteria" refers to a genus of bacteria belonging to the family Comamonadaceae.

Contemplated strains of *Delftia* bacteria include, but are not limited to *D. acidovorans*, *D. lacustris*, *D. litopenaei*, *D. tsuruhatensis* and *D. deserti*.

In one embodiment, the strain of *Delftia* bacteria includes the *Delftia* strain 75, *Delftia* strain 2189, *Delftia* strain 2248, *Delftia* strain 2350, *Delftia* strain 2260, *Delftia* strain 2361, *Delftia* strain 107, *Delftia* strain 108, *Delftia* strain 119, *Delftia* strain 120, *Delftia* strain 121, *Delftia* strain 122, *Delftia* strain 123, *Delftia* strain 158, *Delftia* strain 159, *Delftia* strain 160 and *Delftia* strain 161.

In a particular embodiment, the strain of *Delftia* bacteria is DSM No. 39 which can be obtained from the German Resource Centre for Biological Material (DSMZ, DSM No. 39).

In another embodiment, the strain of *Delftia* bacteria has a genome comprising a polynucleotide sequence at least 90%, 91%, 92%, 93%, 94%, 95%, 96%, 97%, 98%, 99% or 100% homologous to the genome polynucleotide sequence as set forth in Accession numbers ERS1087230, SAMEA3900096-DT123; ERS1087231, SAMEA3900097-DT2361; ERS1087229, SAMEA3900095-DT122; ERS1087228, SAMEA3900094-DT120; ERS1087227, SAMEA3900093-DT119; ERS1087226 SAMEA3900092-DT75; or ERS1090440, SAMEA3903306-Delftia strain 2189 filed under project number PRJEB13025.

In yet another embodiment, the *Delftia* bacteria from which the antimicrobial agent is isolated is one which grows on a selective agar which comprises a minimal media and phthalic acid as a carbon source (e.g., 0.5% phthalic acid). Typically, the agar also comprises antibiotics. The minimal media typically comprises salts such as magnesium, nitrogen, phosphorus, and sulfur to allow the bacteria to synthesize protein and nucleic acid. Exemplary commercially available minimal media include, but are not limited to Davis minimal medium.

The antimicrobial agent derived from the *Delftia* bacteria is typically greater than 1 kDa in complex media.

The term "complex media" as used herein refers to media which comprise polypeptides and polynucleotides.

The term "minimal medium" as used herein refers to a chemically defined medium, which includes only the nutrients that are required by the cells to survive and proliferate in culture. Typically, minimal medium is free of biological extracts, e.g., growth factors, serum, pituitary extract, or other substances, which are not necessary to support the survival and proliferation of a cell population in culture. For example, minimal medium generally includes as essential substances: at least one carbon source, such as glucose; at least one nitrogen source, such as ammonium, ammonium sulfate, ammonium chloride, ammonium nitrate or urea; inorganic salts, such as dipotassium hydrogenphosphate, potassium dihydrogen-phosphate and magnesium sulfate; and other nutrients, such as biotin and vitamins.

The term "complex medium" refers to a medium that comprises at least one complex ingredient such as yeast extract or casein hydrolysate, which consist of a mixture of many, many chemical species (e.g. polynucleotides/polypeptides) in unknown proportions.

In one embodiment, the antibacterial agent derived from the *Delftia* bacteria is between 1 kDa-10 kDa. In another embodiment, the antibacterial agent derived from the *Delftia* bacteria is between 1 kDa-3 kDa. In another embodiment in minimal media the antimicrobial agent produced by *Delftia* is smaller than 1 kDa.

Preferably, the antimicrobial agent is not a polynucleotide.

In another embodiment, the antimicrobial agent is resistant to the activity of proteinase K.

In one embodiment, the antimicrobial agent is a polysaccharide or an organic metabolite.

As mentioned, in order to generate a purified preparation of the antimicrobial agent of this aspect of the present invention, the *Delftia* bacteria are cultured in a medium under conditions effective to allow secretion of the antimicrobial agent into (or onto) the medium.

In one embodiment, the medium is a liquid medium (complex or minimal).

Contemplated liquid media in which the *Delftia* bacteria are cultured include Davis+glycerol.

In another embodiment, the medium is a solid medium.

Preferably, the *Delftia* bacteria are cultured for at least 6 hours, 12 hours, 24 hours, 48 hours, 3 days, 4 days, 5 days, 6 days, 7 days, 8 days or more to allow for sufficient quantities of the antimicrobial agent to be secreted.

In one embodiment, the *Delftia* bacteria are cultured at a temperature between 28-40° C., more preferably between 28-32° C.—for example at about 30° C.

According to a particular embodiment, the *Delftia* bacteria are cultured for about 3 days at about 30° C.

Following sufficient time in culture, the antimicrobial agents are isolated from the culture.

In one embodiment, a single antimicrobial agent is isolated from the culture.

In other embodiments, a plurality (for example 2-20 or 2-10) different antimicrobial agents are isolated from the culture.

In yet another embodiment, at least two, three, four, five or more antimicrobial agents are isolated from a single culture.

The term "isolated" as used herein refers to an agent that is substantially separated from other components which naturally accompany the native agent, such as other bacterial cellular components for an isolated bacterial metabolite.

Preferably, the method for preparing the purified preparation which comprises the antimicrobial agent involves a step of removing the extracellular fraction of the culture medium from the *Delftia* cells. The extracellular fraction of the liquid fermentation medium is also termed the supernatant and this fraction can be separated from the *Delftia* cellular fraction by e.g. centrifugation or filtration, or indeed by any other means available for obtaining a liquid fraction essentially without any bacterial cells present therein.

In preferred embodiments of the invention the purification comprises at least one size fractionation step. Preferably, this size fractionation step is performed on the extracellular fraction. This size fractionation step may ensure that every component of the composition has a molecular weight of at least a given value. The size fractionation step may be any size fraction known to the skilled person, for example ultracentrifugation, ultrafiltration, microfiltration or gel-filtration. Thus in a preferred embodiment of the invention, the agent is purified from a liquid growth medium by a method involving one or more purification steps selected from the group consisting of ultracentrifugation, ultrafiltration, microfiltration and gel-filtration. Preferably, the purification step(s) are selected from the group consisting of ultrafiltration, microfiltration and ultracentrifugation, even more preferably from the group consisting of ultrafiltration and microfiltration.

Ultrafiltration is a membrane process where the membrane fractionates components of a liquid according to size. The membrane configuration is normally cross-flow wherein the liquid containing the relevant components are flowing across the membrane. Some of the liquid, containing components smaller than the nominal pore size of the membrane will permeate through the membrane. Molecules larger than the nominal pore size will be retained. The desired product may be in the retentate or the filtrate. If the ultrafiltration is performed in order to prepare a composition, wherein every agent within the composition has a molecular weight above a given value, the desired product is in the retentate. If a serial fractionation is made, the product may be in the retentate or filtrate.

Microfiltration is a membrane separation process similar to UF but with even larger membrane pore size allowing larger particles to pass through.

Gel filtration is a chromatographic technique in which particles are separated according to size. The filtration medium will typically be small gel beads which will take up the molecules that can pass through the bead pores. Larger molecules will pass through the column without being taken up by the beads.

Gel-filtration, ultrafiltration or microfiltration may for example be performed as described in R Hatti-Kaul and B Mattiasson (2001), Downstream Processing in Biotechnology, in Basic Biotechnology, eds C Ratledge and B Kristiansen, Cambridge University Press) pp 189.

In another embodiment the antimicrobial agent in the medium may be isolated by precipitation, such as precipitation with alcohol, such as ethanol and/or chromatographic methods. This may for example be performed essentially as described in WO2003/020944. It is also contemplated within the invention that the antimicrobial agents are isolated by sequentially performing two or more of above-mentioned methods. By way of example the antimicrobial agent may be isolated by first performing a size fractionation step followed by precipitation.

Other methods for isolating the antimicrobial agent of this aspect of the present invention are also contemplated by the present inventors including but not limited to HPLC.

In one embodiment, the antimicrobial agents are further purified from the filtrate by HPLC. The filtrate is loaded onto a reverse phase C18 column (e.g. Sep-Pak tC18 column) preferably packed with a Silica-based bonded phase with strong hydrophobicity and developed with a 0-80% acetonitrile (ACN) gradient in 0.01%-0.05% trifluoroacetic acid (TFA). In one embodiment, the agent is eluted at 6% acetonitrile. The *Delftia* antibacterial activity is eluted from the HPLC column as a first antibacterial activity at between about 3-4 minutes (strains 75 & 2189), as a second antibacterial activity at between about 10-11 minutes (strain 75), and as a third antibacterial activity at between about 11-12 minutes (strain 2189). The eluted *Delftia* fractions may be pooled, sterile filtered, and stored, for example at −80° C., until use. Alternatively, each *Delftia* elution fraction may be separately sterile filtered and stored for example at −80° C. until use.

Preferably more than 10% of the all the components of the purified preparation generated from the *Delftia* bacteria comprises antimicrobial activity. Preferably, more than 20% of all the components of the purified preparation generated from the *Delftia* bacteria comprises antimicrobial activity. In one embodiment, more than 30% of all the components of the purified preparation generated from the *Delftia* bacteria comprises antimicrobial activity. In one embodiment, more than 40% of all the components of the purified preparation generated from the *Delftia* bacteria comprises antimicrobial activity. In one embodiment, more than 50% of all the components of the purified preparation generated from the *Delftia* bacteria comprises antimicrobial activity.

Preferably more than 10% of the *Delftia*-derived components of the purified preparation comprise antimicrobial activity. Preferably more than 20% of the *Delftia*-derived components of the purified preparation comprise antimicrobial activity. In one embodiment, more than 30% of the *Delftia*-derived components of the purified preparation comprise antimicrobial activity. In one embodiment, more than 40% of the *Delftia*-derived components of the purified preparation comprise antimicrobial activity. In one embodiment, more than 50% of the *Delftia*-derived components of the purified preparation comprise antimicrobial activity. Following isolation of the antimicrobial agent, the activity thereof may be tested.

According to still another aspect of the present invention there is provided a composition of matter comprising at least one antimicrobial agent secreted from a *Delftia* bacteria, wherein the at least one antimicrobial agent is more than 1% of the *Delftia* components in the composition of matter, wherein the at least one antimicrobial agent is not $C_{17}H_{19}NO_3S$ or a Delftibactin.

In one embodiment, the at least one antimicrobial agent is between 1-100% of the *Delftia* components in the composition of matter, between 5-100% of the *Delftia* components in the composition of matter, between 10-100% of the *Delftia* components in the composition of matter, between 15-100% of the *Delftia* components in the composition of matter, between 20-100% of the *Delftia* components in the composition of matter, between 25-100% of the *Delftia* components in the composition of matter, between 30-100% of the *Delftia* components in the composition of matter, between 35-100% of the *Delftia* components in the composition of matter, between 40-100% of the *Delftia* components in the composition of matter, between 45-100% of the *Delftia* components in the composition of matter, between 50-100% of the *Delftia* components in the composition of matter, between 55-100% of the *Delftia* components in the composition of matter, between 60-100% of the *Delftia* components in the composition of matter, between 65-100% of the *Delftia* components in the composition of matter, or even between 70-100% of the *Delftia* components in the composition of matter.

The composition of matter of this aspect of the present invention is preferably devoid of $C_{17}H_{19}NO_3S$ or a Delftibactin.

The antimicrobial agent of this aspect of the present invention may be secreted from any *Delftia* bacteria. In a preferred embodiment, the bacteria has an Accession number ERS1087230, SAMEA3900096-DT123; ERS1087231, SAMEA3900097-DT2361; ERS1087229, SAMEA3900095-DT122; ERS1087228, SAMEA3900094-DT120; ERS1087227, SAMEA3900093-DT119; ERS1087226 SAMEA3900092-DT75; ERS1090440 or SAMEA3903306-Delftia strain 2189 filed under project number PRJEB13025. In another embodiment, the bacterial strain is *D. acidovorans* DSM-39 or SPH-1.

In vitro assays that can be used for confirming the antimicrobial activity of the purified fractions include, for example, the addition of varying concentrations of the antimicrobial composition to paper disks and placing the disks on agar containing a suspension of the pathogen of interest. Following incubation, clear inhibition zones develop around the discs that contain an effective concentration of the antimicrobial polypeptide (Liu et al. (1994) Plant Biology 91:1888-1892, herein incorporated by reference). Additionally, microspectrophotometrical analysis can be used to measure the in vitro antimicrobial properties of a composition (Hu et al. (1997) Plant Mol. Biol. 34:949-959 and Cammue et al. (1992) J. Biol. Chem. 267: 2228-2233, both of which are herein incorporated by reference). Assays that specifically measure antibacterial activity are also well known in the art. See, for example, Clinical and Laboratory Standards Institute, Guideline M7-A6, Methods for dilution antimicrobial susceptibility tests for bacteria that grow aerobically, herein incorporated by reference.

Since the agents of the present invention comprise antimicrobial properties they may be used to kill microbes.

Thus, according to another aspect of the present invention there is provided a method of killing a microbe, the method comprising contacting the microbe with the antimicrobial agents of the present invention.

According to a particular embodiment, the antimicrobial agent is a delftibactin.

In one embodiment, the delftibactin is delftibactin A (as illustrated in FIG. 41A). In another embodiment, the delftibactin is a salt of delftibactin A.

In another embodiment, the delftibactin is delftibactin B (as illustrated in FIG. 41B). In another embodiment, the delftibactin is a salt of delftibactin B.

In still another embodiment, the delftibactin has the molecular formula $C_{39}H_{68}N_{14}O_{17}$.

In yet another embodiment, the antimicrobial agent is an analog of delftibactin A or delftibactin B.

The analogue may be a naturally occurring analogue or a synthetic analogue.

Analogues of delftibactin A or B may comprise at least one, at least two, at least three, at least four, at least five, at least six, at least seven, at least eight or all of the following limitations:

1. comprise similar gene clusters to the genes that encode the enzymes (non-ribosomal peptide synthetases or NRPS) for producing delftibactin A or delftibactin B. For example, the genes that encode the enzymes for producing delftibactin A are used as the query in a BLAST search to identify similar gene clusters in other organisms.

2. similar mass spectral (MS) fragmentation pattern. In an embodiment, the significance of a match in fragmentation patterns, indicating analogous structures is calculated using computational means, for example as described in PCT Application Publication No. WO 2013/181758, the contents of which are incorporated herein by reference.

3. comprises at least two to four, or at least, three chelating amino acids. In a further embodiment, the chelating amino acids are selected from: ornithine and N-formylated, N-acetylated, N-alkylated and N-hydroxylated ornithine; ornithine lactam and N-formylated, N-acetylated, N-alkylated and N-hydroxylated ornithine lactam; serine and O-formylated, 0-acetylated and O-alkylated serine; threonine and O-formylated, 0-acetylated and O-alkylated threonine; cysteine and S-formylated, S-acetylated and S-alkylated cysteine; methionine and S-formylated, S-acetylated and S-alkylated methionine; .beta.-hydroxyaspartic acid and O-formylated, 0-acetylated and O-alkylated .beta.-hydroxyaspartic acid; histidine and N-formylated, N-acetylated, N-alkylated and N-hydroxylated histidine; arginine and N-formylated, N-acetylated, N-alkylated and N-hydroxylated arginine; glutamic acid; asparagine; tyrosine; aspartic acid; and glutamine.

4. comprises a chelation core which comprises a catechol.

5. is a non-ribosomal peptide comprising at least one N-formylated hydroxyl ornithine and optionally one or more other chemical moieties selected from N-formylated, N-acetylated, N-alkylated and N-hydroxylated ornithine; ornithine lactam and N-formylated, N-acetylated, N-alkylated and N-hydroxylated ornithine lactam; serine and O-formylated, O-acetylated and O-alkylated serine; threonine and O-formylated, O-acetylated and O-alkylated threonine and .beta.-hydroxy aspartic acid.

6. is a non-ribosomal peptide comprising 4 to 20 amino acids. In a further embodiment, the analogue is a non-ribosomal peptide comprising 5 to 15 amino acids. In a further embodiment, the analogue is a non-ribosomal peptide comprising 6 to 10 amino acids. In another embodiment, the analogue is a linear non-ribosomal peptide. In another embodiment, the analogue is a cyclic non-ribosomal peptide.

7. is a bacterial metabolite that exist and grow in the presence of soluble gold. In an embodiment, the bacteria are from the genera, Delftia, Acidovorax or Variovorax. In particular from *D. acidovorans, A. citrulli,* or *V. paradoxus*. In a further embodiment, the metabolite is at least partially secreted by the bacteria into its surrounding environment.

8. is a bacterial metabolite isolated from a bacteria comprising a nucleic acid sequence encoding non-ribosomal peptide synthetase (NRPS) operons which comprise from initiation to termination ends:

A-T-C-A-T-KS-AT-KR-T-[Var$^1$]-C-A-T-C-A-T-[Var$^2$]-C-A-T-C-A-T-[C-A-T]$_{0-3}$-[E-C-A-T]$_{0-1}$-TE, wherein: A is a adenylation domain; T is a thiolation domain; C is a condensation domain; KS is a β-ketoacyl synthetase domain; AT is an acyl transferase domain; KR is a ketoreductase domain; E is an epimerase domain; TE is a termination domain; Var$^1$ is a direct bond or C; and Var$^2$ is a direct bond or E.

9. is a compound of Formula I:

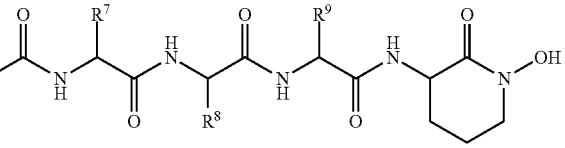

wherein R$^1$ is selected from H and $C_{1-6}$ alkyl;
R$^2$ is selected from H and $C_{1-6}$ alkyl;
R$^3$ is $(CH_2)_nC(O)OH$, unsubstituted or substituted with OH;
R$^4$ is selected from $C_{1-6}$ alkyl substituted with OH;
R$^5$ is selected from H and $C_{1-6}$ alkyl;
R$^6$ is selected from $CH_2$, $C(C_{1-6}$ alkyl$)(C_{1-6}$ alkyl$)$ and $CHC_{1-6}$ alkyl;

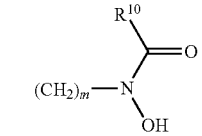

R$^7$ is
R$^8$ is selected from $C(C_{1-6}$ alkyl$)$ substituted with OH;
R$^9$ is

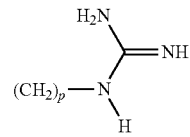

R$^{10}$ is selected from H and $C(C_{1-6}$ alkyl$)$; and n, m and p are independently selected from 1, 2, 3 and 4, or a salt thereof.

In an embodiment, $R^1$ is selected from $CH_3$ and $CH_2CH_3$. In a further embodiment $R^1$ is $CH_3$.

In an embodiment, $R^2$ is selected from $CH_3$ and $CH_2CH_3$. In a further embodiment $R^2$ is $CH_3$.

In an embodiment, $R^3$ is $(CH_2)_nC(O)OH$ substituted with OH. In a further embodiment, n is 1.

In an embodiment, $R^4$ is selected from $C_{1-4}$ alkyl substituted with OH. In another embodiment, $R^4$ is $CH(OH)CH_3$.

In an embodiment, $R^5$ is selected from H and $CH_3$. In another embodiment, $R^5$ is H.

In an embodiment $R^6$ is selected from $CH_2$, $CHCH_3$ and $CHCH_2CH_3$.

In an embodiment, $R^7$ is

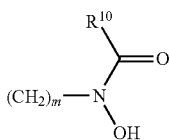

wherein m is 2 or 3 and $R^{10}$ is selected from H and $CH_3$. In a further embodiment, m is 3 and $R^{10}$ is H.

In an embodiment, $R^8$ is selected from $C_{1-2}$ alkyl substituted with OH. In a further embodiment, $R^8$ $CH_2OH$.

In an embodiment $R^9$ is

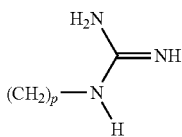

wherein p is 3 or 4. In an embodiment, p is 3.

The term "alkyl" as used herein, whether it is used alone or as part of another group, means straight or branched chain, saturated alkyl groups. The term C.sub.1-6 alkyl means an alkyl group having 1, 2, 3, 4, 5 or 6 carbon atoms.

The term "alkenyl" as used herein means straight or branched chain, unsaturated alkyl groups, that is, a saturated carbon chain that contains one or more, for example one to three, one to two or one, double bond. The term C.sub.2-6alkenylene means an alkylene group having 2, 3, 4, 5 or 6 carbon atoms.

The term "salt" as used herein means an acid addition salt or a basic addition salt. The formation of a desired compound salt is achieved using standard techniques. For example, the neutral compound is treated with an acid or base in a suitable solvent and the formed salt is isolated by filtration, extraction or any other suitable method.

The term "metallophore" as used herein refers a compound that binds to or chelates metals. The term "chelation core" as used herein refers to the groups in a metallophore that bind to a metal through the formation of two or more separate coordination bonds. A "coordination bond" is a 2-center, 2-electron bond in which the two electrons derive from the same atom.

The term "chelating amino acid" as used herein refers to an amino acid comprising a side chain with at least one chelating atom (i.e. an atom that has 2 electrons available for formation of a coordination bond). Such amino acids are those comprising at least one heteroatom in the side chain wherein the heteroatom as two electrons available for formation of a chelation bond. In an embodiment, the heteroatom is selected from, O, S and N.

The term "formylated" as used herein refers to functionalization of a compound with a formyl (C(O)H) group. For example, reference to an N-formulated amino acid refers to peptide amino acid (ribosomal or non-ribosomal) in which a side-chain amino functionality has been formulated.

The term "hydroxylated" as used herein refers to functionalization of a compound with a hydroxy (OH) group. For example, reference to an N-hydroxylated amino acid refers to peptide amino acid (ribosomal or non-ribosomal) in which a side-chain amino functionality has been hydroxylated.

The term "acetylated" as used herein refers to functionalization of a compound with a acetyl (C(O)CH$_3$) group. For example, reference to an N-acetylated amino acid refers to peptide amino acid (ribosomal or non-ribosomal) in which a side-chain amino functionality has been acetylated.

The term "alkylated" as used herein refers to functionalization of a compound with a $C_1$-6 alkyl group. For example, reference to an N-alkylated amino acid refers to peptide amino acid (ribosomal or non-ribosomal) in which a side-chain amino functionality has been alkylated.

The term "ornithine lactam" as used herein refers to the amino acid:

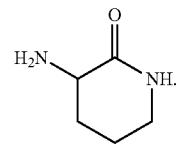

The term "N-hydroxyornithine lactam" as used herein refers to the amino acid:

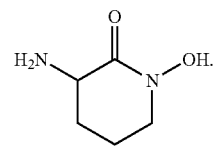

The term "β-hydroxyaspartic acid" refers to the amino acid:

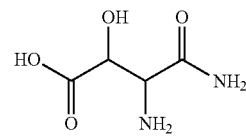

The term "catechol" as used herein refers to a compound comprising a 1,2-dihydroxybenzene group.

The term "non-ribosomal peptide" as used herein refers to a class of peptide secondary metabolites usually produced by microorganisms such as bacteria and fungi. Non-ribosomal peptides are synthesized by non-ribosomal peptide synthetases, which, unlike the ribosomes, are independent of messenger RNA. Each non-ribosomal peptide synthetase can synthesize only one type of peptide. Non-ribosomal peptides can have a linear, cyclic and/or branched structure, can contain non-proteinogenic amino acids, including D-amino acids, carry modifications like N-methyl and N-formyl groups, or are glycosylated, acetylated halogenated or hydroxylated. Cyclization of amino acids against the peptide "backbone" is often performed, resulting in oxazolines and thiazolines, and these can be further oxidized or reduced. On occasion, dehydration is performed on serines, resulting in dehydroalanine. There are many other manipulations and variations that non-ribosomal peptides can comprise, for example polyketide extensions. Non-ribosomal peptides can be dimers or trimers of identical sequences chained together or cyclized, or even branched.

According to a particular embodiment, the delftibactin analogue is a molecule illustrated in FIG. 42 (or a salt thereof).

The delftibactins (or analogues thereof) of the present application may be prepared using methods known in the art of non-ribosomal peptide synthesis or they may be isolated from a microorganism, as described in the examples section, using methods known in the art. For example, a *Delftia* bacteria may be cultured on a suitable medium and allowed to grow for a time sufficient for the desired compound to accumulate, for example about 1 to about 10 days, and the desired compound isolated from the medium using known methods. The microorganism may be a naturally occurring microorganism or a genetically modified microorganism.

Exemplary conditions for isolating delftibactin are as follows: A mobile phase being linear from 2% acetonitrile, 98% water+5 mM $(NH_4)_2CO_3$ at 2 minutes to 14% acetonitrile at 18 min at a flow rate of 3 mL/min. Delftibactin A elutes at 14.20 min and delftibactin B elutes at 17.5 min. In one embodiment a Waters Alliance 2695 RP-HPLC separations module is used, equipped with a Waters 2998 photodiode array and a Luna 5 µm C18 column (250×10.0 mm, Phenomenex).

Another method of isolating delftibactin is described in US patent application No. 20150354024, the contents of which are incorporated herein by reference.

To generate genetically modified microorganisms (for example *E. coli*) which express (and secrete) delftibactin, the microorganism is modified to express all necessary genes encoding the delftibactin-producing non-ribosomal peptide synthetases and polyketide synthetases from the del cluster (about 59 kbp in total). Other necessary genes may also be expressed such as genes of the methylmalonyl-CoA pathway (so as to provide basic substrates for the del pathway which is endogenously not present in microorganisms such as *E. coli*) PPTase and a permeability agent. Expression of delftibactin A in *E. Coli* has been described in 2013idotligemOotlorg/Team:Heidelberg/Project/Delftibactin and Dunbar, W. Scott, Trends in Biotechnology, 2017, Volume 35, Issue 1, 79-89, the contents of which is incorporated herein by reference.

As used herein the term "contacting" refers to the positioning of the agents of the present invention such that they are in direct or indirect contact with the bacterial cells. Thus, the present invention contemplates both applying the agents of the present invention to a desirable surface and/or directly to the bacterial cells.

Contacting surfaces with the agents described herein can be effected using any method known in the art including spraying, spreading, wetting, immersing, dipping, painting, ultrasonic welding, welding, bonding or adhering. The agents of the present invention may be attached to a solid surface as monolayers or multiple layers.

The present invention envisages coating a wide variety of surfaces with the agents of the present invention including fabrics, fibers, foams, films, concretes, masonries, glass, metals, plastics, polymers, and like.

An exemplary solid surface that may be coated with the agents of the present invention is an intracorporial or extracorporeal medical device or implant.

An "implant" as used herein refers to any object intended for placement in a human body that is not a living tissue. The implant may be temporary or permanent. Implants include naturally derived objects that have been processed so that their living tissues have been devitalized. As an example, bone grafts can be processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components.

Thus, for example, the present invention therefore envisions coating vascular stents with the agents of the present invention. Another possible application of the agents of the present invention is the coating of surfaces found in the medical and dental environment.

Surfaces found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; blood filters, implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherally insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, heart valves, artificial joints, artificial larynxes, otological implants), anastomotic devices, vascular catheter ports, clamps, embolic devices, wound drain tubes, hydrocephalus shunts, pacemakers and implantable defibrillators, and the like. Other examples will be readily apparent to practitioners in these arts.

Surfaces found in the medical environment include also the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

Other surfaces related to health include the inner and outer aspects of those articles involved in water purification, water storage and water delivery, and those articles involved in food processing. Thus the present invention envisions coating a solid surface of a food or beverage container to extend the shelf life of its contents.

Surfaces related to health can also include the inner and outer aspects of those household articles involved in providing for nutrition, sanitation or disease prevention. Examples can include food processing equipment for home use, materials for infant care, tampons and toilet bowls.

In addition, the agents of the present invention may have veterinary applications including disinfection of animal cages, coops or homes.

It will be appreciated that since the agents of the present invention have antimicrobial activity, the present invention contemplates use thereof for treating infection in a mammalian subject (e.g. humans).

Typically, the subjects who are treated have pathogens which cause an infection.

As used herein, the term "pathogen" refers to a microbe or microorganism such as a virus, bacterium, prion or fungus that causes a disease (e.g. a respiratory disease).

According to a particular embodiment, the pathogen is a human pathogen.

Exemplary pathogenic viruses may belong to the following families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae. Particular pathogenic viruses contemplated by the present invention are those that cause smallpox, influenza, mumps, measles, chickenpox, ebola, or rubella.

According to a particular embodiment, the virus is one which brings about a respiratory infection (e.g. an upper respiratory tract infection and/or a lower respiratory tract infection).

Thus, according to a particular embodiment, the pathogenic virus is an influenza virus (e.g. influenza virus A—(e.g. H1N1, H2N2, H3N2, H5N1, H7N7, H1N2, H9N2, H7N2, H7N3, H10N7 and H7N9), influenza virus B or influenza virus C).

In another embodiment, the pathogenic virus is a parainfluenza virus (hPIV) including the human parainfluenza virus type 1 (hPIV-1) (causes croup); the human parainfluenza virus type 2 (hPIV-2) (causes croup and other upper and lower respiratory tract illnesses), the human parainfluenza virus type 3 (hPIV-3) (associated with bronchiolitis and pneumonia) and the human parainfluenza virus type 4 (hPIV-4).

In yet another embodiment, the pathogenic virus is a respiratory syncytial virus (RSV).

Exemplary pathogenic bacteria include *Mycobacterium tuberculosis* which causes tuberculosis, *Streptococcus* and *Pseudomonas* which cause pneumonia, and *Shigella*, *Campylobacter* and *Salmonella* which cause foodborne illnesses. Other exemplary pathogenic bacteria contemplated by the present invention are those that cause infections such as tetanus, typhoid fever, diphtheria, syphilis and Hansen's disease.

According to a particular embodiment, the pathogenic bacteria is *E. coli, Pseudomonas aeruginosa, Klebsiella pneumonia, Enterococcus faecalis, Staphylococcus aureus* (MS SA, MRSA), *Salmonella enteritidis, Serratia marcescens*, a pathogenic bacteria listed in Table 1 of the Examples section herein below or illustrated in FIG. 21 and FIGS. 31-33.

According to one embodiment, the agents are used to treat a topical infection (i.e. infection of the skin) and are provided in a topical formulation.

According to another embodiment, the agents are used to treat an infection inside the body. In this case, the agents may be provided ex vivo or in vivo.

According to one embodiment, the infection is an acute infection.

According to another embodiment, the infection is a chronic infection.

The antimicrobial agent of the present invention (e.g. delftibactin) may be used (either in vivo or ex vivo) in conjunction with an antibiotic or an antimicrobial peptide.

Examples of antibiotics contemplated by the present invention include, but are not limited to Daptomycin; Gemifloxacin; Telavancin; Ceftaroline; Fidaxomicin; Amoxicillin; Ampicillin; B acampicillin; Carbenicillin; Cloxacillin; Dicloxacillin; Flucloxacillin; Mezlocillin; Nafcillin; Oxacillin; Penicillin G; Penicillin V; Piperacillin; Pivampicillin; Pivmecillinam; Ticarcillin; Aztreonam; Imipenem; Doripenem; Meropenem; Ertapenem; Clindamycin; Lincomycin; Pristinamycin; Quinupristin; Cefacetrile (cephacetrile); Cefadroxil (cefadroxyl); Cefalexin (cephalexin); Cefaloglycin (cephaloglycin); Cefalonium (cephalonium); Cefaloridine (cephaloridine); Cefalotin (cephalothin); Cefapirin (cephapirin); Cefatrizine; Cefazaflur; Cefazedone; Cefazolin (cephazolin); Cefradine (cephradine); Cefroxadine; Ceftezole; Cefaclor; Cefamandole; Cefmetazole; Cefonicid; Cefotetan; Cefoxitin; Cefprozil (cefproxil); Cefuroxime; Cefuzonam; Cefcapene; Cefdaloxime; Cefdinir; Cefditoren; Cefetamet; Cefixime; Cefmenoxime; Cefodizime; Cefotaxime; Cefpimizole; Cefpodoxime; Cefteram; Ceftibuten; Ceftiofur; Ceftiolene; Ceftizoxime; Ceftriaxone; Cefoperazone; Ceftazidime; Cefclidine; Cefepime; Cefluprenam; Cefoselis; Cefozopran; Cefpirome; Cefquinome; Fifth Generation; Ceftobiprole; Ceftaroline; Not Classified; Cefaclomezine; Cefaloram; Cefaparole; Cefcanel; Cefedrolor; Cefempidone; Cefetrizole; Cefivitril; Cefmatilen; Cefmepidium; Cefovecin; Cefoxazole; Cefrotil; Cefsumide; Cefuracetime; Ceftioxide; Azithromycin; Erythromycin; Clarithromycin; Dirithromycin; Roxithromycin; Telithromycin; Amikacin; Gentamicin; Kanamycin; Neomycin; Netilmicin; Paromomycin; Streptomycin; Tobramycin; Flumequine; Nalidixic acid; Oxolinic acid; Piromidic acid; Pipemidic acid; Rosoxacin; Ciprofloxacin; Enoxacin; Lomefloxacin; Nadifloxacin; Norfloxacin; Ofloxacin; Pefloxacin; Rufloxacin; Balofloxacin; Gatifloxacin; Grepafloxacin; Levofloxacin; Moxifloxacin; Pazufloxacin; Sparfloxacin; Temafloxacin; Tosufloxacin; Besifloxacin; Clinafloxacin; Gemifloxacin; Sitafloxacin; Troyafloxacin; Prulifloxacin; Sulfamethizole; Sulfamethoxazole; Sulfisoxazole; Trimethoprim-Sulfamethoxazole; Demeclocycline; Doxycycline; Minocycline; Oxytetracycline; Tetracycline; Tigecycline; Chloramphenicol; Metronidazole; Tinidazole; Nitrofurantoin; Vancomycin; Teicoplanin; Telavancin; Linezolid; Cycloserine 2; Rifampin; Rifabutin; Rifapentine; B acitracin; Polymyxin B; Viomycin; Capreomycin.

According to a particular embodiment, the antibiotic is clarithromycin or rifampicin on VRE.

In one preferred embodiment, the amount of the antibiotic (when used in combination with the anti-microbial agent of the present invention) is below the minimum dose required for therapeutic or prophylactic effectiveness when used as a single therapy (e.g. 10-99%, preferably 25 to 75% of that minimum dose). This allows for reduction of the side effects caused by the antibiotic but the therapy is rendered effective because in combination with the antimicrobial agent of the present invention, the combinations are effective overall. Alternatively, the combination of the two agents may allow for long-term use without building up resistance.

In another embodiment, the amount of the anti-microbial agent (when used in combination with the antibiotic of the present invention) is below the minimum dose required for therapeutic or prophylactic effectiveness when used as a single therapy (e.g. 10-99%, preferably 25 to 75% of that minimum dose). This allows for reduction of the side effects caused by the antibiotic but the therapy is rendered effective because in combination with the antimicrobial agent of the present invention, the combinations are effective overall. Alternatively, the combination of the two agents may allow for long-term use without building up resistance.

According to one embodiment, the anti-microbial agent is administered prior to the antibiotic. In another embodiment, the anti-microbial agent is administered following administration of the antibiotic.

In still another embodiment, the anti-microbial agent is administered concomitantly with the antibiotic. In this embodiment, the anti-microbial agent may be administered in the same composition (i.e. co-formulated in a single composition, or may be coated on the same surface, as further described herein above).

Since it is known that Delftibactins bind with high affinity to metals such as gold or gallium, the present inventors further contemplate using delftibactin which is attached to such metals for enhancing its antimicrobial properties. Both gallium and gold are known for their antimicrobial properties—see for example Antunes et al., Antimicrob. Agents Chemother. November 2012 vol. 56 no. 11 5961-5970; and Zhou et al., J Nanobiotechnology. 2012; 10: 19.

The present invention contemplates contacting cells with the agents per se or as part of a pharmaceutical composition.

In one embodiment, the pharmaceutical compositions of the present invention are administered to a subject in need thereof in order to prevent or treat a bacterial infection.

As used herein, the term "subject in need thereof" refers to a mammal, preferably a human subject.

As used herein, the term "treating" refers to curing, reversing, attenuating, alleviating, minimizing, suppressing or halting the deleterious effects of a pathogen infection.

The phrase "pharmaceutical composition", as used herein refers to a preparation of one or more of the active ingredients described herein with other chemical components such as physiologically suitable carriers and excipients. The purpose of a pharmaceutical composition is to facilitate administration of a compound to an organism.

As used herein the term "active ingredient" refers to the agents of the present invention accountable for the intended biological effect.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences", Mack Publishing Co., Easton, Pa., which is herein fully incorporated by reference and are further described herein below.

It will be appreciated that the agents of the present invention can be provided to the individual with additional active agents to achieve an improved therapeutic effect as compared to treatment with each agent by itself.

Exemplary additional agents include antibiotics (e.g. rifampicin, chloramphenicol and spectinomycin), antibacterial peptides, antivirals, antifungals etc.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added.

All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The preparation of the present invention may also be formulated as a topical compositions, such as a spray, a cream, a mouthwash, a wipe, a foam, a soap, an oil, a solution, a lotion, an ointment, a paste and a gel.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

As mentioned, the *Delftia* strains that secrete the antimicrobial agents of the present invention were uncovered based on their ability to propagate in a *Delftia* selective agar.

Thus, according to another aspect of the present invention there is provided a culture medium comprising:

(i) $KH_2PO_4$;
(ii) $(NH_4)_2SO_4$;
(iii) $MgSO_4$; and
(iv) Phthalic acid (e.g. 0.1-5%—e.g. about 0.5%).

The culture medium of the present invention may be in a liquid form or a solid form (e.g. may be combined with agar).

Preferably, the culture medium further comprises antibiotics (e.g. ampicillin and/or Gentamicin).

Using the culture medium described herein above, the present inventors uncovered novel strains of *Delftia* bacteria.

Thus, according to still another aspect of the present invention there is provided a cell culture comprising a culture medium and a *Delftia* bacteria having a genome which comprises a polynucleotide sequence filed in the European Nucleotide Archive (ENA) under the Accession no. ERS1087230, SAMEA3900096-DT123; ERS1087231, SAMEA3900097-DT2361; ERS1087229, SAMEA3900095-DT122; ERS1087228, SAMEA3900094-DT120; ERS1087227, SAMEA3900093-DT119; ERS1087226 SAMEA3900092-DT75; or ERS1090440, SAMEA3903306-*Delftia* strain 2189.

In one embodiment, the culture medium is the novel culture medium described herein above—i.e. comprises:

(i) $KH_2PO_4$;
(ii) $(NH_4)_2SO_4$;
(iii) $MgSO_4$; and
(iv) Phthalic acid (e.g. 0.1-5%—e.g. about 0.5%).

In preferred embodiments, the culture medium is sterile.

As used herein the term "about" refers to ±10% The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Swarm agar assay: *E. coli* MC4100/pKB2690 (expressing mcherry) and *Delftia* strain 75 were inoculated on swarm agar at distance of 1 cm one from the other, and incubated for 48 hours at 30° C.

Perpendicular swarm agar assay: *S. aureus, E. coli, Enterococcus faecalis, Pseudomonas aeruginosa, Salmonella Enteritidis*, and *Klebsiella pneumonia* were spread on swarm agar perpendicular to *Delftia* strains 2189 or 75. The plates were incubated at 30° C. for 24 hours. Sample from the contact point with strain 75, and away from it were used for gram staining and microscopic examination.

Generation of supernatant from *Delftia*: 0.5 McF (McFarland standards as measured by Nephelometer or densitometer) of overnight culture *S. aureus* MRSA (USA300 a pandemic clinical isolate) was prepared in 1 ml NB. 1 ml of clear supernatant from 3 days of standing strain 2189, or NB (control) was added to the tubes. At the indicated time periods, withdrawn samples were diluted and plated on plate count agar for colony counting.

Contact dependent inhibition assay: One half of a culture dish was inoculated with *Delftia* Strain 2189. A 0.45 μm filtration membrane placed over the plate and various *E. coli* strains were spread using a cotton swab in the direction of the white arrow.

Utilization of the E. coli biosensor array for measuring toxic activity in *Delftia* supernatant: *Delftia* strain 2189 was incubated in 3 ml tube for 3 days at 30° C. without shaking. A clear supernatant collected by centrifugation and filtration of the cultures using 0.45 μm filtration membrane was used for this experiment. X-axis indicates the amount of 2189 supernatant that was added to the *E. coli* reporter strains, in 96 wells plate. The plate was incubated in GENios (TECAN), at 37° C. for 6 hours. Every 10 min the plate was shaken and the bioluminescence was recorded. The graph displays the maximal ratio of promoter activation for each volume of supernatant (relative to the constitutive strain *E. coli* MG/CP38).

Optimization of secretion conditions for the *E. coli* biosensor: *Delftia* strain 75 was incubated in 3 ml tube for 3 or 6 days at 30° C. without shaking. A clear supernatant collected by centrifugation and filtration of the culture using 0.45 μm filtration membrane was used for the experiment. The indicated diluted medium (×2, ×4, ×8 etc.) was added to *E. coli* MG/sodA reporter strain. The maximal activity was gained following 3 days of incubation as indicated by sodA activation. The induction of the sodA promoter is in direct correlation to the amount of strain 75 supernatant. Similar results were obtained for strains 2189 and 2350.

Size characterization of the active compounds: In order to elucidate the size of the molecules of the active fraction, *Delftia* clones 75 and 2189 were inoculated into 0.5 L Erlenmeyer flask with 100 ml NB for 3 day in 30° C. without shaking. Clear supernatants were collected as follows: the 3 day culture was centrifuged at 3,500 g for 10 min at 4° C., and the clear supernatant (total supernatant) was filtered through a 0.45 μm membrane. The total supernatant was uploaded into a 10-kDa Amicon filter and centrifuged at 4,000 g for 15 min at 4° C. The activity of the upper unfiltered fraction and the flow-through were examined for inhibitory activity against MRSA strain USA300. A 3-kDa Amicon filter and a 1-kDa Amicon filter were also used in subsequent experiments.

Resistance to RNAse A and DNAse I: 1 ml of strain 75 supernatant was incubated with 10 μg/ml RNase A (Sigma) for 15 min at 60° C. A control supernatant was incubated as described without RNase A. At the end of the incubation the RNase A was removed from the sample by uploading the supernatant onto 3 kDa Amicon filters and cold centrifugation. The flow-through was used in the experiment. The sensitivity to DNase 1 was tested by addition of 25 μl DNase-1 (Qiagen kit 79254) to 1 ml of strain 75 supernatant and incubation for 10 min at room temperature. A control tube was incubated as described. The enzyme was removed from the media using the 3-kDa Amicon membranes. The OD600 of USA300 cultures was measured after 6 hour of incubation at 37° C., shaking.

Resistance to proteinase K: Total supernatant from clone 75 was used in this experiment. Proteinase K was added to the indicated sample to the final concentration of 100 μg/ml. All the samples were incubated at 50° C. for 15 min. At the end of the incubation time, all the samples were uploaded onto 3-kDa Amicon (this step also removes proteinase K from the sample). The antimicrobial activity was tested against MRSA USA300 and *Acinetobacter baumannii* (ACB).

Reverse phase SEP-PAK tC18 columns: Source material: clone 75 fraction <3 kDa. Prior to loading of the sample to the Sep-Pak column, the pH of the sample was adjusted to 3 using trifluoroacetic acid (TFA). Columns were pre-conditioned with 100% acetonitrile and washed with water. Samples were loaded onto the column with a flow rate of 1 drop per second. Flow through was discarded. Washing the column of unwanted components was performed with water. Elution of the fractions into 1.5 ml Eppendorf tubes was performed with a gradient of 0%, 2%, 4%, 6%, 8%, 10%, 12% and 14% acetonitrile (ACN) with 0.05% TFA. The Eppendorf tubes were placed in speed vacuum instrument at 50° C. until the samples were dry. For activity assay the pellets were rehydrated in PBS. The activity in different fractions was measured against MRSA USA300.

Viability assays on primary human cells: Supernatant collected from *Delftia* strain 2189 was added to a fresh culture of primary human kidney cell in different dilutions (,1:10,1:5,1:1 1:500, 1:100, 1:50) for 3, 4 and 7 days in triplicates using MTS assay to measure cell proliferation.

Nutrient broth medium was used as negative control for cytotoxicity, while untreated cells were used as a negative control (cultivated with DMEM only). Primary human kidney tubular epithelial cells were grown in 96-well cell culture plates ($1\times10^4$/well) and in DMEM containing ampicillin and streptomycin and supplemented with 10% fetal bovine serum at 37° C. and 5% $CO_{2/95}$% air until confluent. 2189 supernatant medium was added, and cell viability was evaluated by absorbance at 480 nm.

5,000 cells (human melanoma) were seeded in 96 well plate together with 5 ul of 2189 sup which was diluted to different concentrations (1:1=no dilution, 1:10, 1:100) for 1-3 days. The cells were FACS analyzed for the existence of dead cells by PI staining.

Production of biofilm by *Delftia* strain 2189 in response to various toxic compounds: *Delftia* strain 2189 was incubated in 1 ml NB containing the indicated concentration of toxic compounds, for 24 hours at 30° C. with no shaking. 8 μl samples were used for phase contrast microscopy.

Swarming, production of fruiting bodies and spores by *Delftia* strain 2189: A. *Delftia* strain 2189 was inoculated at the center of swarm agar and incubated at 30° C. for 6 days. The colonies were examined using Leica motorized binocular. Samples from fresh cultures as well as fruiting bodies producing colonies were withdrawn for gram staining and microscopic examination (FB-fruiting bodies).

Preparation of DSA: Into a 2 L flask, 1 L of sterile mineral water was added together with the following compounds:

| | |
|---|---|
| K2HPO4(s) | 3.5 gr, |
| KH2PO4(s) | 1.5 gr, |
| (NH4)2SO4(s) | 1 gr |
| MgSO4*7H2O(s) | 0.2 gr |
| Phthalic acid(s) | 0.2 gr |
| Agar(s) | 1.5 gr |

The flask was placed on a hot plate with a magnetic stirrer and heated until boiling. After autoclaving and cooling to 45° C. an antibiotic cocktail was added (ampicillin 200 microgram/ml & gentamicin 50 microgram/ml), the pH was adjusted to 7 and the media was poured into 90 millimeter petri dishes.

Results

*Delftia* sp. are able to swarm on "swarm agar" containing low agar concentration. The cells propagate in two distinct waves: the front (fast) wave and the lagging wave that comprises the majority of the colony biomass (FIG. 1A).

When *Delftia* was seeded with another strain (e.g. *E. coli*) on the same swarm agar plate, *Delftia* cells swarm towards the target colony. This unique type of chemotaxis is termed predataxis. After reaching the target colony, *Delftia* enclose and lyse the cells (FIG. 1C).

By spreading the target bacteria perpendicular to the Delftia, it was observed that different clones of Delftia respond in different methods to the presence of target cells (FIGS. 2A-B). Using this new assay, the present inventors examined the predataxis behavior of several Delftia isolates against the following bacteria: E. coli, Pseudomonas aeruginosa, Klebsiella pneumonia, Enterococcus faecalis, Staphylococcus aureus (MSSA, MRSA), Salmonella enteritidis and Serratia marcescens. The level of killing was examined by sampling target cells, from the contact point, with a small inoculation loop and spreading it over a new agar plate (Table 1). Similar samplings were applied for gram stain and microscopic examination. In contrast to clones 2350, 2189 and 75, strain T7 did not display clear predataxis behavior. None of the clones were able to inhibit Serratia marcescens. Clones 2350, 2189 and 75 exhibit partial inhibitory effect against Pseudomonas aeruginosa and Klebsiella pneumonia. All of them were effective in killing various E. coli and S. aureus strains (MSSA, MRSA, including the pandemic strain USA300) as well as Enterococcus faecalis. Interestingly, the microscopic examination reveals that S. aureus cells from the contact point with Delftia appear mostly as gram negative, indicating lysis of the cell wall. Furthermore, the cells lose their typical "bunch of grapes"-like appearance. The tested Pseudomonas aeruginosa ATCC 9027 is highly resistant to beta-lactams, Trim/Sulfa and nitrofurantoin, and Delftia strains 2189, 75 and 2350 were able to overcome its resistance mechanisms. In conclusion, Delftia strains 2189, 75 and 2350 are effective at inhibition of various key pathogens, including gram positive and gram negative bacteria.

TABLE 1

Summary of the inhibitory effect of various strains of Delftia clones against key pathogens. The antimicrobial activity of strains 75, 2189 and 2350 is higher than of the Japanese D. tsuruhatensis strain T-7.

| Target strains | Inhibition by Delftia strains (YES/NO/Partial) Delftia strains | | | |
|---|---|---|---|---|
| | 2189 | 2350 | 75 | T-7 |
| Serratia marcescens | NO | NO | NO | NO |
| Enterococcus faecalis ATCC 29212 | YES | YES | YES | NO |
| Salmonella enterica Enteritidis ATCC 13076 | YES | YES | YES | NO |
| Klebsiella pneumoniae ATCC 13883 | Partial | Partial | Partial | NO |
| Staphylococcus aureus MSSA (clinical isolate) | YES | YES | YES | NO |
| Staphylococcus aureus MRSA (USA300) | YES | YES | YES | NO |
| Staphylococcus aureus ATCC 25923 | YES | YES | YES | NO |
| Pseudomonas aeruginosa ATCC 9027 | Partial | Partial | Partial | NO |
| Escherichia coli ATCC 25922 | NO | nd | NO | NO |
| Escherichia coli MC 4100 | YES | YES | YES | YES |
| Escherichia coli J5-3 | YES | YES | YES | YES | nd—not determined

Antibacterial activity of Delftia: Clear supernatant was found to be toxic to growing S. aureus cells, by significantly reducing viable cell count after 5 hours of incubation (FIG. 3A).

The supernatant of 2189 (FIG. 37) and 75 (FIG. 38) were also found to be potent against Acinetobacter baumannii 179. The 2189 supernatant further inhibited growth of all tested multidrug resistant and extensively drug resistant Acinetobacter baumannii MDR/XDR ACB strains (FIG. 39).

Delftia supernatants were also found to cause elongation of generation time in Pseudomonas aeruginosa (FIG. 40).

In a different experiment, a 0.45 μm membrane was used to separate E. coli J5-3 from Delftia strain 2350 (FIG. 3B). The membrane is impermeable to bacteria but allows free diffusion of small molecules. The E. coli J5-3 separated by the membrane from strain 2350 was significantly inhibited by this strain, while direct contact induces complete inhibition of the target cells. These results indicate that the antibacterial activity of Delftia sp. may be a combination of at least two different mechanisms that act synergistically— secretion of toxic compounds and contact dependent inhibition.

Analysis of bacterial array with reporter genes sensitive to various stress signals: As a quantitative indication of the toxic effects of Delftia supernatants, a biosensor array composed of 12 E. coli strains containing different reporter plasmids was used (Yagur-Kroll et al., 2011, Analytical and bioanalytical chemistry, 400, 1071-1082). Exposure of the reporter strain to various types of stresses i.e. oxidative stress, membrane, protein and DNA damages result in specific promoter activation and emission of light. The intensity of the signal is proportional to the concentration of the toxic compounds.

A significant increase in the expression of sodA and micF that are activated by superoxide damage and oxidative stress was observed upon exposure of the biosensor array to supernatant collected from various Delftia strains (for example see FIG. 4A for strain 2189). Notably, the micF gene is also activated by antibacterial cationic peptides. Furthermore, significant activation was also noticed for arsR, marR and yqjF genes. marR is activated by antibiotics and chemicals with phenolic ring and yqjF is activated by specific nitro and phenolic compounds. The activation of the indicated genes is dose dependent. The most active strains in this assay are 75 and 2189.

Interestingly, supernatant collected from strain T-7 displayed significantly lower induction of these genes. The biosensor array was found as a useful means for optimization of the secretion conditions (shaking/standing, for 3/6, days respectively). The highest activity was detected following 3 days of incubation at 30° C. with no shaking (FIG. 4B).

Temperature regulation for the production of antimicrobial compounds by Delftia: The secreted activity of strains 75 and 2189 was tested at the indicated temperatures. Delftia cultures of both strains were incubated for 3 days at 30° C. or at 37° C. At the end of the incubation the media were centrifuged to remove insoluble matter and the cleared supernatants were filtrated through a 0.45 micrometer filter. The activity of the sterile supernatants against Acinetobacter baumanii is displayed in FIGS. 4C-D. While more than two log reduction in the viable counts of Acinetobacter baumannii that was exposed to the 30° C. media, no reduction in the viable counts occurred following exposure to media produced from Delftia culture incubated at 37° C.

Size characterization of the active compounds: As shown in FIG. 5A, most of the activity is present in the flow-through fraction that is smaller than 10 kDa. Interestingly, this activity is significantly higher than that of the total supernatant, which may indicate higher specific activity by size purification. The activity of the smaller than 10 kDa fraction was confirmed against Acinetobacter baumannii (FIG. 5B). Although most of the activity is in the fraction smaller than 10 kDa, some activity was also observed in the fraction larger than 10 kDA.

In order to further elucidate the size of the active compound, the present inventors applied essentially the same strategy as displayed above, except they now used a 3-kDa Amicon membrane filter apparatus. From FIGS. 5C-D, it may be concluded that the active compounds are smaller than 3-kDa.

In the next step, 1 kDa dialysis membranes were filled with total supernatant of strain 75. The dialysis membranes were put in a container with PEG800 for 1 hour at 4° C. This protocol enabled concentration of the medium fivefold. As shown in FIG. 5E, the activity of the supernatant which was retained inside the membrane was significantly increased. For example, 6% supernatant had no inhibition effect on USA300 growth compared to NB only, whereas 6% supernatant which was retained in the dialysis membrane effectively inhibited the target bacterial growth. In conclusion, using various fractionation experiments it may be concluded that the size of the active compounds are between 1000-3000 Daltons.

Biochemical characterization of the active fraction: In order to gain insight into the chemical entity of the active compounds, the present inventors applied various treatments to the active fractions namely by exposing these fractions to heat, proteinase K and nucleases. As shown if FIG. 6 there is no reduction in the antimicrobial activity after treatment with RNase A or DNase-1. Furthermore, no reduction in antimicrobial activity of the supernatants after incubation at 85° C. for 30 min was detected. In addition, proteinase K did not affect the compound activity either, as shown in FIG. 7. Taken together, it may be concluded that the active compounds are not proteins or nucleic acids.

In order to further purify the active compounds a reverse phase Sep-Pak tC18 column was used. Various fractions were eluted from the column by gradually increasing the gradient of acetonitrile/water. As shown in FIG. 8, most of the activity was eluted with 6% acetonitrile.

Production of antimicrobial compounds in minimal defined media: The production of antimicrobial active molecules was analyzed in a minimal defined media, namely, Davis medium (Davis, BD catalogue number 275610) with 0.5% or 1% glycerol. Maximal activity was detected after 8-13 days of incubation at 30° C., standing. FIGS. 9A-C demonstrate the potency of the supernatants from strains 2189 and 75 grown in minimal defined medium during 8 days, against the target bacteria MRSA USA300 and *Acinetobacter baumannii* (ACB).

HPLC characterization of the active fractions of strains 75 and 2189 produced in defined minimal medium: Strains 75 and 2189 were inoculated into defined media plus 0.5% glycerol for 8 days at 30° C. standing. Clear supernatant was produced by centrifugation to remove cell pellets, filtered through 0.45 micron and 3 kDa Amicon purification system as described previously. Lyophilized fractions were injected into Hitachi Lachrom HPLC apparatuses with C-18 column. Fractions were separated by gradual increasing of acetonitrile/water concentrations (10, 20, 30, 40% ACN) and 0.1% TFA. The signals were detected by diode array detector. Two wavelengths 220 and 280 nm were used to detect the peaks. Fractions were collected using a fraction collector. Comparison of the spectra is demonstrated in FIG. 10.

There are a few peaks that differentiate between the spectra of the strains indicating production of strain-specific compounds. Antimicrobial activity of the different fractions indicate that the activity is concentrated in fractions 1-4 min of strains 75 and 2189 and 5-7 min in the supernatant of strain 2189 (FIGS. 11A-D).

The active supernatants were then analyzed using a finer gradient (0-15% ACN) and collected fraction every minute. The chromatogram analysis is displayed in FIG. 12. Peaks that were common to strains 75 and 2189 were observed as well as peaks that were strain specific. The summary of the peaks detected from the two strains is displayed in FIG. 13. The activity of the HPLC fractions from strains 2189 and 75 respectively is displayed in FIGS. 14A-D. Fractions 3-4 min are active in both strains, noteworthy that fraction 11-12 min is active in 2189 and 10-11 min in 75.

Furthermore, spectral analysis of the active fractions from strains 75 and 2189 indicated that in each fraction there are unique compounds characterized by a unique absorbance spectrum (FIGS. 15 and 16). It may be concluded that strains 2189 and 75 produce a library of different antimicrobial compounds.

LCMS analysis of active fractions: The active fractions as well as the non-active fractions, which were eluted using preparative HPLC were further analyzed using LC-MS. Overall 148 compounds were determined in the analysis. 88 compounds appeared in four active fractions. Tables 2-5 display the compounds present in the active fractions which received scores 70 and higher that is considered to be a high score. The relative amounts of the molecules in the fractions are expressed as vol %.

The formulas given to the compounds are suggestions given by the analysis program according to the mass data. Several known compounds were suggested by the database, most of these compounds are not known of having antimicrobial activity. The name of the compound was based on screening the mass against about 30,000 compounds library.

Nevertheless, fraction 11-12 from strain 2189, identified gentamycin, monensin and netilmicin at very low quantities—however, in the other three active fractions no known antimicrobial compounds were identified.

TABLE 2

LCMS analysis of active fraction 11-12 min from strain 2189

| Cpd | Label | Name | Formula | Score | Mass | Avg Mass | Std Dev | Base Peak | m/z | Vol % | Fraction |
|---|---|---|---|---|---|---|---|---|---|---|---|
| 59 | Cpd 59: Misoprostol | Misoprostol | C22 H38 O5 | 92.25 | 382.2736 | 382.5827 | 0.0005 | 400.3074 | 400.3074 | 9.59 | DT2189__11-12 min |
| 57 | Cpd 57: C25 H41 N5 O2 | | C25 H41 N5 O2 | 97.66 | 443.3259 | 443.6592 | | 444.3336 | 444.3336 | 6.08 | DT2189__11-12 min |
| 27 | Cpd 27: C13 H28 O4 | | C13 H28 O4 | 96.07 | 248.1991 | 248.4017 | 0.0021 | 249.2042 | 249.2042 | 4.81 | DT2189__11-12 min |
| 43 | Cpd 43: C21 H46 N3 O3 P | | C21 H46 N3 O3 P | 98.48 | 419.3274 | 419.6344 | | 420.3346 | 420.3346 | 4.42 | DT2189__11-12 min |

TABLE 2-continued

LCMS analysis of active fraction 11-12 min from strain 2189

| Cpd | Label | Name | Formula | Score | Mass | Avg Mass | Std Dev | Base Peak | m/z | Vol % | Fraction |
|---|---|---|---|---|---|---|---|---|---|---|---|
| 9 | Cpd 9: C16 H28 N4 O2 | | C16 H28 N4 O2 | 96.26 | 308.2209 | 308.4851 | 0.0007 | 309.2282 | 309.2282 | 4.27 | DT2189_11-12 min |
| 61 | Cpd 61: C19 H38 N3 O P | | C19 H38 N3 OP | 96.83 | 355.2746 | 355.5319 | | 356.282 | 356.282 | 4.25 | DT2189_11-12 min |
| 4 | Cpd 4: C23 H45 N5 O8 | | C23 H45 N5 O8 | 97.52 | 519.3277 | 519.658 | | 520.3349 | 520.3349 | 4.06 | DT2189_11-12 min |
| 21 | Cpd 21: C14 H31 N | | C14 H31 N | 97.35 | 213.2464 | 213.4182 | | 214.2537 | 214.2537 | 3.55 | DT2189_11-12 min |
| 5 | Cpd 5: C24 H50 N7 O6 P | | C24 H50 N7 O6 P | 96.64 | 563.3551 | 563.7062 | | 564.3625 | 564.3625 | 3.31 | DT2189_11-12 min |
| 40 | Cpd 40: C20 H34 S | | C20 H34 S | 85.37 | 306.2381 | 306.4556 | | 307.2444 | 307.2444 | 3.21 | DT2189_11-12 min |
| 56 | Cpd 56: C27 H45 N5 O3 | | C27 H45 N5 O3 | 97.08 | 487.3524 | 487.7039 | | 488.3593 | 488.3593 | 2.87 | DT2189_11-12 min |
| 39 | Cpd 39: C11 H34 N9 P | | C11 H34 N9 P | 87.77 | 323.2678 | 323.5149 | | 324.2752 | 324.2752 | 2.73 | DT2189_11-12 min |
| 12 | Cpd 12: C19 H34 N4 O3 | | C19 H34 N4 O3 | 97.3 | 366.2632 | 366.5301 | 0.0006 | 384.2963 | 384.2963 | 2.65 | DT2189_11-12 min |
| 6 | Cpd 6: C26 H54 N7 O7 P | | C26 H54 N7 O7 P | 97.21 | 607.3816 | 607.7553 | | 608.3891 | 608.3891 | 2.59 | DT2189_11-12 min |
| 19 | Cpd 19: Octamylamine | Octamylamine | C13 H29 N | 96.45 | 199.2308 | 199.3988 | | 200.2382 | 200.2382 | 2.21 | DT2189_11-12 min |
| 3 | Cpd 3: Netilmicin | Netilmicin | C21 H41 N5 O7 | 93.93 | 475.3003 | 475.5785 | | 476.307 | 476.307 | 2.02 | DT2189_11-12 min |
| 41 | Cpd 41: C25 H45 N5 O3 | | C25 H45 N5 O3 | 96.44 | 463.3525 | 463.7042 | | 464.3597 | 464.3597 | 1.98 | DT2189_11-12 min |
| 38 | Cpd 38: Toprilidine | Toprilidine | C19 H25 N3 O | 90.58 | 311.1991 | 328.4247 | | 329.2329 | 329.2329 | 1.68 | DT2189_11-12 min |
| 17 | Cpd 17: C19 H36 N3 O8 P | | C19 H36 N3 O8 P | 96.68 | 465.2232 | 465.5423 | | 466.2307 | 466.2307 | 1.57 | DT2189_11-12 min |
| 45 | Cpd 45: C20 H41 N O5 | | C20 H41 N O5 | 89.7 | 375.2972 | 375.5957 | | 376.3042 | 376.3042 | 1.53 | DT2189_11-12 min |
| 35 | Cpd 35: C17 H34 N2 O3 | | C17 H34 N2 O3 | 92.19 | 314.2584 | 314.5389 | 0.0012 | 315.2657 | 315.2657 | 1.51 | DT2189_11-12 min |
| 55 | Cpd 55: C27 H54 N3 O5 P | | C27 H54 N3 O5 P | 97.78 | 531.3794 | 531.7228 | | 532.3868 | 532.3868 | 1.50 | DT2189_11-12 min |
| 7 | Cpd 7: Monensin | Monensin | C36 H62 O11 | 80.6 | 670.4263 | 651.8188 | | 652.4158 | 652.4158 | 1.48 | DT2189_11-12 min |
| 51 | Cpd 51: C13 H39 N11 S | | C13 H39 N11 S | 93.45 | 381.3103 | 381.5886 | | 382.3173 | 382.3173 | 1.47 | DT2189_11-12 min |
| 22 | Cpd 22: Mepronil #55814410 | Mepronil #55814410 | C12 H19 N O2 | 82.66 | 209.1422 | 191.2867 | | 192.1388 | 192.1388 | 1.38 | DT2189_11-12 min |
| 18 | Cpd 18: C22 H43 N5 O4 | | C22 H43 N5 O4 | 82.78 | 441.331 | 441.5278 | | 442.3383 | 442.3383 | 1.30 | DT2189_11-12 min |
| 10 | Cpd 10: Suxamidofyllin | Suxamidofyllin | C17 H25 N5 O5 | 97.26 | 379.1857 | 379.4368 | | 380.1928 | 380.1928 | 1.17 | DT2189_11-12 min |
| 37 | Cpd 37: C15 H34 N3 P | | C15 H34 N3 P | 93.68 | 287.248 | 287.4598 | 0.0005 | 288.2554 | 288.2554 | 1.15 | DT2189_11-12 min |
| 8 | Cpd 8: C12 H26 O5 | | C12 H26 O5 | 74.29 | 250.1789 | 250.4196 | 0.0004 | 251.1867 | 251.1867 | 1.05 | DT2189_11-12 min |
| 24 | Cpd 24: C21 H34 N6 O | | C21 H34 N6 O | 95.41 | 386.28 | 386.5604 | 0.0018 | 387.2875 | 387.2875 | 1.02 | DT2189_11-12 min |
| 14 | Cpd 14: Lauroguadine | Lauroguadine | C20 H36 N6 O | 91.46 | 376.2939 | 358.5939 | | 359.2908 | 359.2908 | 0.98 | DT2189_11-12 min |
| 31 | Cpd 31: C15 H26 O4 | | C15 H26 O4 | 86.44 | 270.1816 | 270.4422 | | 271.1891 | 271.1891 | 0.92 | DT2189_11-12 min |

TABLE 2-continued

LCMS analysis of active fraction 11-12 min from strain 2189

| Cpd | Label | Name | Formula | Score | Mass | Avg Mass | Std Dev | Base Peak | m/z | Vol % | Fraction |
|---|---|---|---|---|---|---|---|---|---|---|---|
| 36 | Cpd 36: Fludoxopone | Fludoxopone | C21 H21 N2 O3 F | 93.57 | 368.1523 | 372.4119 | | 373.131 | 373.131 | 0.90 | DT2189_11-12 min |
| 2 | Cpd 2: Gentamycin C1A | Gentamycin C1A | C19 H39 N5 O7 | 96.93 | 449.2859 | 431.5422 | | 432.2827 | 432.2827 | 0.84 | DT2189_11-12 min |
| 54 | Cpd 54: C31 H63 N O2 P2 S | | C31 H63 N O2 P2 S | 96.91 | 575.4056 | 575.7756 | | 576.4129 | 576.4129 | 0.83 | DT2189_11-12 min |
| 29 | Cpd 29: ferrulic acid # 537-98-4 | ferrulic acid # 537-98-4 | C10 H10 O4 | 93.73 | 194.0582 | 176.2607 | | 177.055 | 177.055 | 0.80 | DT2189_11-12 min |
| 20 | Cpd 20: Methyl palmitate (methyl-hexadecanoate) # 112-39-0 | Methyl palmitate (methyl-hexadecanoate) # 112-39-0 | C17 H34 O2 | 87.52 | 270.2548 | 287.5422 | | 288.289 | 288.289 | 0.79 | DT2189_11-12 min |
| 50 | Cpd 50: Mepitiostane | Mepitiostane | C25 H40 O2 S | 84.86 | 404.2768 | 386.5635 | | 387.2735 | 387.2735 | 0.71 | DT2189_11-12 min |
| 58 | Cpd 58: Lovastatin | Lovastatin | C24 H36 O5 | 92.76 | 404.2553 | 404.586 | | 405.2628 | 405.2628 | 0.71 | DT2189_11-12 min |
| 23 | Cpd 23: C27 H54 N3 O P S | | C27 H54 N3 O P S | 95.99 | 499.3732 | 499.7113 | | 500.3807 | 500.3807 | 0.69 | DT2189_11-12 min |
| 30 | Cpd 30: (2-Phenyl-1,3,-dioxolan-4-yl) methyloleate Phthalic acid # 88-99-3 | (2-Phenyl-1,3,-dioxolan-4-yl) methyloleate Phthalic acid # 88-99-3 | C8 H6 O4 | 85.65 | 166.0266 | 148.1255 | | 149.0233 | 149.0233 | 0.66 | DT2189_11-12 min |
| 1 | Cpd 1: Pseudo-pelletierene | Pseudo-pelletierene | C9 H15 N O | 88.3 | 153.1149 | 152.3791 | | 153.1384 | 153.1384 | 0.63 | DT2189_11-12 min |
| 52 | Cpd 52: Isomylamine | Isomylamine | C18 H35 N O2 | 65.55 | 297.2655 | 279.6263 | | 280.2645 | 280.2645 | 0.62 | DT2189_11-12 min |
| 13 | Cpd 13: C12 H27 N | | C12 H27 N | 85.52 | 185.2149 | 185.3589 | | 186.2222 | 186.2222 | 0.60 | DT2189_11-12 min |
| 60 | Cpd 60: Dinaline | Dinaline | C13 H13 N3 O | 87.11 | 227.1056 | 226.2623 | | 227.1289 | 227.1289 | 0.59 | DT2189_11-12 min |
| 11 | Cpd 11: Amixetrine | Amixetrine | C17 H27 N O | 76.11 | 261.2085 | 243.5454 | | 244.2059 | 244.2059 | 0.58 | DT2189_11-12 min |
| 42 | Cpd 42: C13 H38 N12 P2 | | C13 H38 N12 P2 | 80.15 | 424.2819 | 424.515 | | 425.2895 | 425.2895 | 0.57 | DT2189_11-12 min |
| 15 | Cpd 15: Hexetylamine | Hexetylamine | C16 H31 N O2 | 82.41 | 269.2361 | 286.4419 | | 287.2698 | 287.2698 | 0.50 | DT2189_11-12 min |
| 49 | Cpd 49: Podilfen | Podilfen | C18 H23 N3 O2 S | 94.72 | 345.1509 | 326.4241 | | 327.1398 | 327.1398 | 0.49 | DT2189_11-12 min |
| 28 | Cpd 28: Bepiastine | Bepiastine | C16 H17 N3 O S | 92.74 | 299.1088 | 298.3815 | | 299.1081 | 299.1081 | 0.49 | DT2189_11-12 min |
| 25 | Cpd 25: Bentazepam | Bentazepam | C17 H16 N2 O S | 75.21 | 296.0976 | 278.2737 | | 279.0943 | 279.0943 | 0.47 | DT2189_11-12 min |
| 26 | Cpd 26: Azoxystrobin #131860338 | Azoxystrobin #131860338 | C22 H17 N3 O5 | 92.11 | 403.1166 | 402.4446 | | 403.1397 | 403.1397 | 0.46 | DT2189_11-12 min |
| 32 | Cpd 32: Terbufos #13071799 | Terbufos #13071799 | C9 H21 O2 P S3 | 64.38 | 288.0455 | 327.5122 | | 327.0086 | 327.0086 | 0.43 | DT2189_11-12 min |
| 48 | Cpd 48: 19.540 | | | | 367.4194 | 367.7423 | | 368.4266 | 368.4266 | 0.36 | DT2189_11-12 min |
| 33 | Cpd 33: Flucythrinate #70124775 | Flucythrinate #70124775 | C26 H23 N O4 F2 | 85.24 | 451.1617 | 432.4811 | | 433.1505 | 433.1505 | 0.33 | DT2189_11-12 min |
| 53 | Cpd 53: C12 H26 O3 | | C12 H26 O3 | 83.17 | 218.189 | 218.3488 | 0.0002 | 219.1963 | 219.1963 | 0.33 | DT2189_11-12 min |
| 16 | Cpd 16: 4-Nonylphenol #104405 | 4-Nonylphenol #104405 | C15 H24 O | 71.8 | 220.1825 | 219.3997 | | 220.2063 | 220.2063 | 0.32 | DT2189_11-12 min |
| 47 | Cpd 47: C17 H31 N5 O | | C17 H31 N5 O | 75.48 | 321.2525 | 321.4628 | | 322.2605 | 322.2605 | 0.31 | DT2189_11-12 min |
| 34 | Cpd 34: C19 H41 N | | C19 H41 N | 81.33 | 283.3249 | 283.519 | | 284.3323 | 284.3323 | 0.30 | DT2189_11-12 min |

TABLE 2-continued

LCMS analysis of active fraction 11-12 min from strain 2189

| Cpd | Label | Name | Formula | Score | Mass | Avg Mass | Std Dev | Base Peak | m/z | Vol % | Fraction |
|---|---|---|---|---|---|---|---|---|---|---|---|
| 46 | Cpd 46: Phenicarbazide | Phenicarbazide | C7 H9 N3 O | 85.1 | 151.0739 | 150.1768 | | 151.0971 | 151.0971 | 0.22 | DT2189_11-12 min |
| 44 | Cpd 44: Camphor | Camphor | C10 H16 O | 81.34 | 152.1206 | 134.2487 | | 135.1174 | 135.1174 | 0.17 | DT2189_11-12 min |

TABLE 3

LCMS analysis of active fraction 3-4 min from strain 2189

| Cpd | Label | Name | Formula | Score | Mass | Avg Mass | Std Dev | Base Peak | m/z | Vol % | Fraction |
|---|---|---|---|---|---|---|---|---|---|---|---|
| 1 | Cpd 1: C13 H37 N11 | | C13 H37 N11 | 69.32 | 347.3243 | 347.6906 | | 348.3322 | 348.3322 | 29.10 | DT2189_3-4 min |
| 3 | Cpd 3: C5 H2 S4 | | C5 H2 S4 | 76.8 | 189.9054 | 190.2139 | | 190.9125 | 190.9125 | 11.14 | DT2189_3-4 min |
| 8 | Cpd 8: Dihydroxy-dibutylether, 3,3'- | Dihydroxy-dibutylether, 3,3'- | C8 H18 O3 | 86.57 | 162.1257 | 162.2349 | 0.0001 | 163.133 | 163.133 | 9.86 | DT2189_3-4 min |
| 7 | Cpd 7: Azelaic acid | Azelaic acid | C9 H16 O4 | 93.01 | 188.1055 | 188.2845 | 0.0001 | 206.1392 | 206.1392 | 8.61 | DT2189_3-4 min |
| 11 | Cpd 11: C21 H22 N6 O9 | | C21 H22 N6 O9 | 97.82 | 502.1445 | 502.4624 | | 503.1518 | 503.1518 | 8.41 | DT2189_3-4 min |
| 15 | Cpd 15: tricarboxylate) Triphenyl phosphate (diphenoxy-phosphoryloxy-benzene) # 115-86-6 | tricarboxylate) Triphenyl phosphate (diphenoxy-phosphoryloxy-benzene) # 115-86-6 | C18 H15 O4 P | 94.31 | 326.072 | 326.3175 | 0.0001 | 327.0793 | 327.0793 | 5.64 | DT2189_3-4 min |
| 13 | Cpd 13: Propizepine: | Propizepine: | C17 H20 N4 O | 94.43 | 296.1636 | 278.4036 | 0.0014 | 279.1601 | 279.1601 | 5.19 | DT2189_3-4 min |
| 12 | Cpd 12: Misoprostol | Misoprostol | C22 H38 O5 | 93.61 | 382.2714 | 399.6151 | | 400.3055 | 400.3055 | 3.73 | DT2189_3-4 min |
| 2 | Cpd 2: Glycerol | Glycerol | C3 H8 O3 | 94.3 | 92.0474 | 130.2417 | | 131.0106 | 131.0106 | 3.73 | DT2189_3-4 min |
| 6 | Cpd 6: Azelaic acid | Azelaic acid | C9 H16 O4 | 84.54 | 188.1054 | 170.2126 | | 171.1021 | 171.1021 | 3.60 | DT2189_3-4 min |
| 4 | Cpd 4: Prifuroline | Prifuroline | C14 H16 N2 O | 82.16 | 228.126 | 209.2254 | | 210.1149 | 210.1149 | 2.75 | DT2189_3-4 min |
| 10 | Cpd 10: Hexetylamine | Hexetylamine | C16 H31 N O2 | 79.41 | 269.2363 | 286.4451 | | 287.2703 | 287.2703 | 2.72 | DT2189_3-4 min |
| 5 | Cpd 5: C8 H19 N | | C8 H19 N | 83.49 | 129.151 | 129.2532 | | 130.1583 | 130.1583 | 2.18 | DT2189_3-4 min |
| 14 | Cpd 14: (2-Phenyl-1,3,-dioxolan-4-yl) methyloleate Phthalic acid # 88-99-3 | (2-Phenyl-1,3,-dioxolan-4-yl) methyloleate Phthalic acid # 88-99-3 | C8 H6 O4 | 84.87 | 166.0269 | 148.1378 | | 149.0236 | 149.0236 | 1.95 | DT2189_3-4 min |
| 9 | Cpd 9: C11 H6 N4 O3 | | C11 H6 N4 O3 | 81.36 | 242.0429 | 242.1855 | | 243.0502 | 243.0502 | 1.39 | DT2189_3-4 min |

TABLE 4

LCMS analysis of active fraction 3-4 min from strain 75

| Cpd | Label | Name | Formula | Score | Mass | Avg Mass | Std Dev | Base Peak | m/z | Vol % | Fraction |
|---|---|---|---|---|---|---|---|---|---|---|---|
| 3 | Cpd 3: Dihydroxy-dibutylether, 3,3'- | Dihydroxy-dibutylether, 3,3'- | C8 H18 O3 | 86.49 | 162.1255 | 162.2501 | 0 | 163.1328 | 163.1328 | 28.26 | DT75_3-4 min |
| 1 | Cpd 1: Propizepine: | Propizepine: | C17 H20 N4 O | 97.63 | 296.1634 | 316.4328 | | 317.116 | 317.116 | 27.64 | DT75_3-4 min |
| 6 | Cpd 6: C10 H20 O4 | | C10 H20 O4 | 84.25 | 204.1355 | 204.2749 | 0.0004 | 205.1428 | 205.1428 | 18.85 | DT75_3-4 min |
| 2 | Cpd 2: Asulam | Asulam | C8 H10 N2 O4 S | 90.47 | 230.0371 | 230.3284 | | 231.0443 | 231.0443 | 12.50 | DT75_3-4 min |
| 4 | Cpd 4: Octamylamine | Octamylamine | C13 H29 N | 86.94 | 199.2298 | 199.3899 | | 200.2371 | 200.2371 | 7.49 | DT75_3-4 min |
| 5 | Cpd 5: C14 H31 N | | C14 H31 N | 86.25 | 213.2453 | 213.3975 | | 214.2526 | 214.2526 | 5.26 | DT75_3-4 min |

TABLE 5

LCMS analysis of active fraction 10-11 min from strain 75

| Cpd | Label | Name | Formula | Score | Mass | Avg Mass | Std Dev | Base Peak | m/z | Vol % | Fraction |
|---|---|---|---|---|---|---|---|---|---|---|---|
| 5 | Cpd 5: Butaprost | Butaprost | C24 H40 O5 | 96.89 | 408.2871 | 390.575 | 0.0007 | 391.2836 | 391.2836 | 54.86 | DT75_10-11 min |
| 1 | Cpd 1: Dihydroxy-dibutylether, 3,3'- | Dihydroxy-dibutylether, 3,3'- | C8 H18 O3 | 83.98 | 162.1249 | 162.2276 | 0.0002 | 163.1321 | 163.1321 | 19.02 | DT75_10-11 min |
| 4 | Cpd 4: C10 H20 O4 | | C10 H20 O4 | 83.12 | 204.1358 | 204.2701 | 0.0005 | 205.1422 | 205.1422 | 11.39 | DT75_10-11 min |
| 6 | Cpd 6: Misoprostol | Misoprostol | C22 H38 O5 | 89.85 | 382.2704 | 399.6323 | | 400.3043 | 400.3043 | 6.55 | DT75_10-11 min |
| 2 | Cpd 2: Octamylamine | Octamylamine | C13 H29 N | 86.05 | 199.2294 | 199.376 | | 200.2367 | 200.2367 | 4.92 | DT75_10-11 min |
| 3 | Cpd 3: C14 H31 N | | C14 H31 N | 86.36 | 213.2453 | 213.3939 | | 214.2526 | 214.2526 | 3.26 | DT75_10-11 min |

Toxicity testing in mammalian cells—Analysis of *Delftia* supernatant inhibitory effect on human primary cells: In order to rule out non-specific toxicity of the active *Delftia* supernatant, the effect of the active supernatant from strain 2189 was tested on eukaryotic cells, namely on primary kidney tubular epithelial cells and melanoma cells using an MTS Assay.

FIGS. 17A-B show that there is no inhibitory effect by supernatant of strain 2189 on primary human kidney cell growth after exposure for 3 and 4 days.

Three types of human melanoma cells were analyzed for cell death by the active compounds: 526mel, 624mel and 003mel.

Specifically, 5,000 cells (human melanoma) were seeded in 96 well plate together with 5 ul of 2189 sup which was diluted to different concentrations (1:1=no dilution, 1:10, 1:100) for 1-3 days. Then cells were FACS analyzed for the existence of dead cells by PI staining.

As illustrated in FIG. 18, no inhibitory effect was detected against the three different types of human melanoma cells.

As illustrated in FIGS. 19A-B, *Delftia* strain 2189 showed no hemolytic effected on sheep red blood cells.

16srRNA sequencing: Additional isolates were uncovered using a novel *Delftia* selective agar (DSA). DSA is composed of minimal media, 0.5% phthalic acid as a carbon source and antibiotic cocktail (ampicillin 200 microgram/ml & gentamicin 50 microgram/ml). The identity of the novel isolates was confirmed by 16srRNA sequencing (FIGS. 22A-G). The specificity and the selectivity of the DSA is displayed in Table 6.

TABLE 6

*Delftia* Selective Agar

| Number | Strain | Gram stain | Growth on Selective Agar |
|---|---|---|---|
| 1 | *Delftia* strain 75 | negative | +++ |
| 2 | *Delftia* strain 2189 | negative | +++ |
| 3 | *Delftia* strain 2248 | negative | +++ |
| 4 | *Delftia* strain 2361 | negative | +++ |
| 5 | *Delftia* strain 2350 | negative | +++ |
| 6 | *Delftia* strain 2260 | negative | +++ |
| 7 | *D. tsuruhatensis* strain T-7 | negative | -/+ |
| 8 | *P. aeruginosa* ATCC 9027 | negative | − |
| 9 | *P. aeruginosa* ATCC 10145 | negative | − |
| 10 | *E. aerogenes* ATCC 13048 | negative | − |
| 11 | *S. flexneri* | negative | − |
| 12 | *S. sonnei* ATCC 25931 | negative | − |
| 13 | *E. coli* ATCC 29522 | negative | − |
| 14 | *L. monocytogenes* ATCC 19155 | positive | − |
| 15 | *S. enterica Enteritidis* ATCC 19076 | negative | − |
| 16 | *S. aureus* ATCC 25923 | positive | − |
| 17 | *E. faecalis* ATCC 29212 | positive | − |
| 18 | *K. pneumoniae* ATCC 13883 | negative | − |
| 19 | *S. epidermidis* ATCC 62228 | positive | − |
| 20 | *A. cinetobacter* sp. | negative | − |

The antimicrobial activity of the additional *Delftia* that were uncovered using the DSA medium was analyzed. Results are provided in FIG. 21.

Additional Characteristics of the *Delftia* Strains

Carbon source: Strains 2189, 2350 (from European MW) and 75 (from Israeli MW) are able to utilize high concentration of phthalic acid (3,500 ppm, not shown) as a sole source of carbon, but are unable to utilize terephthalic acid. In contrast, the Japanese clone T-7 (13) is able to utilize terephthalic acid, but not phthalic acid.

Biofilm formation: As illustrated in FIGS. 23A-D, *Delftia* strain 2189 produces a biofilm in response to various toxic compounds. *Delftia* strain 2189 was incubated in 1 ml NB containing toxic compounds, for 24 hours at 30° C. with no shaking. 8 μl samples were used for phase contrast microscopy. A3 demonstrate reversion of cells into normal morphology achieved by centrifugation of the culture to remove the inhibitor containing supernatant and re-suspension in fresh NB.

Formation of "fruiting bodies": During starvation, (after 6 days of incubation at 30° C.), dramatic morphological changes were apparent at the center of the colonies and production of fruiting bodies like structures were noted (FIG. 24A).

Concurrently with the appearance of the fruiting bodies the *Delftia* cells appeared rounded, and stained as Gram positive cocci (FIG. 24C). Starved *Delftia* cells containing spore like bodies were significantly more resistant to heat and other physical and chemical types of stress, relatively to vegetative cells (not shown). The typical fruiting bodies were not produced by strain T7.

Sequencing: Strain 2189 was sequenced using the 454 WGS platform Approximately 5% of *Delftia* genome is intended for virulence and defense properties, the bacteria also contains various genes for resistance to heavy metal, toxic substances and antibiotic compounds. Indeed *Delftia* is a multi-drug resistant (MDR) organism. The 2189 genome also contains genes for type IV pilus as well as for conjugation, suggesting virulence mechanisms. The 7 Mb genome encodes for approximately 6,800 genes, 28% of unknown functions. So far, strain 2189 has the biggest genome relatively to the other 2 sequenced *Delftia* strains (*D. acidivorans* SPH-1, 6.77 Mb and *Delftia* Cs1-4 6.69 Mb) which have been published. The overall gene composition of the genome is displayed in FIG. 22G.

The npdA gene which encodes a nanopod (serving as a conduit for projecting outer member vesicles for significant distances (≥6 microns)) is presented in the genome of clone 2189 and it is expressed.

The 2189 genome also contains a large 40 Kb locus encoding for type VI secretion system (T6SS). The T6SS locus is encoding for 33 open reading frames, many of them of unknown function. T6SS serves as molecular syringe for contact delivery of various effectors to eukaryotic as well as prokaryotic organisms. T6SS proteins are evolutionarily and structurally related to phage proteins, and it is likely that the T6SS apparatus is reminiscent of phage injection machinery. Most studies of T6SS function have been conducted in the context of host-pathogen interactions.

However, the overall data suggests that the T6SS is a versatile tool with roles in virulence aspects, symbiosis, interbacterial interactions, and antipathogenesis. In order to test whether the T6SS is responsible for the observed contact dependent inhibition of target bacteria, they tested the ability of *Delftia* Cs1-4 that was knocked out in one of the key component of T6SS, the haemolysin coregulated protein-Hcp (*Delftia* Cs1-4 Δhcp::km, (24)) to kill target cells of *S. aureus* USA300. While the wild type Cs1-4 display efficient predataxis and killing of the target cells, the Cs1-4 Δhcp::km was found to be defective in predataxis and in its ability to kill the target cells.

The sequence of strain 2189 was uploaded to the RAST (Rapid Annotation using Subsystem Technology) server for fully-automated genome annotating.

The results are displayed in FIGS. 25A-B. FIGS. 22A-G illustrate the overall gene composition of strains 75-A, 119-B, 120-C, 261-D, 122-E, 123-F and 2189-G.

Additional experiments were performed in an attempt to isolate different antimicrobial agents from the *Delftia* bacteria—see FIG. 30 for outline.

*Delftia* strains 75 and 2189 were grown in Davis minimal broth without Dextrose (Difco™ BD 275610) with addition of 0.5% Glycerol (Sigma-Aldrich G7893), in volume of 100 ml in 500 ml Erlenmeyer without shaking at 30° C.

Supernatants were filtered first through 0.4504 and then using 3 KDa Amicom ultra-15 centrifugal filter, or Sartorius Vivaspin 20 ml, and lyophilized. Following suspension in water, the sample was then centrifuged. Both the supernatant fraction and the pellet fraction were run using an acetonitrile gradient (solvent A water:AcN 90:10, solvent B water:AcN 10:90, both with 13 mM ammonium formate and 0.01% TFA) on a preparative Waters Atlantis T3 column (4.6×100 mm, 5 μm particle size HPLC column. The signals were detected by diode array detector. Two wavelengths 220 and 280 nm were used to detect the peaks. Fractions were collected using a fraction collector. The volume of sample injected was 4 μl. The gradient composition is set forth in Table 7 herein below:

TABLE 7

| Retention Time (minutes) | A | B | Flow (mL/min) |
| --- | --- | --- | --- |
| 0.0 | 100 | 0 | 0.5 |
| 11.0 | 0 | 100 | 0.5 |
| 16.0 | 0 | 100 | 0.5 |
| 16.1 | 100 | 0 | 0.5 |
| 20.0 | 100 | 0 | 0.5 |

A variety of peaks at different retention times were detected for both the supernatant and the pellet fraction.

The mass spectrometer was operated in positive ESI mode. The instrumental parameters were: 4 kV capillary voltage, drying gas flow of 11 L/min at 200° C., nebulizer pressure at 2.8 bars.

TFA-Na cluster ions were used for mass calibration of the instrument prior to sample injection. Each sample run was recalibrated by infusion with the same TFA-NA calibrant before the chromatographic front.

Each chromatographic run was processed using Bruker algorithm for components extraction, and the most intense peaks of each run, either by UV or positive TIC were considered for interpretation of exact mass and molecular formula by studying the extracted mass components.

Supernatant Fraction:

As seen in FIGS. 26A-B, both peaks, P1 and P2, contained the same component of mass 1032.4829. The interpretation of molecular formula returned two possible molecular formulae, $C_{42}H_{80}O_{28}$ and $C_{40}H_{68}N_{14}O_{18}$ that were not found in the Dictionary of Natural Products.

The material was dissolved in $D_2O$ and ran $^1H$ and $^{13}C$ spectra of this sample, at 300K, in Bruker Avance-III-700 instrument (at 700.5 and 176.1 MHz, respectively). In addition, three 2D experiments were run: COSY ($^1H×^1H$ correlation) HMQC (one-bond $^1H\times^{13}C$ correlation) and HMBC (long-range $^1H\times^{13}C$ correlation).

The $^1$H-NMR and HSQC spectra of sample Delphar-01 showed the presence of amino acids in the structure, and therefore, the two possible molecular formulae were revisited and that of the compound was established as $C_{40}H_{68}N_{14}O_{18}$. The primary examination of the spectra suggested that this was a polypeptide. The presence of a few known amino acid residues was confirmed: glycine, serine, threonine and arginine. Two sets of peaks were identified (1,5-diamino pentanoic acid), also known as ornithine. Three more molecular fragments were detected. One contained a double bond (in the Table below, referred to as residues "A", "B" and "C"). A formyl fragment was also detected. The presence of the latter could explain the fact that the spectrum actually indicated a 3:1 mixture (vide infra). The $^{13}$C spectrum showed the presence of 10 signals in the region for amide/acid carbonyls, as expected for a polypeptide. With this information in hand, the present inventors lyophilized away the $D_2O$ solvent, and ran the spectra again, this time in a mixture of 10% $D_2O$ and 90% $H_2O$ in order to observe the signal for the amide NH's (in $D_2O$, the latter are substituted by deuterium and do not appear in the spectrum). Indeed, it turned out that several of these of signals were observed. For this solution, we obtained three more types of 2D experiments: TOCSY ($^1H\times^1H$ total correlation), ROESY (a $^1H\times^1H$ NOE experiment detected in the rotating frame—this experiment also proved that the two formamide species were present in dynamic equilibrium) and HMBC-N($^1H\times^{15}N$ correlation). The computer-produced fit was excellent for $C_{40}H_{68}N_{14}O_{18}$. Analysis of the NMR chemical shifts of the known chemical Delftibactin A, which has the same chemical formula, showed unequivocally that the two compounds were indeed identical. The structure of Deftibactin is presented in FIG. 28A. The numbering of the atoms is identical to the paper of C. W. Johnston, M. A. Wyatt, X. Li, A. Ibrahim, J. G. Southam and N. A. Magarvey, *Nature Chem. Biol.* 9, 241 (2013)] The assignment for Delftibactin A is presented in Table 8, herein below. The structure of "formamide rotamers" is specified in FIG. 28B. These two species are in dynamic equilibrium and interconvert every few tens of seconds. This is slow in the NMR time-scale, so two sets of signals are observed, but is fast as far as biological activity or separation techniques are concerned. Some carbons (and two protons) for the minor rotamer could be identified and are presented in the right side of the Table 8.

TABLE 8

| | major rotamer | | minor rotamer | |
|---|---|---|---|---|
| | $^1$H | $^{13}$C ($^{15}$N) | $^1$H | $^{13}$C ($^{15}$N) |
| N-Hydroxy-Ornithine | | | | |
| 1 | — | 166.98 | | |
| 2 | 3.62, 3.68 | 51.68 | | |
| 3 | 1.62 | 20.03 | | |
| 4 | 1.77, 2.02 | 26.62 | | |
| 5 | 4.43 | 50.43 | | |
| NH | 8.28 | (122.0) | | |
| Arginine[a] | | | | |
| 6 | — | 172.83 | | |
| 7 | 4.34 | 53.52 | | 53.58 |
| NH | 8.29 | (122.8) | | |
| 8 | 1.76, 1.91 | 28.08 | | |
| 9 | 1.60, 1.68 | 24.36 | | |
| 10 | 3.19 | 40.55 | | |

TABLE 8-continued

| | major rotamer | | minor rotamer | |
|---|---|---|---|---|
| | $^1$H | $^{13}$C ($^{15}$N) | $^1$H | $^{13}$C ($^{15}$N) |
| NH | 7.17 | (84.7) | | |
| 11 | — | 156.78 | | |
| Serine | | | | |
| 12 | — | 171.48 | | |
| 13 | 4.41 | 55.83 | | 55.93 |
| NH | 8.25 | (116.3) | | |
| 14 | 3.84, 3.88 | 60.86 | | 60.89 |
| N-Hydroxy-Ornithine | | | | |
| 15 | — | 172.98 | | |
| 16 | 4.38 | 53.96 | | 54.01 |
| NH | 8.11 | (118.1) | | |
| 17 | 1.78, 1.91 | 27.46 | | 27.65 |
| 18 | 1.70, 1.78 | 22.87 | | 22.32 |
| 19 | 3.58 | 49.98 | 3.61 | 46.03 |
| 20 | 7.95 | 159.68 | 8.29 | 163.90 |
| Residue "A" | | | | |
| 21 | — | 166.51 | | |
| 22 | — | 127.82 | | |
| NH | 9.39 | (119.7) | | |
| 23 | 6.67 | 134.54 | | |
| 24 | 1.75 | 12.64 | | |
| Glycine | | | | |
| 25 | — | 174.15 | | |
| 26 | 4.06, 4.09 | 42.99 | | |
| NH | 8.58 | (111.0) | | |
| Threonine | | | | |
| 27 | — | 171.93 | | |
| 28 | 4.40 | 59.12 | | |
| NH | 8.22 | (115.2) | | |
| 29 | 4.37 | 66.82 | | |
| 30 | 1.21 | 18.82 | | |
| Residue "C" | | | | |
| 31 | — | 171.10 | | |
| 32 | 4.85 | 55.85 | | |
| NH | 8.53 | (121.3) | | |
| 33 | 4.42 | 71.23 | | |
| 34 | — | 175.49 | | |
| Residue "B" | | | | |
| 35 | — | 176.33 | | |
| 36 | 2.62 | 43.26 | | |
| 37 | 1.26 | 14.80 | | |
| 38 | 3.88 | 72.00 | | |
| 39 | 3.40 | 49.19 | | |
| 40 | 1.25 | 10.82 | | | a. Other guanidine unit protons form a broad hump at δ 7.7.

FIG. 27A-B illustrates the results of the spectral analysis of purified Delfibactin A. Delfibactin A was shown to absorb mainly at 220 nm. The main isomer eluted at 12.6 minutes (70%)—FIG. 27A, whilst the secondary isomer eluted at 12.1 minutes at 30%—FIG. 27B.

Pellet Fraction

Antimicrobial activity was also found in the pellet fraction. Specifically Delftactin A was detected (1033 daltons) and Delftibactin B (1047 daltons).

Another compound with the molecular formula: $C_{39}H_{68}N_{14}O_{17}$ detected by LC-MS, this compound most likely belongs to the delftibactins—see FIGS. 29A-B.

FIG. 29A shows the trace of UV absorbance at 210 nm for reverse phase HPLC fraction at 11.5 min. Peak 1 suggested molecular formula $C_{39}H_{68}N_{14}O_{17}$. This compound was purified and confirmed to display weak antimicrobial activity. Peak 2 Suggested molecular formula: $C_{14}H_{24}N_2O_7$ with a unique match in the DNP for spectinomycin which is known to be active against Gram-positive and -negative bacteria. The experimental UV spectrum and fragmentation did not corroborate the presence of spectinomycin. Peak 3 suggested the molecular formula: $C_{10}H_{14}N_2O_5$, with coincidence by molecular formula and UV spectrum with thymidine.

Determination of Minimal Inhibitory Concentration:

Delftibactin A was serially diluted in DMSO with a dilution factor of 2, to provide 10 concentrations for all the assays. The MIC is defined as the lowest concentration of compound that inhibited ≥90% or ≥50% of the growth of a microorganism after overnight incubation. Genedata Screener software (Genedata, Inc., Basel, Switzerland) was used to analyze the data and to determine the MICs and calculate the RZ' factor, to estimate the robustness of the assays. Delftibactin A was tested on two different days and in triplicate.

Broth microdilution was used to determine the minimal inhibitory concentration (MIC) according to the standards of the Clinical and Laboratory Standards Institute (CLSI) or the European Committee on Antimicrobial Susceptibility Testing (EUCAST). Cation-adjusted Mueller-Hinton broth (CAMHB) was used with inoculum of about $5\times10^5$ cfu ml$^{-1}$ of the tested pathogen. Direct suspension of overnight colonies into CAMHB was used for the generation of the bacterial suspension. The tested inhibited compound or supernatant was used in doubling dilutions in 50 µl of CAMHB and inoculated with an equal amount of bacteria in the broth.

The $MIC_{50}$ of Delftibactin A on gram negative bacteria are provided in FIGS. 31 and 32.

FIG. 33 illustrates that Delftbactin A inhibits vancomycin resistant enterococci (VRE).

The $MIC_{50}$ of Delftibactin A on the yeast C. albicans ATCC64124 is 16 µg/ml.

FIG. 34 illustrates that Delftibactin A (10 µM) has additive combined antimicrobial effect with clarithromycin on VRE and FIG. 35 illustrates that Delftibactin A (10 µM) has additive combined antimicrobial effect with rifampicin on VRE.

Delftibactin A is known to bind metals such as gold and gallium. Thus, Delftibactin A can be used as a carrier of inhibitory antimicrobial agents such as gallium to inhibit harmful bacterial strains such as Deftia strain 2189 (see FIG. 36).

Delftibactin A was also shown to not have cytotoxic activity in both THLE2 and HepG2 cell lines, as assayed using the MTT assay, as described herein below.

MTT (3-(4,5-Dimethylthiazol-2-yl)-2,5-diphenyltetrazolium bromide) is a colorimetric assay for measuring the activity of cellular enzymes that reduce the tetrazolium dye, MTT, to its insoluble formazan, giving a purple color. This assay measure mitochondrial metabolic activity via NAD(P)Hdependent cellular oxidoreductase enzymes and may, under defined conditions, reflect the number of viable cells. The cells used in this study were: Hep G2 (HB-8065) is a perpetual cell line which was derived from the liver tissue of a 15-year-old Caucasian American male with a well-differentiated hepatocellular carcinoma. THLE-2 is a perpetual cell line which was derived from the liver epithelial cells of an adult human male transformed with SV40 large T antigen.

The assay: cell concentration treatment 24 hours: Cells were seeded at a concentration of $2\times10^4$ cells/well in 200 µl culture medium and incubated at 37° C. in 5% $CO_2$. Cell concentration treatment 72 hours: Cells were seeded at a concentration of $1\times10^4$ cells/well in 200 µl culture medium and incubated at 37° C. in 5% $CO_2$. After 24 hours, the medium was replaced with a final volume of 200 µl and 1 µl of compound (dilution 1/200) and controls were added to the plates. As positive control, 8 mM methyl methanesulfonate (MMS), was used and DMSO 0.5% as negative control. As standards (internal control) Doxorubicin curve was used. Previously a DMSO curve was tested with these cell lines, and no effects were observed with 1% DMSO.

When extracts/compounds and controls were added, plates were incubated at 37° C. in 5% $CO_2$ incubator for 24/72 hours. After this time, MTT solution was prepared at 5 mg/ml in PBS 1× and then diluted at 0.5 mg/ml in MEM without phenol red. The sample solution in wells was flicked off and 1000 of MTT dye was added to each well. The plates were gently shaken and incubated for 3 hours at 37° C. in 5% $CO_2$ incubator. The supernatant was removed and 100 µl of DMSO 100% was added. The plates were gently shaken to solubilize the formed formazan. The absorbance was measured using a multireader Victor™ at a wavelength of 570 nm.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating an infection in a human subject in need thereof, the method comprising administering to the subject a therapeutically effective amount of Delftibactin A or Delftibactin B, thereby treating the infection.

2. The method of claim 1, further comprising administering to the subject an antibiotic.

3. The method of claim 1, wherein said Delftibactin A or said Delftibactin B is attached to an antimicrobial agent.

4. The method of claim 3, wherein said antimicrobial agent comprises gold or gallium.

5. A method of killing a microbe, the method comprising contacting the microbe with isolated Delftibactin A or Delftibactin B, thereby killing the microbe.

6. The method of claim 5, further comprising contacting the microbe with an antibiotic.

\* \* \* \* \*